US012691067B2

(12) United States Patent
Ventosa Rull et al.

(10) Patent No.: US 12,691,067 B2
(45) Date of Patent: Jul. 28, 2026

(54) LIPOSOMES AND ITS USE FOR ENZYME DELIVERY

(71) Applicants: CONSEJO SUPERIOR DE INVESTIGACIONES CIENTÍFICAS (CSIC), Madrid (ES); NANOMOL TECHNOLOGIES, S.L., Cerdanyola Del Valles (ES); LEANBIO, Barcelona (ES)

(72) Inventors: Leonor Ventosa Rull, Bellaterra (ES); Jaume Veciana Miró, Bellaterra (ES); Miriam Royo Exposito, Barcelona (ES); Judit Tomsen Melero, Bellaterra (ES); Ibane Abasolo Olaortua, Barcelona (ES); Simón Schwartz Navarro, Sabadell (ES); Jose Luis Corchero Nieto, Cerdanyola Del Valles (ES); Daniel Pulido Martinez, Barcelona (ES); Edgar Cristóbal Lecina, Barcelona (ES); Elisabet González Mira, Bellaterra (ES); Santiago Sala Vergés, Cerdanyola Del Valles (ES); Alba Córdoba Insensé, Cerdanyola Del Valles (ES); Josep Merlo Mas, Cerdanyola Del Valles (ES); Andreu Soldevila Fábrega, Barcelona (ES); Albert Font Inglés, Barcelona (ES)

(73) Assignees: CONSEJO SUPERIOR DE INVESTIGACIONES CIENTIFICAS (CSIC), Madrid (ES); NANOMOL TECHNOLOGIES, S.L., Cerdanyola del Valles (ES); LEANBIO, Barcelona (ES)

( * ) Notice: Subject to any disclaimer, the term of this patent is extended or adjusted under 35 U.S.C. 154(b) by 240 days.

(21) Appl. No.: 18/274,631

(22) PCT Filed: Jan. 26, 2022

(86) PCT No.: PCT/EP2022/051727
§ 371 (c)(1),
(2) Date: Jul. 27, 2023

(87) PCT Pub. No.: WO2022/161990
PCT Pub. Date: Aug. 4, 2022

(65) Prior Publication Data
US 2024/0115502 A1 Apr. 11, 2024

(30) Foreign Application Priority Data
Jan. 27, 2021 (EP) .................................... 21382062

(51) Int. Cl.
*A61K 9/1272* (2025.01)
*A61K 9/1277* (2025.01)
(Continued)

(52) U.S. Cl.
CPC .......... *A61K 9/1272* (2013.01); *A61K 9/1277* (2013.01); *A61K 38/47* (2013.01);
(Continued)

(58) Field of Classification Search
None
See application file for complete search history.

(56) References Cited

U.S. PATENT DOCUMENTS

| | | | | |
|---|---|---|---|---|
| 9,744,247 B2* | 8/2017 | Ventosa Rull | ............ | A61P 3/00 |
| 2004/0071686 A1* | 4/2004 | Treco | ........................ | A61P 3/00 |
| | | | | 424/94.61 |

(Continued)

FOREIGN PATENT DOCUMENTS

| | | | |
|---|---|---|---|
| EP | 1843836 B1 | 3/2009 |
| WO | 2006079889 A1 | 8/2006 |
| WO | 2014001509 A1 | 1/2014 |

OTHER PUBLICATIONS

Guillem Vargas-Nadal et al. "MKC-Quatsomes: a stable nanovesicle platform for bioimaging and drug-delivery applications." Nanomedicine: Nanotechnology, Biology and Medicine, vol. 24 (2020) 102136, pp. 1-9 and 9 supplemental pages, of record Jan. 9, 2020. (Year: 2020).*

(Continued)

*Primary Examiner* — Isaac Shomer
(74) *Attorney, Agent, or Firm* — Hayes Soloway, PC

(57) ABSTRACT
The present invention refers to a liposome comprising: a) a phospholipid; b) cholesterol (chol); c) a conjugate compris-
(Continued)

ing a cholesterol moiety, a polyethylene glycol (PEG) moiety and a peptide moiety comprising a RGD sequence, wherein the PEG moiety is covalently attached to the cholesterol moiety by one end via a bond of the type alkyl ether and is covalently attached to the peptide moiety comprising the RGD sequence by the other end: d) a non-lipid cationic surfactant present in a percentage of less than 30% mol in respect to the total mol of the components of the liposome a), b), c) and d); and e) alpha-galactosidase (GLA) enzyme present in a ratio of micrograms of GLA in respect to the total milligrams of the components of the liposome a), b), c) and d) of between and including 2 to 35.

14 Claims, 13 Drawing Sheets

Specification includes a Sequence Listing.

(51) Int. Cl.
| | | |
|---|---|---|
| *A61K 38/47* | (2006.01) | |
| *A61K 47/26* | (2006.01) | |
| *A61P 3/06* | (2006.01) | |

(52) U.S. Cl.
CPC ................ *A61K 47/26* (2013.01); *A61P 3/06* (2018.01); *C12Y 302/01022* (2013.01)

(56) References Cited

U.S. PATENT DOCUMENTS

| | | | |
|---|---|---|---|
| 2015/0190530 A1* | 7/2015 | Ventosa Rull | ....... A61K 47/554 428/402 |
| 2017/0165198 A9 | 6/2017 | Kim et al. | |
| 2019/0358302 A1* | 11/2019 | Gotschall | ............. C12N 9/2465 |

OTHER PUBLICATIONS

Annie-Louise Robson et al. "Advantages and Limitations of Current Imaging Techniques for Characterizing Liposome Morphology." Frontiers in Pharmacology, vol. 9 Article 80, Feb. 2018, pp. 1-8. (Year: 2018).*

Guillem Vargas Nadal. "Novel Quatsome nanovesicles, prepared using compressed CO2, for the development of advanced nanomedicines." Universitat de Barcelona, Thesis, pp. i-xxii, 1-295, and additional pages of appended papers, Jun. 2020. (Year: 2020).*

JN Israelachvili, S Marcelja, and RG Horn. "Physical principles of membrane organization." Quarterly Reviews of Biophysics, vol. 13(2), 1980, pp. 121-200. (Year: 1980).*

Komol Kanta Sharker, Shin-ichi Yusa, and Chi Minh Phan. "Micellar formation of cationic surfactants." Heliyon, vol. 5, 2019, article e02425, pp. 1-11. (Year: 2019).*

Guillem Vargas-Nadal et al. "MKC-Quatsomes: a stable nanovesicle platform for bio-imaging and drug-delivery applications." Nanomedicine: Nanotechnology, Biology, and Medicine, vol. 24, 2020, 102136, pp. 1-9 and 7 supplementary pages. (Year: 2020).*

Tao Chen & Liming Dai, "Carbon nanomaterials for high-performance supercapacitors", Journal, Jul./Aug. 2013, p. 272-280, vol. 16, No. 7/8, Materials Today.

Wang et al., "Electrochemical capacitors: mechanism, materials, systems, characterization and applications", Journal, Aug. 2016, p. 5925-5950, vol. 45, Chem. Soc. Rev.

Dubal et al., "Hybrid energy storage: the merging of battery and supercapacitor chemistries", Journal, Jan. 2015, p. 1777-1790, vol. 44, Chem. Soc. Rev.

Augustyn et al., "Pseudocapacitive oxide materials for high-rate electrochemical energy storage", Journal, Mar. 2014, p. 1597-1614, vol. 7, Energy & Environmental Science.

Patrice Simon & Yury Gogotsi, "Materials for electrochemical capacitors", Article, Nov. 2008, p. 845-854, vol. 7, Nature Materials.

Liu et al., "Transition Metal based Battery-Type Electrodes in Hybrid Supercapacitors: A Review", Journal, Jun. 2020, p. 122-145, vol. 28, Energy Storage Materials.

Li et al., "Facile Synthesis of Bimetal Nickel Cobalt Phosphate Nanostructures for High-Performance Hybrid Supercapacitors", Journal, 2022, p. 1623-1640, vol. 893, Journal of Alloys and Compounds.

Salunkhe et al., "A Concept for Asymmetric Supercapacitors Using 3D Nanoporous Carbon and Cobalt Oxide Electrodes Synthesized from Single Metal Organic Framework", Article, May 15, 2015, p. 1-27, ACS Nano.

Lifeng Liu, "Nano-aggregates of cobalt nickel oxysulfide as a high-performance electrode material for supercapacitors", Article, 2013, p. 1-5, vol. 5, Nanoscale.

Liu et al., "Flower-like manganese-cobalt oxysulfide supported on Ni foam as a novel faradaic electrode with commendable performance", Article, Jan. 20, 2016, p. 1-26, Electrochimica Acta.

Nagaraju et al., "Wearable Fabrics with Self-Branched Bimetallic Layered Double Hydroxide Coaxial Nanostructures for Hybrid Supercapacitors", Article, 2017, p. 1-45, ACS Nano.

Kumar et al., "Facile synthesis of highly efficient construction of tungsten disulfide/iron cobaltite nanocomposite grown on nickel foam as a battery-type energy material for electrochemical supercapacitors with superior performance", Journal, 2022, p. 434-448, vol. 609, Journal of Colloid and Interface Science.

Tran et al., "High-efficient Overall Water Splitting Over Porous Interconnected Network by Nickel Cobalt Oxysulfide Interfacial Assembled Cu@Cu2S Nanowires", Journal, 2020, p. 1-13, Journal of Materials Chemistry A.

Wang et al., "Insight into Nickel-Cobalt Oxysulfide Nanowires as Advanced Anode for Sodium-Ion Capacitors", Article, 2021, p. 1-9, vol. 11, Advanced Science News, Advanced Energy Materials.

Wang et al., "Facile Synthesis of Flower-Like Copper-Cobalt Sulfide as Binder-Free Faradaic Electrodes for Supercapacitors with Improved Electrochemical Properties", Article, 2017, p. 1-11, vol. 7, No. 140, Nanomaterials.

Loussot et al., "Amorphous Cobalt Oxysulfide as a Hydrogen Trap", Article, 2006, p. 5659-5668, vol. 18, No. 24, Chem. Mater.

Nagaraju et al., "An agriculture-inspired nanostrategy towards flexible and highly efficient hybrid supercapacitors using ubiquitous substrates", Journal, Dec. 2019, p. 1-41, vol. 66, Nano Energy.

Pallavolu et al., "Self-assembled and highly faceted growth of Mo and V doped ZnO nanoflowers for high-performance supercapacitors", Journal, 2021, p. 1-12, vol. 886, Journal of Alloys and Compounds.

Chen et al., "One-Step Electrodeposited Nickel Cobalt Sulfide Nanosheet Arrays for High-Performance Asymmetric Supercapacitors", Article, 2014, p. 9531-9541, vol. 8, No. 9, ACS Nano.

Kong et al., "Homogeneous core-shell NiCo2S4 nanostructure supported on nickel foam for supercapacitors", Article, May 2015, p. 1-33, vol. 3, Journal of Materials Chemistry A.

Zhang et al., "Electrochemically Synthesis of Nickel Cobalt Sulfide for High-Performance Flexible Asymmetric Supercapacitors", Article, 2017, p. 1-12, Advanced Science News.

Shude Liu and Seong Chan Jun, Hierarchical manganese cobalt sulfide core-shell nanostructures for high-performance asymmetric supercapacitors, Article, 2017, p. 629-637, vol. 342, Journal of Power Sources.

Nagaraju et al., "An Integrated Approach Toward Renewable Energy Storage Using Rechargeable Ag@Ni0.67Co0.33S-Based Hybrid Supercapacitors", Article, 2019, p. 1-14, Nano-Micro Small.

Du et al., "Preparation of nanoporous nickel-copper sulfide on carbon cloth for high-performance hybrid supercapacitors", Article, 2018, p. 1-38, Electrochimica Acta.

Altschul et al., "Basic Local Alignment Search Tool", Article, 1990, p. 403-410, vol. 215, J. Mol. Biol.

Botella et al., "Surface-modified silica nanoparticles for tumor-targeted delivery of camptothecin and its biological evaluation", Article, 2011, p. 246-257, vol. 156, Journal of Controlled Release.

(56) References Cited

OTHER PUBLICATIONS

Cabrera et al., "Multifunctional Nanovesicle-Bioactive Conjugates Prepared by a One-Step Scalable Method Using CO2-Expanded Solvents", Article, 2013, p. 3766-3774, vol. 13, Nano Letters.

Cabrera et al., "α-Galactosidase-A-Loaded Nanoliposomes with Enhanced Enzymatic Activity and Intracellular Penetration", Article, 2016, p. 829-840, vol. 5, Advanced Healthcare Materials, Materials Views.

Corchero et al., "Integrated Approach to Produce a Recombinant, His-Tagged Human α-Galactosidase A in Mammalian Cells", Article, 2011, p. 1206-1217, vol. 27, No. 5, Biotechnol. Prog.

Cristobal-Lecina et al., "Synthesis of Stable Cholesteryl-Polyethylene Glycol-Peptide Conjugates with Non-Disperse Polyethylene Glycol Lengths", Article, 2020, p. 5508-5519, vol. 5, ACS Omega.

Dganit Danino, "Cryo-TEM of soft molecular assemblies", Article, 2012, p. 316-329, vol. 17, Current Opinion in Colloid & Interface Science.

Desnick et al., "Fabry's disease: Enzymatic diagnosis of hemizygotes and heterozygotes—α-Galactosidase activities in plasma, serum, urine, and leukocytes", Article, Feb. 1973, p. 157-171, vol. 81, No. 2, The Journal of Laboratory and Clinical Medicine.

Ferrer-Tasies et al., "Quatsomes: Vesicles Formed by Self-Assembly of Sterols and Quaternary Ammonium Surfactants", Article, 2013, p. 6519-6528, vol. 29, Langmuir.

Fervenza et al., "Safety and efficacy of enzyme replacement therapy in the nephropathy of Fabry disease", Article, 2008, p. 823-843, vol. 2, No. 4, Biologics: Targets & Therapy.

Giannotti et al., "Highly Versatile Polyelectrolyte Complexes for Improving the Enzyme Replacement Therapy of Lysosomal Storage Disorders", Article, 2016, p. 25741-25752, vol. 8, ACS Applied Materials & Interfaces.

Higgins et al., "Clustal V: improved software for multiple sequence alignment", Article, 1992, p. 189-191, vol. 8, No. 2, Cabios.

R. Hosemann and S.N. Bagchi, "Direct Analysis of Diffraction by Matter", Article, 1963, p. 568-569, vol. 142, No. 3592, Science.

Hsu et al., "Enhanced Endothelial Delivery and Biochemical Effects of α-Galactosidase by ICAM-1-Targeted Nanocarriers for Fabry Disease", Manuscript, Feb. 2011, p. 323-331, vol. 149, No. 3, J. Control Release.

Loannou et al., "Fabry Disease: Preclinical Studies Demonstrate the Effectiveness of α-Galactosidase A Replacement in Enzyme-Deficient Mice", Article, 2001, p. 14-25, vol. 68, Am. J. Hum. Genet.

Lee et al., "A biochemical and pharmacological comparison of enzyme replacement therapies for the glycolipid storage disorder Fabry disease", Article, 2003, p. 305-313, vol. 13, No. 4, Glycobiology.

Li et al., "Scatterless hybrid metal-single-crystal slit for small-angle X-ray scattering and high-resolution X-ray diffraction", Article, 2008, p. 1134-1139, vol. 41, Journal of Applied Crystallography.

Mayes et al., "Differential assay for lysosomal alpha-galactosidases in human tissues and its application to Fabry's disease", Article, 1981, p. 247-251, vol. 112, Clinica Chimica Acta.

Najafian et al., "Progressive podocyte injury and globotriaosylceramide (GL-3) accumulation in young patients with Fabry disease", Article, 2011, p. 663-670, vol. 79, Kidney International.

Ohshima et al., "α-Galactosidase A deficient mice: A model of Fabry disease", Article, Mar. 1997, p. 2540-2544, vol. 94, Medical Sciences, Proc. Natl. Acad. Sci.

Pabst et al., "Structural information from multilamellar liposomes at full hydration: Full q-range fitting with high quality x-ray data", Article, Sep. 2000, p. 4000-4009, vol. 62, No. 3, Physical Review E, The American Physical Society.

Pabst et al., "Structural analysis of weakly ordered membrane stacks", Article, 2003, p. 1378-1388, vol. 36, Journal of Applied Crystallography.

Jan Skov Pedersen, "A flux- and background-optimized version of the NanoSTAR small-angle X-ray scattering camera for solution scattering", Article, 2004, p. 369-380, vol. 37, Journal of Applied Crystallography.

Rafael et al., "Efficient EFGR mediated siRNA delivery to breast cancer cells by Cetuximab functionalized Pluronic® F127/Gelatin", Article, 2018, p. 81-93, vol. 340, Chemical Engineering Journal.

Schiffmann et al., "Screening, diagnosis, and management of patients with Fabry disease: conclusions from a "Kidney Disease: Improving Global Outcomes" (KDIGO) Controversies Conference", Meeting Report, 2017, p. 284-293, vol. 91, No. 2, Kidney International.

Schwamberger et al., "Combining SAXS and DLS for simultaneous measurements and time-resolved monitoring of nanoparticle synthesis", Article, 2015, p. 116-122, vol. 343, Nuclear Instruments and Methods in Physics Research B.

Shen et al., "Mannose receptor-mediated delivery of moss-made α-galactosidase A efficiently corrects enzyme deficiency in Fabry mice", Article, 2016, p. 293-303, vol. 39, No. 2, Journal of Inherit Metab. Dis.

Steiner et al., "The structure of the N-terminal module of the cell wall hydrolase RipA and its role in regulating catalytic activity", Article, 2018, p. 912-923, vol. 86, Wiley Proteins.

Miyoshi et al., "A detailed analysis of partial molecular volumes in DPPC/cholesterol binary bilayers", Article, 2014, p. 3069-3077, vol. 1838, Biochimica et Biophysica Acta.

Ventosa et al., "New technologies for the preparation of micro- and nanostructured materials with potential applications in drug delivery and clinical diagnostics", Article, 2006, p. 11-18, vol. 3, No. 1, Contributions to Science.

Sambrook J. et al, "Molecular Cloning a Laboratory Manual, Third Edition", Reference Manual, Chapter 16, 16.1-16.54, Cold Spring Harbor Laboratory Press <retrieved on Apr. 28, 2024> <https://www.scribd.com/document/532089634/Sambrook-Russel-Molecular-Cloning-A-Laboratory-Manual-Vol-1-2-3-CSHL-Press-3rd-Ed-2000>.

* cited by examiner

LIPOSOMES AND ITS USE FOR ENZYME DELIVERY

CROSS-REFERENCE TO RELATED APPLICATIONS AND PRIORITY

This patent application claims priority from PCT Application No. PCT/EP2022/051727 filed Jan. 26, 2022, which claims priority from European Patent Application No. 21382062.4 filed Jan. 27, 2021.

TECHNICAL FIELD

The present invention relates in general to the field of liposomes which are useful in the delivery of enzymes, in particular of the alpha-galactosidase enzyme. The present invention provides, among others, the liposomes, as well as a process for the preparation of these liposomes, and uses thereof in the treatment of diseases such as Fabry disease.

BACKGROUND ART

Certain diseases can be caused by the lack of activity of a particular protein or of a certain enzyme, either by being defective or absent, as in the case of lysosomal diseases, such as Fabry disease.

Fabry disease (FD) is a rare lysosomal storage disorder characterized by a deficiency or absence of α-galactosidase A (GLA), a lysosomal hydrolase. The missing GLA activity leads to the accumulation of its neutral glycosphingolipid substrates, mainly globotriaosylceramide (Gb3), within lysosomes of a wide variety of cell types including vascular endothelial cells, podocytes, cardiomyocytes, and nerve cells. In Fabry patients, Gb3 accumulation in kidney can start as early as 17 weeks of gestation and increases gradually, and directly correlates with early kidney damage and albuminuria (Najafian, B. et al., 2011). The Gb3 accumulation in renal cells and consequently the urinary loss of podocytes are previous to clinical manifestations (e.g., proteinuria), meaning that the cellular damage takes place before tissue damage becomes clinically evident (Schiffmann et al., 2017). Gb3 accumulation in other organs and the later development of clinical symptoms seems to follow the same trend also in other organs, including the heart (Hsu M. J., et al., 2019). In preclinical and clinical samples, Gb3 accumulation can be visualized or quantified using immunohistochemistry, thin layer chromatography, electronic microscopy and mass spectroscopy (MS).

The principal treatment of Fabry patients is enzyme replacement therapy (ERT), which relies on the intravenous infusion of exogenous recombinant GLA every other week. Currently, there are two GLA enzymes approved for ERT in FD: agalsidase beta (Fabrazyme®, Sanofi-Genzyme) and agalsidase alfa (Replagal®, Shire-Takeda) administered at 1 mg kg-1 and 0.2 mg kg-1, respectively. Fabrazyme® (produced in genetically engineered Chinese Hamster Ovary (CHO) cells) and Replagal® (produced in a human cell line) present comparable biochemical properties and no significant differences in the specific activity (Lee et al., 2003). Although both compounds reduce Gb3 accumulation in tissues, neither treatment seems to completely reverse the disease, especially in advanced stages (Fervenza, F. C., et al. 2008).

The enzyme replacement therapy administering naked GLA shows several drawbacks including poor biodistribution, short plasma half-life, limited efficacy, and relatively high immunogenicity in Fabry patients. An attractive strategy to overcome these problems is the use of nanocarriers for encapsulating the enzyme. Nanoliposomes functionalized with guiding ligands have already emerged to protect and deliver GLA to endothelial cells (for example, in Cabrera, I., et al. 2016), however, low colloidal stability and limited enzyme entrapment efficiency present a problem for the pharmaceutical development and the clinical translation of these nanoformulations.

From what it is known in the field, there is still a need to find a specific enzyme delivery method for diseases that use enzymes as therapeutic agent, such as Fabry disease, that efficiently entrap the enzyme and which improves enzymatic activity.

SUMMARY OF INVENTION

The inventors have developed a robust tool for α-galactosidase A (GLA) enzyme delivery, allowing the transported enzyme to perform its activity in vivo with high efficacy which is useful in the treatment of Fabry disease. This tool is based on liposomes, wherein each liposome (named herein also as a "hybrid-liposome" (HLP) or "nano-GLA" or "nanoGLA"), comprises:

- a) a phospholipid (e.g., dipalmitoylphosphatidylcholine (DPPC));
- b) cholesterol (chol);
- c) a conjugate comprising a cholesterol moiety, a polyethylene glycol (PEG) moiety and a peptide moiety comprising a RGD sequence, wherein the PEG moiety is covalently attached to the cholesterol moiety by one end via a bond of the type alkyl ether and is covalently attached to the peptide moiety comprising the RGD sequence by the other end;
- d) a non-lipid cationic surfactant present in a percentage of less than 30% mol in respect to the total mol of the components of the liposome a), b), c) and d) (that is, the phospholipids, chol, the conjugate and the non-lipid cationic surfactant); and,
- e) alpha-galactosidase enzyme present in a weight ratio of micrograms of GLA in respect to the total milligrams of the components of the liposome a), b), c) and d) (μg GLA/mg of the a), b), c) and d) components, (that is, of the phospholipids, chol, the conjugate and the non-lipid cationic surfactant) between and including 2 to 35.

The present invention provides comparative results with an already known liposomal system disclosed in Cabrera, I., et al. 2016 (see example 1) and also with the free enzyme Replagal® (see examples 2 for in vitro experiment and example 3 for in vivo experiment) with surprising results. In the present invention the GLA was exemplified with the human GLA wherein the monomers were of sequence SEQ ID NO: 1 both containing tags and tag free.

The comparison with the known liposomal system disclosed in Cabrera, I. et al. 2016 was performed as that liposomal system (named herein as "LP" or "LP-GLA" in example 1) was previously developed for GLA delivering and it was composed of the phospholipid DPPC, cholesterol, and an RGD unit (comprising the tripeptide Arg-Gly-Asp) linked to the cholesterol moiety (chol-PEG200-RGD) to favor the recognition of αvβ3-integrins, expressed in endothelial cells. Nevertheless, in the GLA-loaded liposomal system of Cabrera I., et al. 2016, the enzyme entrapment efficiency was around 40%, resulting in an insufficient drug concentration for achieving in vivo therapeutic doses (see FIG. 2).

Surprisingly, the incorporation of cationic myristalkonium chloride (MKC) surfactant in a concentration of less than 30% mol (in respect to the total mol of the components of the liposome a), b), c) and d)) to the liposomes of the present invention outperformed that previously known liposomes in terms of GLA entrapment (see FIG. 2), and/or GLA enzymatic activity in vitro (see FIG. 4). Moreover, the liposomes of the invention were safe. The fact that MKC in low concentration (less or equal to 30% mol in respect to the total mol of the components of the liposome a), b), c) and d)) surprisingly improved the GLA efficacy in vitro was unexpected taking into account that higher concentrations of MKC, for instance, a concentration of more or equal to 50% mol of MKC in other nanovesicles allowed to achieve the entrapment of the GLA (see FIG. 2) but abolished GLA enzymatic activity (see FIG. 4A).

The results obtained with the liposomes of the invention were due to a synergistic effect as can be seen in example 2. The ratio in weight between GLA and the components of the liposome a), b), c) and d), had a critical impact on physicochemical properties and stability of the liposomes of the invention (example 2.1). The liposomes wherein the GLA enzyme was present in a ratio of micrograms of GLA in respect to the total milligrams of the components of the liposome a), b), c) and d) (μg GLA/mg of the a), b), c) and d) components) of 30 performed with a 150% activity of that of Replagal® in vitro; whereas wherein that ratio was at least 36 the liposomes were not stable and their physicochemical properties were altered (see FIGS. 5A and 5B).

For in vivo experiments, surprisingly when the composition comprising the liposomes of the invention comprised glucose, sucrose or threalose, the GLA enzymatic activity was improved in comparison with other isosmotic solutions (see example 3 and FIGS. 6A and 6B), in particular, with glucose at 5% w/v. Moreover, the liposomes of the invention increased the GLA enzymatic activity levels in plasma over the free enzymes (Replagal® or a recombinant human GLA) (FIG. 7).

In vivo in a mice model of FD the liposomes of the invention DPPC:Col:(Chol-PEG400-RGD):MKC, wherein the MKC was at 5% mol in respect to the total mol of the components of the liposome a), b), c) and d), showed better results than the Replagal® and the free recombinant GLA in the reduction of Gb3 in several organs as a single dose (see FIG. 8) and as a repeated-dose (twice per week up to 8 doses) (see FIG. 9). Significantly, the liposome of the invention showed reduction of Gb3 in the brain both, as a single dose and after repeated administrations, which was not observed with the free enzyme (including Replagal®) (see FIG. 10).

From the data provided below, it is remarkable the fact that the liposomes of the present invention can be used as enzyme-replacement therapy system for treatment of Fabry disease.

Thus, a first aspect of the invention refers to a liposome comprising:

a) a phospholipid (e.g., dipalmitoylphosphatidylcholine (DPPC));

b) cholesterol (chol);

c) a conjugate comprising a cholesterol moiety, a polyethylene glycol (PEG) moiety and a peptide moiety comprising a RGD sequence, wherein the PEG moiety is covalently attached to the cholesterol moiety by one end via a bond of the type alkyl ether and is covalently attached to the peptide moiety comprising the RGD sequence by the other end;

d) a non-lipid cationic surfactant present in a percentage of less than 30% mol in respect to the total mol of the components of the liposome a), b), c) and d) (that is, the phospholipids, chol, the conjugate and the non-lipid cationic surfactant); and, e) alpha-galactosidase enzyme present in a ratio of micrograms of GLA in respect to the total milligrams of the components of the liposome a), b), c) and d) (μg GLA/mg of the a), b), c) and d) components, that is, of the phospholipids, chol, the conjugate and the non-lipid cationic surfactant) between and including 2 to 35.

A second aspect of the invention refers to a pharmaceutical composition comprising a therapeutically effective amount of the liposome of the first aspect of the invention together with pharmaceutically acceptable excipients or vehicles.

The liposome of the first aspect of the invention or the pharmaceutical composition of the second aspect of the invention can be used for the treatment of diseases that use the enzyme as defined in the first aspect of the invention as therapeutic agent, for example, for the treatment of human diseases as the Fabry disease.

A third aspect of the invention refers to the liposome of the first aspect of the invention or the pharmaceutical composition of the second aspect of the invention for use as a medicament.

A fourth aspect of the invention refers to the liposome of the first aspect of the invention or the pharmaceutical composition of the second aspect of the invention for use in the treatment of Fabry disease.

A fifth aspect of the invention refers to the use of the liposome of the first aspect of the invention as a bioimaging tool.

A sixth aspect of the invention refers to the liposome of the first aspect of the invention or the pharmaceutical composition of the second aspect of the invention as a delivery system for GLA enzyme replacement.

The preparation of the liposomes can be performed by the $CO_2$-based DELOS-SUSP methodology disclosed in WO2014001509 and Cabrera I, et al. 2013, which ensures a robustness and the reproducible scale up of the liposomes which allows the preparation of nanomedicines in sufficient quantities for both preclinical and clinical testing, followed by concentration and diafiltration (in any order) as explained herein.

A seventh aspect of the invention refers to a process for the production of the liposome of the first aspect of the invention comprising the following steps:

a) preparing an aqueous solution which comprises the GLA enzyme defined in the first aspect of the invention;

b) preparing a solution comprising the conjugate as defined in the first aspect of the invention, cholesterol and a phospholipid dissolved in an organic solvent, where the organic solution is expanded with a compressed fluid;

c) adding the non-lipid cationic surfactant defined in the first aspect of the invention either to the solution of the step a), or to the solution of the step b) before expanding this solution;

d) depressurizing the solution resulting from the step b) over the resulting solution of the step a); and e) diafiltrating and concentrating, in any order, the resulting solution obtained in step d).

An eighth aspect of the invention refers to a device comprising the liposome of the first aspect of the invention or the pharmaceutical composition of the second aspect of the invention.

DETAILED DESCRIPTION OF THE INVENTION

Figure 1:
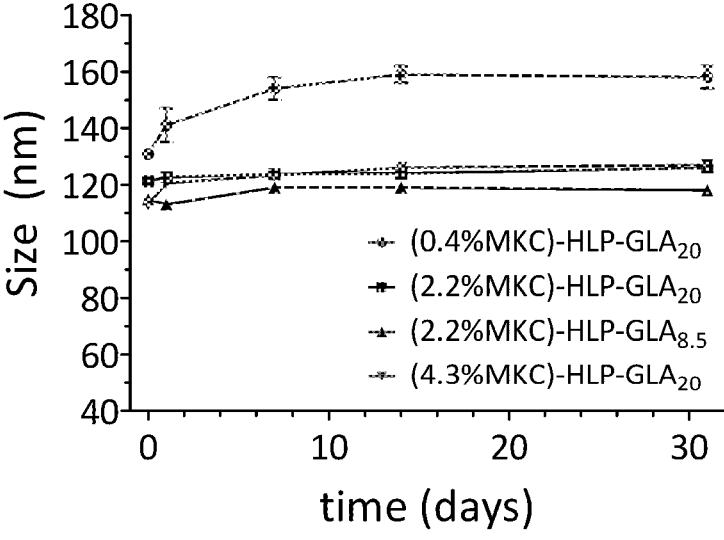
FIG. 1: shows the stability of HLP-GLA nanovesicles in terms of diameter size, PDI and ζ-potential measured as a function of time. Assay corresponds to a single representative experiment, replicated in three independent measurements.
Figure 1:
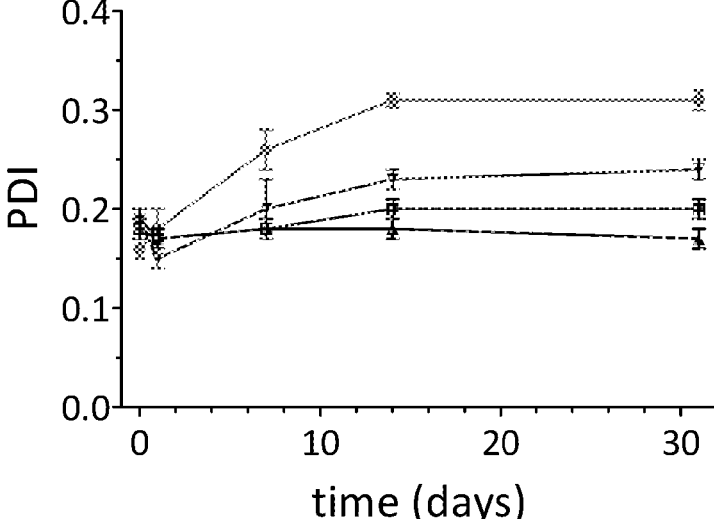
Figure 1:
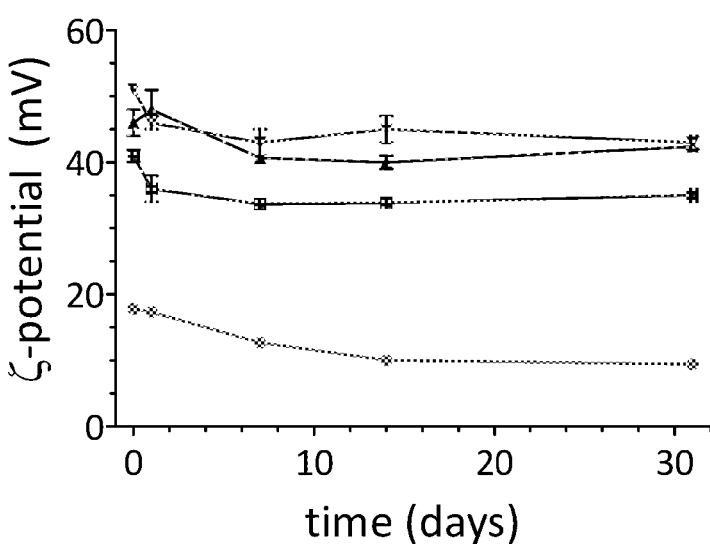

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For the purposes of the invention, any ranges given include both the lower and the upper end-points of the range. Ranges given should be considered approximate, unless specifically stated.

The first aspect of the invention refers to a liposome comprising a) a phospholipid, for example, dipalmitoylphosphatidylcholine (DPPC);

b) cholesterol (chol);

c) a conjugate comprising a cholesterol moiety, a polyethylene glycol (PEG) moiety and a peptide moiety comprising a RGD sequence, wherein the PEG moiety is covalently attached to the cholesterol moiety by one end via a bond of the type alkyl ether and is covalently attached to the peptide moiety comprising the RGD sequence by the other end (chol-PEG-RGD);

d) a non-lipid cationic surfactant present in a percentage of less than 30% mol (30 mol %) in respect to the total mol of the components of the liposome a), b), c) and d); (that is, the phospholipids, chol, the conjugate and the non-lipid cationic surfactant) and, e) alpha-galactosidase enzyme present in a ratio of micrograms of GLA in respect to the total milligrams of the components of the liposome a), b), c) and d) (μg GLA/mg of the a), b), c) and d) components) between and including 2 to 35.

The term "liposome" is to be understood as a self-assembling structure comprising one or more membranes comprised by lipid bilayers, each of which comprises two monolayers containing amphipathic lipid molecules oppositely oriented. Liposomes can have a single bilayer membrane (small unilamellar vesicles "SUVs" and large unilamellar vesicles "LUVs"), or multiple bilayer membrane (multilamellar large vesicles "MLVs").

The liposome membrane may include, without limitation, phospholipids such as dipalmitoylphosphatidylcholine (DPPC), phosphatidylcholine (PC), phosphatidylilserine (PS), phosphatidylethanolamine (PE), phosphatidylglycerol (PG), phosphatidylinositol (PI) and phosphatidic acid (PA).

In an embodiment of the first aspect of the invention, optionally in combination with any of the embodiments provided below, the phospholipid is dipalmitoylphosphatidylcholine (DPPC).

Cholesterol (Chol), CAS number: 57-88-5, is also known as Cholesten-3β-ol.

In an embodiment of the first aspect of the invention, optionally in combination with any of the embodiments provided above or below, the conjugate (c) is of formula cholesterol-(polyethylene glycol)-(peptide comprising a RGD sequence) (chol-PEG-RGD), wherein the PEG is covalently attached to the cholesterol by one end via a bond of the type alkyl ether and is covalently attached to the peptide comprising the RGD sequence by the other end via a carbamate bond.

The conjugate of the present invention can be obtained following the teachings of WO2014001509, or Cabrera, I. et al. 2013, or Cristobal-Lecina, E. et al. 2020, followed by a concentration and diafiltration step.

The liposome of the invention is also named herein as DPPC:Chol:(Chol-PEG-RGD):non-lipid cationic surfactant (e.g., DPPC:Chol:(Chol-PEG-RGD):MKC); in a particular embodiment is DPPC:Chol:(Chol-PEG400-RGD):MKC.

The RGD peptides (comprising the Arg-Gly-Asp motif) are peptides commonly described in the art as peptides that are able to interact with integrins present in the membrane of cells, and of particular interest for the study of cell adhesion, both between cells and between cells and different tissues or the basement membrane.

In an embodiment of the first aspect of the invention, optionally in combination with any of the embodiments provided above or below, the RGD peptide comprises (e.g., consists of) the sequence SEQ ID NO: 2 (RGDfK).

In the peptide with RGDfK sequence (SEQ ID NO: 2), the phenylalanine is the only D-amino acid (this is why it has been distinguished in the sequence with a lowercase letter), and wherein the covalent bond with the polyethylene glycol has been carried out functionalizing the lysine side-chain as described in WO2014001509.

In another embodiment of the first aspect of the invention, optionally in combination with any of the embodiments provided above or below, the RGD sequence is head-to-tail cycled SEQ ID NO 2 ("cRGDfK") as described in Cabrera, I., et al. 2013 and WO2014001509.

In another embodiment of the first aspect of the invention, optionally in combination with any of the embodiments provided above or below, the polyethilenglycol (PEG) molecular weight is between and including $PEG_{50}$ and $PEG_{600}$ (subscript referring to molecular weight), for example, is $PEG_{50}$, $PEG_{100}$, $PEG_{200}$, $PEG_{300}$, $PEG_{400}$, $PEG_{500}$, or $PEG_{600}$.

In an embodiment of the first aspect of the invention, optionally in combination with any of the embodiments provided above or below, the non-lipid cationic surfactant is present in a percentage of at least 0.1%, 0.2%, 0.3%, 0.4%, 0.5%, 1%, 1.5%, 2%, 2.1%, 2.2%, 2.3%, 2.4%, 2.5%, 3%, 3.5%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%; 7%, 8%, 9%, 10%, 11%, 12%; 13%; 14%, 15%; 16%; 17%, 18%, 19%; 20%, 21%, 22%, 23%, 24%, 25%, 26%, 27%, 28%, 29%, or 30% mol in respect to the total mol of the components of the liposome a), b), c) and d); or, in a percentage of less than 0.1%-30%, 0.1%-20%, 0.1%-15%, 0.4%-6%, 4%-6%, or 4.5-5.5% mol in respect to the total mol of the components of the liposome a), b), c) and d).

Non-lipid cationic surfactants include, but are not limited to, non-lipid cationic quaternary ammonium surfactants.

In an embodiment of the first aspect of the invention, optionally in combination with any of the embodiments provided above or below, the non-lipid cationic surfactants are non-lipid cationic quaternary ammonium surfactants.

In the present invention non-lipid quaternary ammonium surfactants refers to quaternary ammonium salts in which one nitrogen substituent is a long chain alkyl group. The non-lipid quaternary ammonium surfactants are water-soluble and self-assemble to form micelles above a critical micelle concentration (cmc). Conversely, the lipid quaternary ammonium surfactants self-assemble to form other structures, such as vesicles, planar bilayers or reverse micelles. The quaternary ammonium surfactants of the present invention are not lipids.

In an embodiment of the first aspect of the invention, optionally in combination with any of the embodiments provided above or below, the non-lipid cationic quaternary ammonium surfactant is selected from the list consisting of: myristalkonium chloride (MKC), cetyl trimethylammonium bromide (CTAB), cetylpyridinium chloride (CPC), benzalkonium chloride (BAC), cetyl trimethylammonium chloride (CTAC), benzethonium chloride (BZT), stearalkonium chloride, cetrimide, benzyldimethyldodecylammonium chloride, and combinations thereof.

In an embodiment of the first aspect of the invention, optionally in combination with any of the embodiments provided above or below, the non-lipid cationic quaternary ammonium surfactant is myristalkonium chloride (MKC) present in a percentage of less than 30% mol in respect to the total mol of the components of the liposome a), b), c) and d) (that is, the phospholipids, chol, the conjugate and the non-lipid cationic surfactant), e.g., MKC is present in a percentage of at least 0.1%, 0.2%, 0.3%, 0.4%, 0.5%, 1%, 1.5%, 2%, 2.1%, 2.2%, 2.3%, 2.4%, 2.5%, 3%, 3.5%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%; 7%, 8%, 9%, 10%, 11%, 12%; 13%, 14%, 15%; 16%; 17%, 18%, 19%; 20%, 21%, 22%, 23%, 24%, 25%, 26%, 27%, 28%, 29%, or 30% mol in respect to the total mol of the components of the liposome a), b), c) and d); or, in a percentage of less than 0.1%-30%, 0.1%-20%, 0.1%-15%, 0.4%-6%, 4%-6%, or 4.5-5.5% mol in respect to the total mol of the components of the liposome a), b), c) and d).

Myristalkonium chloride (MKC), CAS number 139-08-2, is also known as benzyldimethyltetradecylammonium chloride or myristyldimethylbenzylammonium chloride or N-benzyl-N-tetradecyldimethylammonium chloride or N, N-dimethyl-N-tetradecylbenzenemethanaminium chloride or tetradecylbenzyldimethylammonium chloride.

In an embodiment of the first aspect of the invention, optionally in combination with any of the embodiments provided above or below, the mol ratio of the DPPC: cholesterol:chol-PEG-RGD is 10:6.5:0.5, e.g., DPPC:cholesterol:chol-PEG400-RGD wherein the RGD is cyclic SEQ ID NO: 2 (for example, the RGD peptide as described in in Cabrera, I., et al. 2013 and WO2014001509 (thus, the chol-PEG-RGD represents the 3% mol in respect of the components)).

The term "alpha-galactosidase" (also named as alpha-galactosidase A or galactosidase alpha) (GLA for short) as used herein, refers to the glycoside hydrolase enzyme that hydrolyses the terminal alpha-galactosyl moieties from glycolipids and glycoproteins. It is encoded by the GLA gene (e.g., GenBank® Gene ID: 2717 at 13 Dec. 2020, DNA>NC_000023.11:c101407925-101397803 *Homo sapiens* chromosome X, GRCh38.p13 Primary Assembly; UniProt number P06280). It predominantly hydrolyzes ceramide trihexoside, and it can catalyze the hydrolysis of melibiose into galactose and glucose. As it is here understood, GLA can mean an alpha-galactosidase cloned and expressed both in procariotes and eucariotes.

In an embodiment of the first aspect of the invention, optionally in combination with any of the embodiments provided above or below, the GLA (also named herein as "the enzyme") of the present invention is the human GLA (EC 3.2.1.22), which is a homodimeric enzyme with a monomer weight of 48.8 kDa, so the whole GLA shows an approximated molecular weight of 100 KDa; or, alternatively, an enzyme with at least 85% sequence identity with SEQ ID NO: 1 and which retains its enzymatic activity. In an example, the GLA of the present invention does not comprise a tag, such as, for example, a histag or cmyctag. In yet another example, the GLA of the present invention is the enzyme GLA comprises at least one tag, for example, a histag or cmyctag.

In an embodiment of the first aspect of the invention, optionally in combination with any of the embodiments provided above or below, the enzyme is a dimer comprising (e.g., consisting of) in two monomers of sequence SEQ ID NO: 1.

In an embodiment of the first aspect of the invention, optionally in combination with any of the embodiments provided above or below, the enzyme is the GLAcmycHis which amino acid sequence is disclosed in Corchero J I et al., 2011.

In an embodiment of the first aspect of the invention, optionally in combination with any of the embodiments provided above or below, the alpha-galactosidase enzyme is present in a ratio of micrograms of GLA in respect to the total milligrams of the components of the liposome a), b), c) and d) (μg GLA/mg of the a), b), c) and d) components) between and including 2 to 35, 2 to 34, 2 to 33, 2 to 32, 2 to 31, 2 to 30, 10 to 35, 14 to 35, 14 to 33, 14 to 30, 15 to 35, 15 to 34, 15 to 33, 15 to 32, 15 to 31, 15 to 30, 20 to 35, 20 to 34, 20 to 33, 20 to 32, 20 to 31, 20 to 30; or, in another embodiment is present in a ratio of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 (μg GLA/mg of the a), b), c) and d) components).

In an embodiment of the first aspect of the invention, optionally in combination with any of the embodiments provided below, the liposome comprises a) a phospholipid, for example, dipalmitoylphosphatidyl-choline (DPPC);

b) cholesterol (chol);

c) a conjugate comprising a cholesterol moiety, a polyethylene glycol (PEG) moiety and a peptide moiety comprising a RGD sequence, wherein the PEG moiety is covalently attached to the cholesterol moiety by one end via a bond of the type alkyl ether and is covalently attached to the peptide moiety comprising the RGD sequence by the other end (chol-PEG-RGD) (e.g., the RGD sequence is head-to-tail cycled SEQ ID NO 2 ("cRGDfK");

d) a non-lipid cationic surfactant present in a percentage of less than 30% mol in respect to the total mol of the liposome components (that is, the phospholipids, chol, the conjugate and the non-lipid cationic surfactant) (e.g., at least 0.1%, 0.5%, 1%, 1.5%, 2%, 2.5%, 3%, 3.5%, 4%, 4.5%, 5%, 5.1%, 5.2%, 5.3%, 5.4%, 5.5%, 6%; or, in a percentage of less than 0.1%-30%, 0.1%-20%, 0.1%-15%, 0.4%-6%, or 4.5-5.5%); and, e) alpha-galactosidase enzyme present in a ratio of micrograms of GLA in respect to the total milligrams of the components of the liposome a), b), c) and d) (μg GLA/mg of the a), b), c) and d) components) between and including 2 to 35, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35; wherein each of its monomers is of sequence SEQ ID NO: 1 or of sequence with at least 85% of sequence identity (e.g., 85, 86, 87, 88, 89, 90, 91, 92, 93, 94, 95, 96, 97, 98, 99, or 100 percent sequence identity) with SEQ ID NO: 1.

In the present invention the term "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=[number of identical positions/total number of positions]×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410.

For multiple sequence analysis, the CLUSTAL W program can be used. The CLUSTAL W program desirably is run using "dynamic" (versus "fast") settings. Amino acid sequences are evaluated using a variable set of BLOSUM matrixes depending on the level of identity between the sequences. The CLUSTAL W program and underlying principles of operation are further described in, e.g., Higgins et al., "CLUSTAL V: improved software for multiple sequence alignment", 1992, CABIOS, 8(2), pages 189-191.

In an embodiment of the first aspect of the invention, optionally in combination with any of the embodiments provided above or below, the enzyme (the GLA of the present invention) is obtained recombinantlly from Chinese Hamster Ovary (CHO) cell culture, for example, following standard cell culture techniques (e.g., stable expression-based production method), for example as described in Sambrook J. et al. Molecular Cloning a Laboratory Manual, Third Edition. Cold Spring Harbor Laboratory Press. Chapter 16, 16.1-16-54.

In an embodiment of the first aspect of the invention, optionally in combination with any of the embodiments provided above or below, the GLA enzyme is Fabrazyme®; or alternatively, biosimilars from Fabrazyme®; or, alternatively, Replagal® or its biosimilars.

In an embodiment of the first aspect of the invention, optionally in combination with any of the embodiments provided above or below, the liposome comprises:

a) a phospholipid which is DPPC;

b) cholesterol (chol);

c) a conjugate comprising a cholesterol moiety, a polyethylene glycol (PEG) moiety and a peptide moiety comprising a RGD sequence, wherein the PEG moiety is PEG400 and is covalently attached to the cholesterol moiety by one end via a bond of the type alkyl ether and is covalently attached to the peptide moiety comprising the RGD sequence by the other end via a carbamate bond, wherein the RGD peptide is of sequence SEQ ID NO: 2 (e.g. cyclic, e.g., cRGDfK);

d) a non-lipid cationic surfactant which is MKC present in a percentage of less than 30% (e.g., at least 0.1%, 0.5%, 1%, 1.5%, 2%, 2.5%, 3%, 3.5%, 4%, 4.5%, 5%, 5.1%, 5.2%, 5.3%, 5.4%, 5.5%, 6%) mol percent in respect to the total mol of liposome components a), b), c) and d) (that is, the phospholipids, chol, the conjugate and the MKC); and, e) alpha-galactosidase enzyme as defined in the first aspect of the invention wherein each of its monomer is of sequence SEQ ID NO: 1.

In another embodiment of the first aspect of the invention, optionally in combination with any of the embodiments provided below, the liposome comprises:

a) dipalmitoylphosphatidylcholine (DPPC);

b) cholesterol (chol);

c) a conjugate comprising a cholesterol moiety, a polyethylene glycol (PEG400) moiety and a peptide moiety comprising a RGD sequence, eg. SEQ ID NO: 2 (e.g., cRGDfK), wherein the PEG400 moiety is covalently attached to the cholesterol moiety by one end via a bond of the type alkyl ether and is covalently attached to the peptide moiety comprising the RGD sequence by the other end (chol-PEG-RGD);

d) a non-lipid cationic surfactant which is MKC present in a percentage of about 5% mol (e.g., 4.5-5.5%) in respect to the total mol of the liposome components (that is, the phospholipids, chol, the conjugate and the MKC); and, e) alpha-galactosidase enzyme present in a ratio of micrograms of GLA in respect to the total milligrams of the components of the liposome a), b), c) and d) components) between and including 20 to 35, in an embodiment the ratio is 30; wherein each of its monomer is of sequence SEQ ID NO: 1 or of sequence with at least 85% of sequence identity (e.g. 85, 86, 87, 88, 89, 90, 91, 92, 93, 94, 95, 96, 97, 98, 99, or 100 percent sequence identity) with SEQ ID NO: 1, e.g., the GLA is obtained in CHO cells;

wherein the mol ratio of the DPPC:cholesterol:chol-PEG-RGD is 10:6.5:0.5.

In an embodiment of the first aspect of the invention, optionally in combination with any of the embodiments provided above or below, the enzyme in the present invention is integrated in the liposomes in a non-covalent manner.

In an embodiment of the first aspect of the invention, optionally in combination with any of the embodiments provided above or below, the enzyme (the GLA of the present invention) is inside the liposome; or, alternatively, outside the liposome; or, alternatively, the enzyme traverses the liposome.

In an embodiment of the first aspect of the invention, optionally in combination with any of the embodiments provided above or below, the liposome is spherical, unilamellar, homogeneous in size and stable.

There are well-known methods in the state of the art to characterize the liposomes of the invention, for example by means of their $\zeta$-potential. The size of the nanovehicle can be measured by any method known to the expert, for example by dynamic light scattering (DLS), mass spectrometry, Small-angle X-ray scattering (SAXS), transmission electron microscopy (TEM) or high resolution transmission electron microscopy (HR-TEM). The stability of the liposomes of the present invention can be measured by dynamic light scattering (DLS).

In an embodiment of the first aspect of the invention, optionally in combination with any of the embodiments provided above or below, the liposome has a mean diameter of less than 300 nm; for example, 20-300 nm; for example, between 80-200 nm; or, for example, between 100-160 nm, e.g., between 120-155 nm, e.g. measured by dynamic light scattering (DLS).

The term "homogeneous size" refers to a liposome with a polydispersity index (PDI) of 0.05-0.40, for example between 0.05-0.30, or, e.g. 0.05-0.2.

In an embodiment of the first aspect of the invention, optionally in combination with any of the embodiments provided above or below, the liposome has a $\zeta$-potential of 20-65 mV, e.g., 30-50 mV, or, e.g., 35-50 mV.

In an embodiment of the first aspect of the invention, optionally in combination with any of the embodiments provided above or below, the liposomes are spherical with a mean diameter of 100-160 nm, unilamellar, with a PDI of 0.05-0.3, a $\zeta$-potential of 20-65 mV and they are stable in dispersion at least to 2 months; e.g., the liposomes are spherical with a mean diameter of 120-155 nm, unilamellar, with a PDI of 0.05-0.2, a $\zeta$-potential of 35-50 mV and they are stable in dispersion at least to 2 months.

In an embodiment of the first aspect of the invention, optionally in combination with any of the embodiments provided above or below, the liposome is further bound to an element selected from the group consisting of: a fluorophore, a radiopharmaceutical, a peptide, a polymer, an inorganic molecule, a lipid, a monosaccharide, an oligosaccharide, an antibody or fragment of an antibody, an antigen, and any combination thereof.

A second aspect of the invention refers to a pharmaceutical composition comprising a therapeutically effective amount of the liposome of the first aspect of the invention, together with pharmaceutically acceptable excipient or carriers, or vehicles.

The expression "therapeutically effective amount" as used herein, refers to the amount of a compound (i.e., the liposome of the invention) that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The expression "pharmaceutically acceptable excipients or carriers, or vehicles" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

In an embodiment of the second aspect of the invention, optionally in combination with any of the embodiments provided above or below, the pharmaceutical composition comprising a therapeutically effective amount of the liposome of the first aspect of the invention, comprising glucose, sucrose or threalose in an amount from 2 to 15% (2%, 3%, 4%, 5%, 6%, 7%, 8%, 9%, 10%, 11%, 12%, 13%, 14%, 15%; e.g., from 2% to 10%, from 2% to 8%, or from 2 to 5%, e.g., is 5%) in weight with respect to the total volume of the composition (% w/v) together with pharmaceutically acceptable excipient or vehicles.

In an embodiment of the second aspect of the invention, optionally in combination with any of the embodiments provided above or below, the pharmaceutical composition comprises glucose in an amount from 2 to 15% (2%, 3%, 4%, 5%, 6%, 7%, 8%, 9%, 10%, 11%, 12%, 13%, 14%, 15%; e.g., from 2% to 10%, from 2% to 8%, or from 2 to 5%, e.g., is 5%) in weight with respect to the total volume of the composition together with pharmaceutically acceptable excipient or vehicles.

In an embodiment of the second aspect of the invention, optionally in combination with any of the embodiments provided above or below, the pharmaceutical composition comprises glucose in an amount of 5% in weight with respect to the total volume of the composition together with pharmaceutically acceptable excipient or vehicles.

In an embodiment of the second aspect of the invention, optionally in combination with any of the embodiments provided above or below, the pharmaceutical composition comprises the GLA enzyme in an amount of at least 0.1 mg/mL (mg per mL of the pharmaceutical composition), e.g., at least 0.2 mg/mL, in another example, at least 0.225 mg/mL, or at least 0.271 mg/mL, or at least 0.35 mg/mL.

A third aspect of the invention refers to the liposome of the first aspect of the invention or the pharmaceutical composition of the second aspect of the invention for use as a medicament.

The third aspect of the invention can be reformulated as the use of the liposome of the first aspect of the invention or the pharmaceutical composition of the second aspect of the invention for the manufacture of a medicament.

A fourth aspect of the invention refers to the liposome of the first aspect of the invention or the pharmaceutical composition of the second aspect of the invention for use in the treatment of Fabry disease.

The fourth aspect of the invention can be reformulated as the use of the liposome of the first aspect of the invention or the pharmaceutical composition of the second aspect of the invention for the manufacture of a drug for the treatment of Fabry disease. It can also be reformulated as a method for the treatment or prevention of Fabry disease, that involves administering a therapeutically effective amount of the first aspect of the invention's liposome, together with pharmaceutically acceptable carriers or excipients, to a subject in need of it, including a human.

The medicament can be presented in a form adapted for parenteral, cutaneous, oral, epidural, sublingual, nasal, intrathecal, bronchial, lymphatic, rectal, transdermal or inhaled administration. The form adapted to parenteral administration refers to a physical state that can allow its injectable administration, that is, preferably in a liquid state.

Parenteral administration can be carried out by intramuscular, intraarterial, intravenous, intradermal, subcutaneous or intraosseous administration, but not limited to these types of parenteral routes of administration. The form adapted to oral administration is selected from the list comprising, but not limited to, drops, syrup, tisane, elixir, suspension, extemporaneous suspension, drinkable vial, tablet, capsule, granulate, stamp, pill, tablet, lozenge, troche or lyophilized. The form adapted to rectal administration is selected from the list comprising, but not limited to, suppository, rectal capsule, rectal dispersion or rectal ointment. The form adapted to the transdermal administration is selected from the list comprising, but not limited to, transdermal patch or iontophoresis.

In an embodiment of the third and fourth aspects of the invention, optionally in combination with any of the embodiments provided above or below, the medicament is presented in a form adapted for intravenous administration.

In an embodiment of the third and fourth aspect of the invention, optionally in combination with any of the embodiments provided above or below, the medicament is administered repeatedly; for example, at least once every week, in yet another example, at least once every two weeks, e.g., until symptoms reverse or, alternatively, during the whole life of the patient (life-long).

In an embodiment of the third and fourth aspects of the invention, optionally in combination with any of the embodiments provided above or below, at least 0.20 mg, 0.25 mg, 0.5 mg, 0.75 mg, 1 mg, 1.5 mg, 2 mg, 2.5 mg of the GLA is administered per Kg of the subject suffering Fabry disease to said subject every other week.

The liposomes of the present invention can be labelled, for example with a dye; and functionalized with targeting ligand for site-specific labelling; and finally deliver the enzyme.

Thus, a fifth aspect of the invention refers to the use of the liposome of the first aspect of the invention as a bioimaging tool.

In an embodiment of the fifth aspect of the invention, optionally in combination with any of the embodiments provided above or below, it is used as a bioimaging tool, to track the enzyme internalization and delivery.

As "bioimaging tool" is to be understood according to this description a reagent used in an imaging technique used in biology to trace some compartments of cells or particular tissues. Examples of bioimaging tools include chemiluminescent compounds, fluorescent and phosphorescent compounds, X-ray or alpha, beta, or gamma-ray emitting compounds, etc.

A sixth aspect of the invention refers to the liposome of the first aspect of the invention or the pharmaceutical composition of the second aspect of the invention as a delivery system for GLA enzyme replacement.

The liposome of the first aspect of the invention can be formed by different techniques, such as ultrasonication (US), thin film hydration (THF) and a one-step scalable method using $CO_2$ expanded solvents called Depressurization of an Expanded Liquid Organic Solution-suspension (DELOS-SUSP) (e.g., as disclosed in WO2014001509; or EP1843836 following concentration and diafiltration).

A seventh aspect of the invention refers to a process for the production of the liposome of the first aspect of the invention comprising the following steps:
  a) preparing an aqueous solution which comprises the GLA enzyme defined in the first aspect of the invention;
  b) preparing a solution comprising the conjugate as defined in the first aspect of the invention, cholesterol and a phospholipid dissolved in an organic solvent where the organic solution is expanded with a compressed fluid;

c) adding the non-lipid cationic surfactant defined in the first aspect of the invention either to the solution of the step a), or to the solution of the step b) before expanding this solution;

d) depressurizing the solution resulting from the step b) over the resulting solution of the step a);

e) diafiltrating and concentrating, in any order, the resulting solution obtained in step d).

In an embodiment of the seventh aspect of the invention, optionally in combination with any of the embodiments provided above or below, the aqueous solution of step (a) can also contain buffers, salts, sugars and/or other excipients.

The diafiltration steps can be performed by, for example, the KrosFlo® Research IIi TFF diafiltration system (KR2i), for example, following the procedure already described in Cabrera, I., et al. 2016, e.g., with certain modifications, such as lowering the diafiltration cycles to 4 or 5; the concentration steps can be performed by, for example, the same equipment, with the following modifications:

a) the order of the diafiltration and concentration process is interchangeable: diafiltration and concentration, or concentration and diafiltration;

b) operation flow rate (provided by pump) can be from 20 to 200 mL/min;

c) operation TMP (transmembrane pressure) can be from 2.5 to 10 psi;

d) hollow fiber filter columns can be from 13 to 235 cm2 of Modified Polyethersulfone (mPES) and 300 kDa, depending on the working volume scale; and/or e) reservoirs from commercial provider can be replaced for glass flasks depending on the process volume.

For example, in order to perform the concentration, a volume between 10 and 5000 mL can be added to the sample container, which is only connected to the column. In this case, the sample will become more concentrated as volume is being removed. The degree of concentration (Concentration Factor, CF) corresponds to the initial volume (Vi) divided into the final volume (Vf), CF=Vi/Vf. For example, if the initial volume is 50 mL and the desired CF is 5, then the process will stop when sample volume in the sample container is 10 mL. The time for the completion of the process depends on the total volume processed and the operation parameters and the expert in the field knows how to adjust it.

In an embodiment of the seventh aspect of the invention, optionally in combination with any of the embodiments provided above or below, the diafiltration and concentration steps are performed in an aqueous solution, for example water or an isosmotic solution, in order to the elimination of the non-incorporated GLA and the organic solvents from the dispersion.

In an embodiment of the seventh aspect of the invention, optionally in combination with any of the embodiments provided above or below, the diafiltration and concentration steps are performed in an aqueous solution comprising sucrose, glucose or trehalose in 2-15% w/v, for example sucrose 10%, glucose 5% or trehalose 10% w/v, for example, glucose 5% w/v.

In an embodiment of the seventh aspect of the invention, optionally in combination with any of the embodiments provided above or below, the diafiltration is performed at least 3 times, for example 3, 4, 5, 6 or 7 times, in another example is at least 4 times, for example 4, 5, 6, 7, 8, 9, 10, 11 or 12 times, to allow solvent change.

Another aspect of the present invention is also the liposome obtainable by the method of the seventh aspect of the invention.

Also part of the invention is a process for the production of the liposome of the first aspect of the invention by self-assembling of the phospholipid, cholesterol, the conjugate of the first aspect of the invention and the non-lipid cationic surfactant of the first aspect of the invention (e.g., DPPC, Chol, the conjugate Chol-PEG-RGD and MKC) and following GLA entrapment (the GLA of the first aspect of the invention), for example, by adsorbing the GLA in the surface of the liposome. Also part of the invention is the liposomes obtainable by this process of production.

An eighth aspect of the present invention refers to a kit (kit of parts) comprising the liposome of the first aspect of the invention or the pharmaceutical composition of the second aspect of the invention, which optionally can comprise instructions for the delivery of the enzyme comprised in the liposome of the first aspect of the invention or the pharmaceutical composition of the second aspect of the invention (from now on, "the kit of the invention"). Optionally the kit may additionally comprise further means to visualize the liposome of the invention.

Also part of the invention is the use of the kit of the invention for the uses described in any of the aspects of the present invention.

Also part of the invention is a device for the release of the liposome of the first aspect of the invention or the pharmaceutical composition of the second aspect of the invention comprising them.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Example 1. Nanovesicles and their Performance in GLA Enzyme Intracellular Delivery Different RGD-targeted nanovesicles were obtained and their performance in intracellular delivery of GLA (using Repalgal® as the GLA included in the nanovesicles) was compared: (i) a liposomal system (named herein as "LP") containing a recombinant GLA already known, which was composed of the phospholipid DPPC, cholesterol, and an RGD unit (tripeptide Arg-Gly-Asp) linked to the cholesterol moiety (chol-PEG200-RGD) described in Cabrera, I., et al. 2016 wherein the RGD peptide was cyclic cRGDfk; (ii) nanovesicles containing the quaternary ammonium surfactant miristalkonium chloride (MKC) in high amount (>50 mol % of the total membrane components, "h-MKC"), known as "quatsomes" (Ferrer-Tasies, L. et al. 2013) (named herein as "MQ"); and (iii) liposomes with various concentrations of a cationic surfactant (exemplified by MKC) in their membrane, named herein as "hybrid-liposomes" ("HLP") comprising low MKC (<5 mol % of the total membrane components, "I-MKC") amounts. All were obtained using the DELOS-SUSP method, based on the use of compressed $CO_2$, as described in WO2006/079889, which allowed the preparation of nanovesicles with high batch-to-batch consistency and easy scalability, in comparison to other nanovesicle processing techniques (Cabrera, I., et al. 2016).

Materials and Methods

Materials: Cholest-5-en-3, #-ol (cholesterol; purity 95%) was purchased from Panreac (Barcelona, Spain). 1,2-Di-palmitoyl-sn-glycero-3-phosphocholine (DPPC) was obtained from CordenPharma (Plankstadt, Germany). Miristalkonium chloride (MKC) was purchased from US Biological (Salem, United States). Cholesterol-PEG200-RGD was prepared as described previously in Cabrera, I., et al. 2013 or from Cristóbal-Lecina, E., et al. 2020 (wherein the PEG moiety was covalently attached to the cholesterol moiety by one end via a bond of the type alkyl ether and was covalently attached to the peptide moiety comprising the RGD sequence by the other end via a bond of the type carbamate). The GLA enzyme was exemplified by the Agalsidase alfa (GLA, 1 mg mL-1, Replagal®) purchased from Shire-Takeda (which was a tag-free enzyme). Ethanol HPLC grade (Teknocroma Sant Cugat del Vallès, Spain) was purchased with high purity and used without further purifications. Dimethyl sulfoxide (DMSO, ACS reagent, purity 99.9%) was obtained from Sigma-Aldrich (Madrid, Spain). Carbon dioxide (purity 99.9%) was supplied by Carburos Metálicos S.A. (Barcelona, Spain). The water used was pre-treated with a MilliQ Advantage A10 water purification system (Millipore Ibérica, Madrid, Spain).

Preparation of nanovesicles: All formulations were prepared using the same preparative route with the DELOS-SUSP methodology as described in Cabrera, I., et al. 2013, Ventosa, N., et al. 2005 and WO2006/079889 followed by a concentration step.

In all cases (LP, MQ and HLP) the RGD peptide was the head-to-tail cycled SEQ ID NO 2 ("cRGDfK") disclosed in Cabrera, I., et al. 2013 and 2016 and the conjugate was obtained as described in the same document, as described in Cabrera, I., et al. 2013.

Quatsomes (MQ and MQ-GLA) preparation: For GLA unloaded-quatsomes (MQ), chol-PEG200-RGD was dissolved in DMSO before adding dropwise an ethanolic solution of cholesterol and MKC, obtaining a solution with DMSO and EtOH in 2:5 volume ratio. The mixture was loaded into a 25 mL high-pressure vessel and volumetrically expanded with compressed $CO_2$ to reach a working pressure (Pw) of 10 MPa. The system was kept at 308 K and 10 MPa for approximately 15 minutes to achieve a complete homogenization and thermal equilibration. For GLA-loaded quatsomes (MQ-GLA), GLA was added to water for injection (type I) to reach the desired final enzyme concentration (20 µg mL-1). To form the nanovesicles, the expanded organic phase was depressurized over the cold aqueous solution. In this step, a flow of N2 at the working pressure was used as a plunger to push down the $CO_2$-expanded solution from the vessel and to maintain a constant pressure of 11 MPa inside the vessel during depressurization. Dispersions of nanovesicles in a total concentration of 3.6 mg mL-1 (detailed final molar concentration of each component was 0.35, 2.59 and 5.87 µmol mL-1 for chol-PEG200-RGD, cholesterol, and MKC, respectively) in an aqueous media containing low amounts of DMSO and EtOH (3% and 7% v/v, respectively) were obtained and stored at 4° C. until characterization.

Liposomes (LP and LP-GLA) preparation: Liposomes (LP) were prepared following the described procedure procedure in Cabrera, I., et al. 2016 with slight modifications. Briefly, chol-PEG200-RGD was dissolved in DMSO before adding dropwise an ethanolic solution of cholesterol and DPPC, obtaining a solution with DMSO and EtOH in a 1:5 volume ratio. The mixture was loaded into a 25 mL high-pressure vessel and volumetrically expanded with compressed $CO_2$ to reach a working pressure of 10 MPa. The system was kept at 308 K and 10 MPa for approximately 15 minutes to achieve a complete homogenization and thermal equilibration. For GLA-loaded liposomes (LP-GLA$_{20}$), GLA was diluted in water for injection (type I) to reach the desired final enzyme concentration (20 µg mL-1). To form the nanovesicles, the expanded organic phase was depressurized over the aqueous solution at room temperature. The next steps followed the same order as for quatsomes preparation. Dispersions of nanovesicles in a total concentration of 1.5 mg mL-1 (detailed final molar concentration of each component was 0.10, 0.91 and 1.45 µmol mL-1 for chol-PEG200-RGD, cholesterol, and DPPC, respectively) in an aqueous media containing low amounts of DMSO and EtOH (0.8% and 4% v/v, respectively) were obtained and stored at 4° C. until characterization.

Hybrid-liposomes (HLP and HLP-GLA) preparation: For the preparation of hybrid-liposomes, a similar preparative route to that for liposomes was used. MKC (0.4, 2.2, or 4.3 mol % of the total moles of membrane components) was incorporated to the ethanolic solution before loading into the reactor. Next steps followed the same order as for liposomes preparation, obtaining (0.4% MKC)-HLP, (2.2% MKC)-HLP, and (4.3% MKC)-HLP systems. For GLA-loaded hybrid-liposomes, as it was described previously, GLA was diluted in water for injection (type I) to reach the final enzyme concentration: 20 µg mL$^{-1}$ for (0.4% MKC)-HLP-GLA$_{20}$, (2.2% MKC)-HLP-GLA$_{20}$, and (4.3% MKC)-HLP-GLA$_{20}$, and 8.5 µg mL$^{-1}$ for (2.2% MKC)-HLP-GLA$_{8.5}$. Hybrid-liposomes in a total lipid concentration of 1.5 mg mL$^{-1}$ (detailed final molar concentration of each component was 0.10, 0.91, and 1.45 µmol mL$^{-1}$ for chol-PEG200-RGD, cholesterol, and DPPC, respectively, and 0.01, 0.06, or 0.11 µmol mL$^{-1}$ of MKC for (0.4% MKC)-HLP, (2.2% MKC)-HLP, or (4.3% MKC)-HLP, respectively) in an aqueous media containing low amounts of DMSO and EtOH, 0.8% and 4% v/v, were obtained and stored at 4° C. until characterization.

Diafiltration and concentration: The non-conjugated GLA enzyme was separated from the GLA loaded liposomes using the KrosFlo® Research Ili TFF diafiltration system (KR2i) following the procedure already described in Cabrera, I., et al. 2016 with the modifications detailed herein, such as a concentration step explained herein.

Briefly, to separate the free GLA (~100 kDa) a 300 kDa cut-off mPES hollow fiber column was used. For each GLA-containing formulation, 10 mL of the nanovesicle dispersion was submitted to 6 cycles of diafiltration with cold pure water for injection (type I) (60 mL) resulting in the elimination of non-incorporated GLA and the organic solvents from the dispersion.

In order to reach the dose for in vivo testing, the (2.2% MKC)-HLP hybrid-liposome system was concentrated using the KrosFlo® Research Ili TFF diafiltration system (KR2i) with a 300 kDa cut-off mPES filter column. An initial volume of 74 mL was submitted to a concentration factor of ×12, resulting in 6 mL of the final nanoformulation. Three independent batches were produced following the same procedure to ensure the administration of a fresh formulation throughout the in vivo study, with no significant difference in physicochemical properties (see below).

In order to concentrate the samples (2.2% MKC)-HLP hybrid-liposome for in vivo testing), it was used the same process specified for the diafiltration, with the exception that in this case, the buffer reservoir was not connected to the system. This allowed the sample to became more concentrated as volume was being removed. The degree of concentration (Concentration Factor, CF) corresponded to the initial volume (Vi) divided into the final volume (Vf), CF=Vi/Vf; for in vivo toxicology, sample was concentrated with a CF of 12. Physicochemical characteristics (size, PDI and ζ-potential) of the liposomal system were determined by DLS after the concentration step, in order to ensure that the procedure itself had no relevant impact. No significant changes were observed after concentration in terms of size (p=0.169), PDI (p=0.903) and ζ-potential (p=0.116), since liposomes maintained a nanoscopic size (below 250 nm) and low polydispersity (PDI<0.35). Statistics were done by two-sample t-test using Minitab®17 statistical software (2013). Morphology was also inspected by cryoTEM imaging. Images showed spherical and mostly unilamellar vesicles, with the size in the nanometric range.

Size, polydispersity index and ζ-potential characterization: The size, polydispersity index (PDI) and ζ-potential of all the vesicles produced were measured using a dynamic light scattering (DLS) and electrophoretic light scattering (ELS) analyzer combined with non-invasive backscatter technology (NIBS) (Malvern Zetasizer Nano ZS, Malvern Instruments, U.K). The samples (1 mL) were analyzed without any previous modification or dilution. All reported values were the average result of three consecutive measurements at 20° C. on the same sample using the Zetasizer Software, the next day after production. Size data were based on intensity size-distribution and corresponded to z-average±standard deviation between the three measurements.

Morphology characterization by Cryo-TEM: Nanoformulations were examined by cryo-TEM to directly analyze vesicles morphology and learn on their uniformity (heterogeneity) and coexistence of structures. Information about size, shape, number of bilayers and bilayers distribution was gathered. Vitrified specimens were prepared after few days of nanoformulation production and 2-3 times in the following month, to learn about the short-term stability. Nanoformulations were stored at 4° C. until cryo-TEM analysis. For that, they were equilibrated for 30 min at 25° C. and then vitrified from this temperature in a controlled specimen preparation chamber following well established procedures (Danino, D. 2012) and examined in a T12 G2 Tecnai (FEI) and a Talos F200C (Thermo Fisher) microscopes at cryogenic temperatures. Perforated Ted Pella grids were used; vitrified specimens' temperature was always kept below −170° C. Images were recorded with a Gatan UltraScan 2 k×2 k CCD camera or a Ceta camera at low dose operation, as previously described (Danino, D. 2012). Images were recorded at various magnifications (from 8.8 K to 53 K) to properly capture all structures, namely, at different length scales, ranging from few nm to few hundreds. No image processing was applied except for background subtraction. All measurements were performed at the CryoEM Laboratory of Soft Matter at the Technion (Israel Institute of Technology, Israel).

Morphology characterization of liposomes using small-angle X-ray scattering (SAXS): Quantitative information about the liposomes' bilayer thickness and profile, degree of lamellar structure, and amount of incorporated GLA was investigated with small-angle X-ray scattering (SAXS) on an optimized NanoSTAR SAXS instrument (Pedersen, J. S., 2004) from Bruker AXS set up at Aarhus University and equipped with a liquid Ga metal jet X-ray source (Excillum) (Schwamberger, A. et al. 2015) and scatterless slits (Li, Y., et al. 2008). GLA in water (1 mg mL-1) and liposomes or hybrid-liposomes (1.5 mg mL-1) in their dispersant medium (water or water with 4% EtOH and 0.8% DMSO v/v) were measured, the matching backgrounds subtracted and water was used for absolute scale calibration. Note that prior to the measurements, the samples were checked for changes during shipment by performing DLS in Aarhus on an ALV instrument (ALV, Langen, Germany) with an ALV/CGS-8F goniometer equipped with an ALV-6010/EPP multi-tau digital correlator.

Nanovesicles stability: The stability at 4° C. of the liposomal systems was followed by measuring the size, polydispersity index (PDI) and ζ-potential of the nanovesicles at different time points (1, 7, 14, and 31 days after production) using a DLS equipment (Malvern Zetasizer Nano ZS; Malvern Instruments) as described previously.

Enzyme quantification and entrapment efficiency: The entrapment efficiency (EE %) was determined by comparing the amount of the enzyme encapsulated in the nanovesicles after removing the free GLA by diafiltration (named prototype Loaded, L) with the amount of initial GLA present in the raw batch obtained just after their production (named prototype Total, T), see Equation (1). The GLA loading was calculated by comparing the amount of GLA loaded on liposomes after elimination of free GLA with the total amount of membrane components of the vesicles, see Equation (2). Statistics were done by two-sample t-test using Minitab® 17 statistical software (2013).

$$EE \% = (\text{mass GLA Loaded/mass GLA Total}) \times 100 \quad \text{(Equation 1)}$$

$$GLA \ loading = \text{mass GLA Loaded/mass membrane components} \quad \text{(Equation 2)}$$

To detect and quantify the recombinant enzyme concentration in each of these samples, SDS-PAGE was performed by using TGX Stain-Free™ FastCast™ acrylamide 12% gels (Bio-Rad, ref. 161-0185). To visualize the fluorescent bands, a ChemiDoc™ Touch Imaging System (Bio-Rad) was used. GLA protein amounts were estimated by densitometry after SDS-PAGE and photoactivation, with known amounts of a control His-tagged GLA produced, purified and quantified in-house. Samples and standards, to be quantitatively compared, were run in the same gel and processed as a data set. Densitometric analysis of the bands were performed with the Image Lab™ software (version 5.2.1., Bio-Rad).

In vitro enzymatic activity: GLA enzymatic activity was assayed as previously described (Cabrera, I., et al. 2016) using fluorometrical methods initially described by Desnick et al. 1973 with the modifications of Mayes et al. 1981 The protocol included the use of 4-methylumbelliferyl α-D-galactopyranoside (4-MUG, M-7633 Sigma Aldrich) as substrate (2.46×10-3 M) in assay buffer (0.01 M acetic acid, 0.01 M acetate, pH 4.5). The reaction was stopped by glycine buffer (0.1 M, pH 10.4) and the released product (4-methylumbelliferone or 4-MU) was determined by fluorescence measurement (λexc=365 nm, λem=450 nm), and fluorescence measurements were transformed into 4-MU pmol using a regression plot and adjusted per time and protein quantity.

In vitro efficacy assay: The ability of GLA-loaded nanovesicles to reach the lysosomes and hydrolyze Gb3 was tested in primary cultures of mouse aortic endothelial cells (MAEC) from GLA deficient mice (GlatmKul1) (Oshima, T. et al. 1997). These cells were isolated at the in vivo Experimentation Platform/U20 of ICTS NANBIOSIS and grown as previously described (Cabrera, I., et al. 2016) in RPMI media supplemented with non-essential amino acids (Gibco), heparin (0.1 mg mL⁻¹, Sigma Aldrich), endothelial cell growth supplement (ECGS) (0.05 mg mL-1, BD), hydrocortisone (1 μg mL⁻¹, Sigma Aldrich) and fetal bovine serum (10-20%, Gibco) to allow the growth of endothelial cells. Cells in passages 2-5 were seeded in 24-well plates to 60-80% of confluence and incubated with Gb3-NBD (0.8× 10⁻⁶ M, Matreya) along with the specified concentrations of tested compounds. After 48 h, Gb3-NBD fluorescent signal was analyzed by flow cytometry (FacsCalibur, Beckton Dickinson) in viable cells (negative to 7-aminoactinomycin D staining). The fluorescent signal in control cells (without treatment) was established as 100% and the percentage of Gb3 loss (% Gb3 loss=100−% Gb3-NBD signal) was used to plot the results.

In vitro toxicity: Cell cytotoxicity was tested using 3-(4,5-dimethylthiazol-2-yl]-2,5-diphenyltetrazolium bromide (MTT) on HeLa cells (Botella P et al. 2011). Briefly, 2,000 cells were seeded in 96-well plates, let to adhere and then exposed to different doses of the nanovesicles for 72 h. Then, an MTT solution (5 mg mL-1) in PBS was added to the wells and incubated during 4 additional hours. Formazan crystals resulted from the MTT reduction by active mitochondria were dissolved with DMSO and spectrophotometrically measured at 590 nm (Biotek ELx800 Absorbance Microplate Reader, Izasa Scientific). The data were expressed as the percentages of viable cells compared to the cell survival of a non-treated control group.

In vitro hemocompatibility: Two types of assays were performed to test the hemocompatibility of the nanosystems. On the one hand, their effect on the integrity of red blood cells was measured using a hemolysis test (Giannotti, M I. et al. 2016). On the other hand, their potential interference with blood coagulation was studied by analyzing the plasma coagulation times. In detail, for the hemolysis test, mouse red blood cells (RBC) were isolated from three wild type C57BL6 mice, resuspended in 2% (v/v) of PBS, and exposed to different concentrations of test compounds during 1 h at 37° C. in duplicates. The amount of released hemoglobin was measured in a spectrophotometer at 405 nm (Biotek ELx800) after centrifugation (1000 g, 10 min). Absorbance values were referred to a positive control of 100% hemolysis obtained after incubating RBC with 1% of Triton-X. Samples with <5% were considered non-hemolytic.

The effect of the nanovesicles in plasma coagulation was tested as previously reported (Rafael, D., et al. 2018) using the Start4 equipment (Stago, France) and following the manufacturer's protocol to determine the activated partial thromboplastin time (APTT), the prothrombin time (PT), and the thrombin time (TT). Values were compared to the normal reference time ranges. The APTT assay was used to assess the intrinsic pathway, while the prothrombin time (PT) assay was a measure of the extrinsic pathway. Extrinsic and intrinsic pathways converged into the common pathway. Thrombin time (TT) was an indicator of the functionality of the final common pathway.

In vivo toxicity: In order to test the feasibility of repeated administration of MKC containing nanovesicles, the effect of 8 intravenous (i.v.) administrations of hybrid-liposomes at three different doses (0.37, 1.22 and 3.67 mg lipid per administration) were tested in wild type C57BL6 female mice (22-38 g) obtained from our GLA transgenic colony maintained in heterozygosity (GlatmKul1) (Oshima, T., et al. 1997). Animal care was handled in accordance with the Guide for the Care and Use of Laboratory Animals of the Vall d'Hebron University Hospital Animal Facility and followed the EU Directive 2010/63/EU for animal experiments. Precise experimental procedures were approved by the Animal Experimentation Ethical Committee at the institution and the regional government (ref. 9572).

All studies using animals or samples derived from animals, including MAEC obtaining and hemocompatibility assays, were performed by the ICTS NANBIOSIS, at the CIBER-BBN's in vivo Experimental Platform of the Functional Validation & Preclinical Research (FVPR) area (U20 In vivo Experimental Platform, Nanbiosis, Barcelona, Spain).

Stability of the nanostructured formulations in the assay conditions: The stability of the nanostructured formulations in the assay conditions, diluted 1:1600 in acetic buffer (0.01 M acetic acid, 0.01 M acetate, pH 4.5), containing the 4-MUG substrate (2.46×10-3 M), 37° C., 60 min, was also checked.

The integrity of the nanostructured in the assay conditions was assessed by DLS and by Nanoparticle Tracking Analysis—Nanosight (NTA). The NTA (Nanosight NS300, Malvern Instuments, U.K., equipped with a sCMOS camera and a 488 nm laser) tracks particles individually and uses the Stokes Einstein equation for calculating their hydrodynamic diameters as well as the particle concentration. A video of particles moving under Brownian motion in a field of view of 100 μm×80 μm×10 μm was recorded and analyzed by the NTA software. The mean size, PDI, and particle concentration of the nanovesicles were assayed.

Stability of (2.2% MKC)-HLP in Human Serum

Stability of 12-fold concentrated (2.2% MKC)-HLP in human serum was measured by turbidity measurements, that allowed the monitoring of changes in the system over time. By turbidimetrical methods, it was possible to measure the transmissivity and hence the attenuation of light. Changes in transmissivity over time, can act as indicator of changes in the suspension, e.g., if sedimentation or increasing of nanoparticles size occured. Turbidity can be then assessed by absorbance, since the absorbance has a logarithmic relationship to the transmittance.

The 12-fold concentrated (2.2% MKC)-HLP system was incubated with two different concentrations of human serum (H4522, Sigma-Aldrich), 75% and 90% (vol %), in triplicates in a 48-well plate. Samples were then incubated at 37° C. in orbital shaker agitation, and analyzed at 0 min, 15 min, 30 min, 60 min, 90 min, and 120 min. At each time-point the absorbance of samples was read at λ=300 nm (Microplate reader Infinite 200 Pro, Tecan) with the corresponding amount of serum alone as reference. Relative turbidity was determined dividing the sample turbidity by the turbidity at time zero (Eq S1). No significant changes were observed.

Additionally, concentrated (2.2% MKC)-HLP was incubated with 50% (vol %) of human serum (1 h, 37° C., agitation by orbital shaker). No macroscopic appearance was observed. Then, liposome integrity was also assessed by cryoTEM imaging, demonstrating the stability of the liposomal vesicle structure in presence of serum.

Theoretical number of GLA per vesicle: Being human GLA a homodimeric enzyme with a monomer weight of 48.8 kDa, the whole GLA showed an approximated molecular weight of 100 KDa. A theoretical number of homodimer GLA units per nanovesicle was calculated in an approximated approach, using the following theoretical (Table 1) and experimental (Table 2) data of the systems after purification by diafiltration (Loaded prototype), since non-incorporated GLA was removed. It was only possible to perform these calculations for HLP-GLA hybrid-liposomes, due to LP-GLA instability issues and unsuitability of SAXS technique for MQ-GLA quatsomes.

TABLE 1

| Theoretical data of hybrid-liposomes. | |
| --- | --- |
| GLA parameters (homodimer) | |
| Molecular weight (M$_W$) | 100 kDa (100,000 g/mol) |
| Liposome's parameters | |
| Theoretical lipid concentration (C)[a] | 1.5 mg mL$^{-1}$ |
| Bilayer Thickness (T), from SAXS[b] | 5 nm |
| Theoretical lipid bilayer density (d)[c] | 1 g cm$^{-1}$ |

[a]Theoretical amount of lipid used in the initial preparation by DELOS-SUSP procedure;
[b]Estimated from SAXS analysis of blank HLP systems;
[c]From T. Miyoshi et al (2014).

TABLE 2

Experimental data of hybrid-liposomes and final calculation
of number of GLA (homodimer) per vesicle.

| System | [GLA][a] [µg mL$^{-1}$] | # of GLA[b] [mL$^{-1}$] | Size (D)[c] [nm] | Lipid volume per liposome (V)[d] [cm$^3$] | # of liposomes[e] [mL$^{-1}$] | GLA/ vesicle[f] |
|---|---|---|---|---|---|---|
| (0.4% MKC)-HLP-GLA$_{20}$ | 2.8 | $1.68 \times 10^{13}$ | 140 | $3.08 \times 10^{-16}$ | $4.87 \times 10^{12}$ | 3.4 |
| (2.2% MKC)-HLP-GLA$_{20}$ | 6 | $3.60 \times 10^{13}$ | 124 | $2.42 \times 10^{-16}$ | $6.21 \times 10^{12}$ | 5.8 |
| (2.2% MKC)-HLP-GLA$_{8.5}$ | 4.6 | $2.76 \times 10^{13}$ | 112 | $1.97 \times 10^{-16}$ | $7.61 \times 10^{12}$ | 3.6 |
| (4.3% MKC)-HLP-GLA$_{20}$ | 12 | $7.20 \times 10^{13}$ | 123 | $2.38 \times 10^{-16}$ | $6.31 \times 10^{12}$ | 11.4 |

[a]Determined by TGX (see Experimental Section);
[b]Calculated using Equation S2 (see below), where NA was the Avogadro's number;
[c]From DLS measurement, mean size based on intensity;
[d]Lipid volume per liposome, calculated using Equation S3;
[e]Number of liposomes, calculated using Equation S4;
[f]Ratio between number of GLA dimers (# of GLA) and number of liposomes (# of liposomes).

$$\#of\ GLA(mL^{-1})=[GLA]/M_w \times N_A \qquad (S2)$$

$$V(cm^3)=Surface\ vesicle \times T=4\pi(D/2)^2 \times T \qquad (S3)$$

$$\#of\ liposomes(mL^{-1})=C/V \times d \qquad (S4)$$

Statistical analysis: All results were expressed as the mean±standard deviation (SD) of several experimental replicates, unless otherwise specified. ANOVA tests, student's t-tests or equivalent non-parametric tests were used to investigate the differences between different formulations, using Prism 6.02 software (GraphPad Software, Inc., CA, USA). Statistical differences were accepted as significant ($p<0.05$, *), very significant ($p<0.01$, ) or as highly significant ($p<0.001$, *) according to the obtained p-value.
Results:
1.1 Characterization of the Nanovesicles:

GLA-nanovesicle systems were obtained using three different membrane compositions and all were functionalized with chol-PEG200-RGD to allow the recognition of αvβ3-integrins overexpressed in endothelial cells (as explained in Cabrera, I., et al. 2016). The first formulation was constituted of DPPC, cholesterol, and chol-PEG200-RGD yielding liposomes (LP). The second formulation was composed of cholesterol, chol-PEG200-RGD, and h-MKC (more than 50% MKC as explained in the material and method section), that formed quatsomes (MQ). For the third system, a small amount of MKC was added to the liposome formulation at three different l-MKC concentrations: 0.4, 2.2, and 4.3 mol %, allowing the generation of hybrid-liposomes (HLP) with positively charged membranes. All the GLA-loaded systems (named LP-GLA$_{20}$, MQ-GLA$_{20}$, and HLP-GLA$_{20}$, respectively) were prepared using the same initial theoretical GLA concentration, i.e., 20 µg/ml. An additional HLP-GLA$_{8.5}$ system was prepared at the lower GLA concentration of 8.5 µg/ml, to yield the same enzyme and membrane components ratio of 3.4 µg pmol-1, as in MQ-GLA$_{20}$ (see Table 3). All the nanovesicles were prepared with the DELOS-SUSP production route described in the Experimental Section.

The composition of the obtained nanovesicles is described in table 3 below and their physicochemical characteristics are described in table 4 below.

TABLE 3

Compositions of the nanovesicle systems prepared by DELOS-SUSP at a working condition of Pw
CO2 = 10 MPa, 308K and XCO2 = 0.85. Concentration of components in organic and aqueous phase before
depressurization.

| Nanovesicle systems (GLA theoretical) | Name | Organic Phase | Aqueous phase | a) | b) | c) |
|---|---|---|---|---|---|---|
| Quatsomes (blank) | MQ | MKC (54.51 × 10$^{-3}$M) Cholesterol (24.0 × 10$^{-3}$M) Chol-PEG200-RGD (3.1 × 10–3M) 7.7% EtOH, 3.0% DMSO (v/v) | water | 3.57 | — | — |
| GLA-loaded Quatsomes (20 µg mL$^{-1}$) | MQ-GLA$_{20}$ | MKC (54.51 × 10-3M) Cholesterol (24.0 × 10$^{-3}$M) Chol-PEG200-RGD (3.1 × 10$^{-3}$M) 7.7% EtOH, 3.0% DMSO (v/v) | GLA in water (21 µg mL$^{-1}$) | 3.57 | 3.40 | 5.6 |
| 0.4% mol MKC Hybrid-Liposomes (blank) | (0.4% MKC)-HLP | DPPC (30.4 × 10-3M) Cholesterol (19.2 × 10–3M) Chol-PEG200-RGD (2.1 × 10–3M) MKC (0.2 × 10–3M) 4% EtOH, 0.8% DMSO (v/v) | water | 1.54 | — | — |
| GLA-loaded 0.4% mol MKC Hybrid-Liposomes (20 µg mL-1) | (0.4% MKC)-HLP-GLA$_{20}$ | DPPC (30.4 × 10-3M) Cholesterol (19.2 × 10–3M) Chol-PEG200-RGD (2.1 × 10–3M) MKC (0.2 × 10–3M) 4% EtOH, 0.8% DMSO (v/v) | GLA in water (21 µg mL-1) | 1.54 | 8.50 | 13 |

TABLE 3-continued

Compositions of the nanovesicle systems prepared by DELOS-SUSP at a working condition of Pw CO2 = 10 MPa, 308K and XCO2 = 0.85. Concentration of components in organic and aqueous phase before depressurization.

| Nanovesicle systems (GLA theoretical) | Name | Organic Phase | Aqueous phase | a) | b) | c) |
|---|---|---|---|---|---|---|
| 2.2% mol MKC Hybrid-Liposomes (blank) | (2.2% MKC)-HLP | DPPC (30.4 × 10−3M) Cholesterol (19.2 × 10−3M) Chol-PEG200-RGD (2.1 × 10−3M) MKC (1.2 × 10−3M) 4% EtOH, 0.8% DMSO (v/v) | water | 1.54 | — | — |
| GLA-loaded 2.2% mol MKC Hybrid-Liposomes (20 μg mL−1) | (2.2% MKC)-HLP-GLA$_{20}$ | DPPC (30.4 × 10−3M) Cholesterol (19.2 × 10−3M) Chol-PEG200-RGD (2.1 × 10−3M) MKC (1.2 mM) 4% EtOH, 0.8% DMSO (v/v) | GLA in water (21 μg mL−1) | 1.54 | 8.50 | 13 |
| GLA-loaded 2.2% mol MKC Hybrid-Liposomes (8.5 μg mL−1) | (2.2% MKC)-HLP-GLA$_{8.5}$ | DPPC (30.4 × 10−3M) Cholesterol (19.2 × 10−3M) Chol-PEG200-RGD (2.1 × 10−3M) MKC (1.2 mM) 4% EtOH, 0.8% DMSO (v/v) | GLA in water (8.9 μg mL−1) | 1.54 | 3.40 | 5.5 |
| 4.3% mol MKC Hybrid-Liposomes (blank) | (4.3% MKC)-HLP | DPPC (30.4 × 10−3M) Cholesterol (19.2 × 10−3M) Chol-PEG200-RGD (2.1 × 10−3M) MKC (2.3 mM) 4% EtOH, 0.8% DMSO (v/v) | water | 1.54 | — | — |
| GLA-loaded 4.3% mol MKC Hybrid-Liposomes (20 μg mL−1) | (4.3% MKC)-HLP-GLA$_{20}$ | DPPC (30.4 × 10$^{-3}$M) Cholesterol (19.2 × 10−3M) Chol-PEG200-RGD (2.1 × 10−3M) MKC (2.3 × 10−3M) 4% EtOH, 0.8% DMSO (v/v) | GLA in water (21 μg mL−1) | 1.54 | 8.5 | 13 |
| Liposomes (blank) | LP | DPPC (29.7 × 10−3M) Cholesterol (17.8 × 10−3M) Chol-PEG200-RGD (3.0 × 10−3M) 4% EtOH, 0.8% DMSO (v/v) | water | 1.54 | — | — |
| GLA-loaded Liposomes (20 μg mL−1) | LP-GLA$_{20}$ | DPPC (29.7 × 10−3M) Cholesterol (17.8 × 10−3M) Chol-PEG200-RGD (3.0 × 10−3M) 4% EtOH, 0.8% DMSO (v/v) | GLA in water (21 μg mL−1) | 1.54 | 8.5 | 13 | a), Membrane components [mg/mL$^{-1}$]: sum of total mg of membrane components divided by total mL of final solution;

b), GLA per membrane components [μg/μmol$^{-1}$]: ratio between mass of GLA (μg) and total mass of membrane components (μmol);

c) GLA per membrane components [μg GLA mg$^{-1}$]: ratio between mass of GLA (μg) and total mass of membrane components (mg).

TABLE 4

Physicochemical characteristics of the GLA nanoformulations, the next day after production. Values in parentheses are for diafiltrated nanoformulations. Average of two independent productions for each system. (of blank vesicles and GLA-loaded vesicles were assessed by measurements of the particle size, size distribution, and ζ-potential using DLS.

| Nanovesicle systems | Mean size [nm] | PDI | ζ-potential [mV] | GLA [μg mL$^{-1}$] | Theor. GLA per vesicle$^{a)}$ | GLA per membrane component [μg μmol$^{-1}$]$^{b)}$ |
|---|---|---|---|---|---|---|
| LP | 152 ± 1 | 0.41 ± 0.02 | 26 ± 1 | — | — | — |
| LP-GLA$_{20}$ | —$^{c)}$ | —$^{c)}$ | −6.3 ± 0.2 | 20 ± 1 | ND | 8.3 |
|  | —$^{c)}$ | —$^{c)}$ | (−25.2 ± 0.8) | (7 ± 2) |  |  |
| MQ | 69 ± 1 | 0.19 ± 0.01 | 64.2 ± 0.7 | — | — | — |
| MQ-GLA$_{20}$ | 69 ± 3 | 0.19 ± 0.02 | 61.0 ± 0.9 | 18 ± 1 | ND | 3.4 |
|  | (65 ± 3) | (0.20 ± 0.01) | (58.0 ± 0.6) | (15.1 ± 0.3) |  |  |
| (0.4% MKC)-HLP | 107 ± 1 | 0.23 ± 0.02 | 36 ± 4 | — | — | — |
| (0.4% MKC)-HLP-GLA$_{20}$ | 141 ± 6 | 0.18 ± 0.02 | 17 ± 1 | 12 ± 2 | 3 | 8.3 |
|  | (140 ± 4) | (0.17 ± 0.01) | (17 ± 1) | (2.8 ± 0.2) |  |  |
| (2.2% MKC)-HLP | 112 ± 1 | 0.24 ± 0.01 | 59 ± 2 | — | — | — |
| (2.2% MKC)-HLP-GLA$_{20}$ | 123 ± 1 | 0.17 ± 0.01 | 36 ± 2 | 11 ± 2 | 6 | 8.3 |
|  | (124 ± 3) | (0.17 ± 0.02) | (42.3 ± 0.1) | (6 ± 1) |  |  |
| (2.2% MKC)-HLP-GLA$_{8.5}$ | 108 ± 2 | 0.18 ± 0.01 | 51 ± 2 | 4.9 ± 0.4 | 4 | 3.4 |
|  | (112 ± 1) | (0.20 ± 0.01) | (46 ± 1) | (4.6 ± 0.2) |  |  |
| (4.3% MKC)-HLP | 113 ± 1 | 0.23 ± 0.02 | 63.6 ± 0.7 | — | — | — |

TABLE 4-continued

Physicochemical characteristics of the GLA nanoformulations, the next day after production.
Values in parentheses are for diafiltrated nanoformulations. Average of two independent
productions for each system. (of blank vesicles and GLA-loaded vesicles were assessed
by measurements of the particle size, size distribution, and $\zeta$-potential using DLS.

| Nanovesicle systems | Mean size [nm] | PDI | $\zeta$-potential [mV] | GLA [µg mL$^{-1}$] | Theor. GLA per vesicle[a] | GLA per membrane component [µg µmol$^{-1}$][b] |
|---|---|---|---|---|---|---|
| (4.3% MKC)-HLP-GLA$_{20}$ | 126 ± 1 (123 ± 1) | 0.19 ± 0.01 (0.17 ± 0.01) | 46.8 ± 0.7 (49 ± 1) | 12.1 ± 0.9 (12 ± 1) | 11 | 8.3 |

[a]Theoretical number of GLA per vesicle;
[b]Theoretical ratio mass of GLA per mol of membrane component;
[c] Not reliable data, sample showed some sedimentation.

1.2 MKC Improved the Colloidal Stability and GLA Entrapment Efficiency of the Nanovesicles GLA-loaded liposomes (LP-GLA$_{20}$) similar to those described in Cabrera, I., et al. 2016 were prepared, but using the commercially available agalsidase alfa (Replagal®) as model enzyme of high quality, tag free, and already approved and commercialized GLA instead of the in-house produced His tag GLA obtaining similar low enzyme entrapment efficiency but less stability than the previously reported system (Cabrera et al. 2016). Entrapping the commercial GLA, LP-GLA$_{20}$ showed higher mean particle size and wider size distribution compared to LP and the previous evaluated systems (Cabrera et al. 2016), also reflected by a significantly higher polydispersity index. Besides, LP-GLA$_{20}$ showed low negative $\zeta$-potential values, fact that had a direct negative impact on their stability. Specifically, these LP-GLA$_{20}$ liposomes sedimented few days after production.

In comparison, MQ formulations showed a narrow size distribution and a significantly smaller mean size, around 70 nm. Notably, their physicochemical properties were also maintained when GLA was incorporated into the system (MQ-GLA$_{20}$).

All three HLP systems (see Table 4) formed small vesicles around 110 nm in diameter; slightly larger than the MQ vesicles, but still with a narrow size distribution. The $\zeta$-potential values directly correlated with the MKC concentration, increasing when more MKC was added to the structures. The addition of MKC maintained high and positive $\zeta$-potential values even when the GLA was entrapped (HLP-GLA$_{20}$ systems), although values were slightly below those obtained in absence of GLA (HLP). The nanoformulation stability was clearly observed when MQ-GLA$_{20}$ and HLP-GLA$_{20}$ containing the cationic MKC surfactant were compared with the non-containing MKC LP-GLA$_{20}$ system, since no vesicle sedimentation was observed up to 1 month after production for the first systems. The remarkable stability of MKC-containing systems was also be observed by monitoring the evolution of their size, PDI, and $\zeta$-potential over time (FIG. 1).

Figure 2:
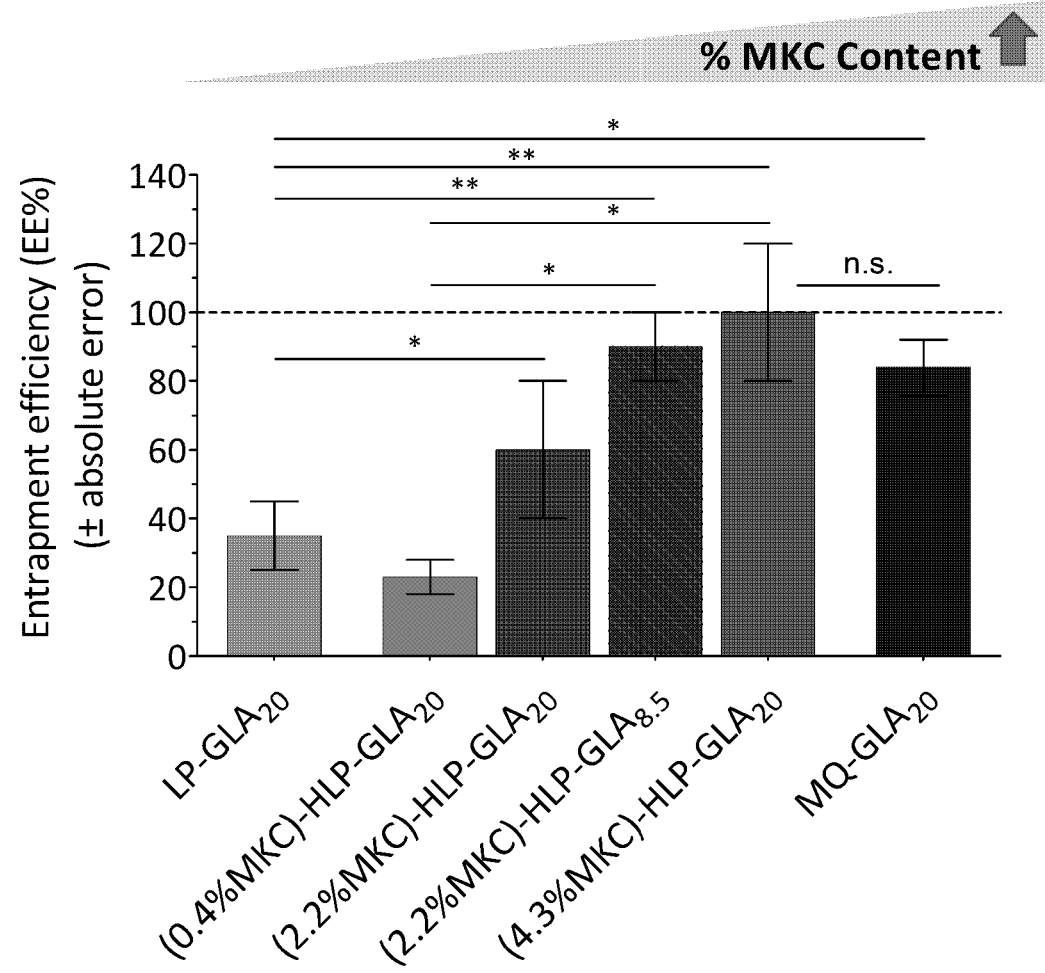
FIG. 2: GLA entrapment efficiency of all the tested systems. Non-containing MKC liposomes (LP-GLA), quatsomes (MQ-GLA) and hybrid liposomes (HLP-GLA). The results correspond to the average of three independent assays.

Next, the concentration of GLA in the nanovesicles was quantified by SDS-PAGE and densitometry analysis (GLA concentration for each nanovesicle system shown in Table 4) and, based on it, the entrapment efficiency (EE %) and GLA loading were determined (see Experimental Section). As can be seen in FIG. 2, MKC played an important role in the integration capacity of GLA into the nanoformulations. Significantly higher entrapment efficiency was achieved in MQ-GLA$_{20}$ (EE>80%) in comparison to the free-MKC LP-GLA$_{20}$ (EE 30%). As aforementioned, the quaternary ammonium surfactant MKC was the main membrane component of MQ-GLA$_{20}$ formulations, and consequently, it led to higher cationic surface charge in the membrane, which induced higher entrapment of GLA by electrostatic interactions. Similar effects were found in the hybrid-liposomal systems as shown in FIG. 2; in HLP-GLA$_{20}$ systems, EE and GLA loading directly correlated with the amount of MKC present. For the (0.4% MKC)-HLP-GLA$_{20}$ (the lowest MKC concentration) an entrapment efficiency of 23±5% was obtained, comparable to LP-GLA$_{20}$, suggesting that despite the improvement of physicochemical characteristics (size, PDI, and stability) given by MKC addition, more electrostatic interactions were needed to achieve improvement of EE. In the formulations with higher MKC levels, (2.2% MKC)-HLP-GLA$_{20}$ and (4.3% MKC)-HLP-GLA$_{20}$, considerably improved EE of up to 60±20% and 100±20%, respectively, were detected. However, the difference between EE % of (4.3% MKC)-HLP-GLA$_{20}$ and MQ-GLA$_{20}$ was not statistically significant at this specific GLA concentration of 20 µg/ml, indicating that the electrostatic interactions provided by MKC concentrations≥4.3 mol % were more than enough to entrap this amount of GLA.

SAXS was used to gain further understanding of changes in the liposome morphology. First, the scattering from the free GLA was investigated since GLA contributed significantly to the total scattering signal in the loaded liposome samples. The SAXS data of the pure enzyme could be fitted with a rigid-body refined dimer structure (Steiner, E. M., et al. 2018) based on the known dimeric crystal structure of GLA (PDB: 1r4626, $\chi^2$=1.8). Fitting was done on absolute scale yielding a concentration estimate of 1.10 mg mL-1 (assuming all GLA was on dimer form), which was slightly higher than the concentration of 1 mg mL-1 for the commercial stock GLA sample. A small increase in intensity at low scattering vector moduli, q, could suggest slight aggregation in the sample, resulting in a somewhat elevated concentration estimate. For the nanoformulations, the SAXS data showed a characteristic minimum at intermediate q, typical for liposomes, arising from the variations in electron density across the cross-section profile of the bilayer membranes. The data was fitted with a paracrystalline model (Hosemann, R. et al. 1963) based on Pabst et al. 2000 and 2003, where the average number of layers (N layers) and the bilayer thickness (T) can be determined. When fitting the data, it was observed that an additional contribution from polymer scattering had to be included to obtain good fits (Table 5). For the samples without GLA (LP and HLP), this scattering contribution was constant and probably arised from the flexible chol-PEG200-RGD on the membranes surface. For samples containing GLA, the polymer scattering was therefore fixed at an average value obtained from the GLA-free fits. In LP-GLA$_{20}$ and HLP-GLA$_{20}$, GLA also contributed to the scattering patterns and, thus, the theoretical signal from free GLA was added to the liposome scattering through a linear combination with its own individual scale factor. Even though the scattering contributions from polymer and GLA were small and to some extent correlated, it was still possible by this approach to determine the GLA concentrations with SAXS, which corresponded fairly well with the theoretically calculated GLA concentrations (Table 5).

patterns, the stability of the nanostructured formulations was confirmed, in the acidic media of the assay conditions, before performing the enzyme assays as explained in the

TABLE 5

| SAXS data of the nanoformulations. Values corresponded to the mean ± SD. | | | | | | |
|---|---|---|---|---|---|---|
| Nanovesicle systems | $\chi^{2\ a)}$ | Polymer scale $(10^{-4})$ | $[GLA]_{theo.}$ $[\mu g\ mL^{-1}]$ | $[GLA]_{fitted}$ $[\mu g\ mL^{-1}]$ | $N_{layers}{}^{b)}$ | $T\ ^{c)}$ $[Å]$ |
| LP | 1.1 | 4.6 ± 0.8 | — | — | 1.5 ± 0.1 | 51.5 ± 0.3 |
| LP-GLA20 | 1.1 | $4.2^{d)}$ | 20 | 13 ± 2 | 2.0 ± 0.1 | 51.0 ± 0.2 |
| (0.4% MKC)-HLP | 2.2 | 4.2 ± 0.8 | — | — | 1.3 ± 0.1 | 48.9 ± 0.3 |
| (2.2% MKC)-HLP | 1.5 | 3.4 ± 0.7 | — | — | 1.0 ± 0.1 | 48.6 ± 0.3 |
| (4.3% MKC)-HLP | 1.5 | 4.4 ± 0.8 | — | — | 1.0 ± 0.1 | 48.5 ± 0.4 |
| (0.4% MKC)-HLP-GLA$_{20}$ | 1.2 | $4.2^{d)}$ | 20 | 22 ± 3 | 1.1 ± 0.1 | 50.7 ± 0.3 |
| (2.2% MKC)-HLP-GLA$_{20}$ | 1.5 | $4.2^{d)}$ | 20 | 18 ± 3 | 1.1 ± 0.1 | 50.2 ± 0.5 |
| (2.2% MKC)-HLP-GLA$_{8.5}$ | 1.6 | $4.2^{d)}$ | 8.5 | 8 ± 4 | 1.1 ± 0.1 | 49.9 ± 0.4 |
| (4.3%)MKC-HLP-GLA$_{20}$ | 0.9 | $4.2^{d)}$ | 20 | 16 ± 3 | 1.1 ± 0.1 | 49.3 ± 0.3 |

$^{a)}$ $\chi^2$ was the reduced weighted chi-square;
$^{b)}$Average number of layers in liposomes;
$^{c)}$ Bilayer thickness defined as T = 2 (zH, 1 + oH, 1), where zH, 1 is the distance from the center of the bilayer to the centers of the Gaussian used to describe the headgroup and oH, 1 was the width of this Gaussian;
$^{d)}$Not fitted value.

Increasing MKC concentrations decreased the bilayer thickness (T) slightly for both GLA-containing (from 51.0 Å to 49.3 Å) and GLA-free (from 51.5 Å to 48.5 Å) liposomes. Furthermore, for samples with MKC, T was slightly higher when GLA was added, suggesting that the protein possibly binds to the positively charged liposome surface and thereby increase the apparent bilayer thickness. Both LP and LP-GLA$_{20}$ showed some multilamellarity that diminished as MKC was introduced into the liposomes, probably an effect of the general lower stability and early sedimentation observed for LP and LP-GLA$_{20}$ in comparison with HLP and HLP-GLA$_{20}$.

Figure 3:
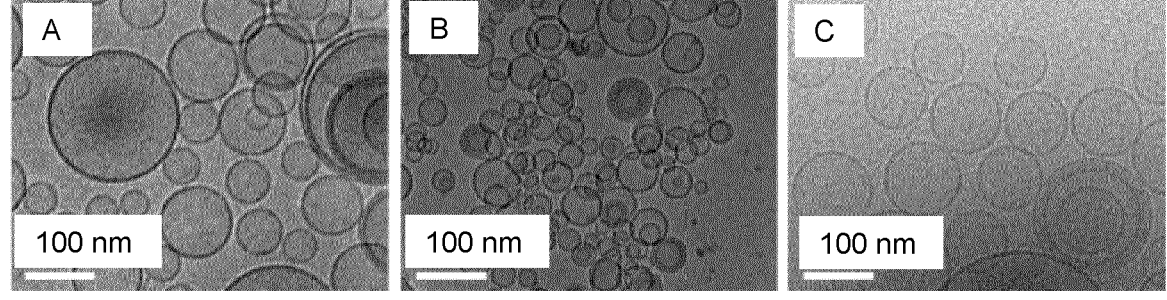
FIG. 3: Cryo-TEM images of the three different nanoformulations: A) non-containing MKC liposomes (LP-GLA20), B) quatsomes (MQ-GLA20) and C) hybrid liposomes (HLP-GLA8.5).

Direct analysis of the nanovesicles with cryo-TEM was fully consistent with the SAXS analysis (FIG. 3). The nanoformulations were largely unilamellar as expected, and rather uniform in size. LP-GLA and HLP-GLA$_{8.5}$ nanovesicles were about 120 nm in diameter, and MQ-GLA$_{20}$ nanovesicles were smaller and on average 60-70 nm in diameter, all in excellent agreement with the DLS data shown in Table 3. Because cryo-TEM showed individual nanovesicles, certain polydispersity with some double-layer structures was recognized, but overall and in agreement with the SAXS analysis, vesicles showed a high degree of unilamellarity.

Overall, the physicochemical properties showed that both quatsomes and hybrid-liposomes were promising systems for further exploration as potential carriers of the GLA enzyme. The increase in their membrane positive charge due to the presence of the cationic surfactant leaded to a narrower and more monodisperse size distribution, with a marked improvement in the colloidal stability. This amended the earlier destabilization phenomena seen in the MKC-free system (LP-GLA$_{20}$) and made MQ-GLA$_{20}$ and HLP-GLA systems suitable for further examination. Especially important was the two-fold increase in GLA entrapment efficiency compared with LP-GLA$_{20}$. This was a major advance in enzyme nanoformulations, where it was often very challenging to obtain high or full incorporation of big biomacromolecules into nanovesicles.

1.3. The Specific Enzymatic Activity of GLA was Increased when Using MKC in Less than 30% Mol The specific enzymatic activity of the GLA enzyme conjugated to the nanovesicles was measured using a fluorescent assay following Cabrera, I., et al. 2016. Since the GLA was a lysosomal enzyme, the enzymatic activity assay needed to occur at low pHs. To be sure that the enzyme activity was measured over the non-altered encapsulation Method section and the mean size, PDI, and particle concentration of the nanovesicles were maintained in the enzymatic assay conditions, without significant change.

Figure 4A:
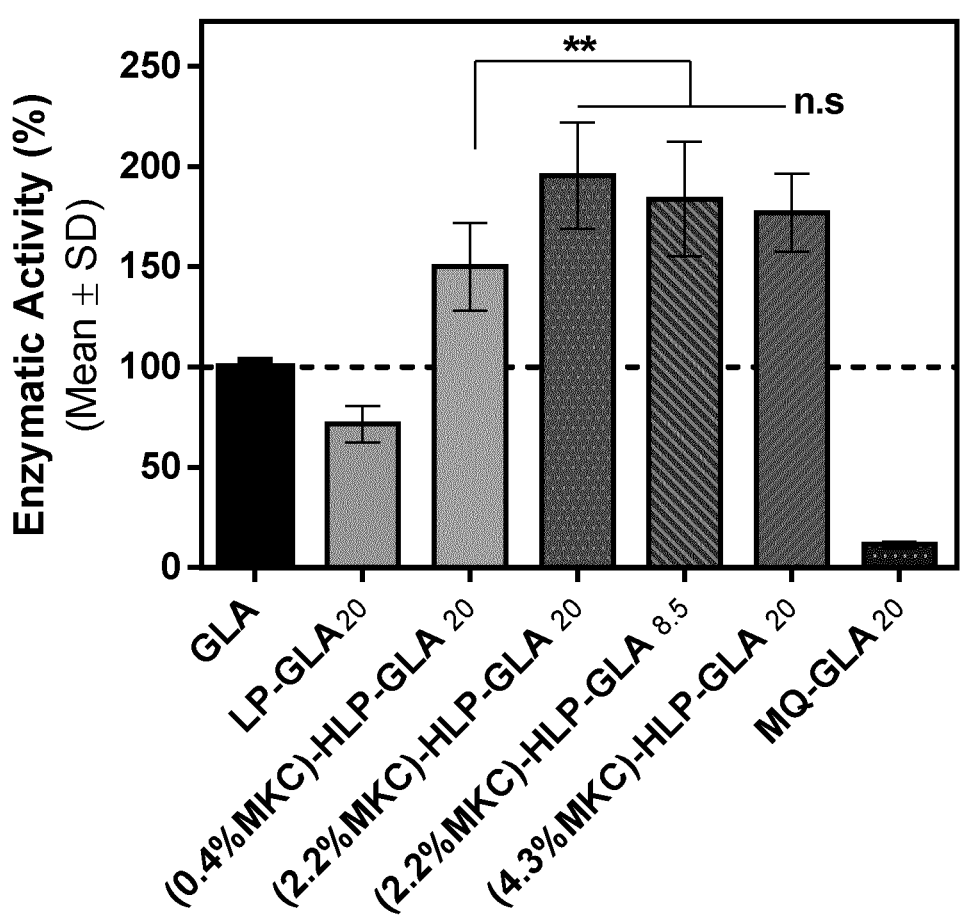
FIG. 4: Enzymatic activity and in vitro cell-activity of different GLA-nanovesicle conjugates: A) Enzymatic activity in liposomes (LP-GLA), quatsomes (MQ-GLA), and hybrid-liposomes containing MKC (HLP-GLA). All values refer to the enzymatic activity with free GLA as reference. The results correspond to the average of three independent assays. B, Enzymatic activity in the presence of free MKC, reproducing the same concentrations than in the HLP-GLA systems (assay corresponds to a single representative experiment, replicated in two different assays); C) In vitro efficacy assays measured as loss of Gb3 (due to its hydrolysis by GLA) in primary endothelial cells derived from Fabry KO mice. Assay corresponds to a single representative experiment, replicated in three independent assays.

Surprisingly, as can be seen in FIG. 4A, the results indicated that the presence of MKC in the nanovesicles had a dramatic impact on the protein enzymatic activity. The use of h-MKC in MQ-GLA$_{20}$ provoked a considerable reduction in the activity of the enzyme of up to 80%. On the other hand, when no MKC was used (LP-GLA$_{20}$ system), enzymatic activities were about half of those of the commercially available GLA (Replagal® as commercialized was formulated as solution with a series of excipients (polysorbate-20, sodium chloride, sodium hydroxide and sodium phosphate monobasic) in its final pharmaceutical form). The entrapment of the commercialized GLA formulation into noncontaining-MKC liposomes possibly destabilized the enzyme, initially stabilized in its original formulation with 0.2 µg/ml of the non-ionic polysorbate-20 surfactant.

Interestingly, in the case of HLP-GLA, the presence of l-MKC in the liposomal membrane helped to substantially increase the enzyme activity in the nanoformulation, since the enzymatic activity of all hybrid-liposomes were above of those of the commercial free enzyme and LP-GLA$_{20}$ without MKC in the membrane. Statistical comparison between LP-GLA and HLP-GLA or LP-GLA and MQ-GLA was highly significant (p=0.0001, *) and very significant (p=0.004, ), respectively (not shown inside the graph in FIG. 4A for sake of clarity). Statistical comparisons on enzymatic activity among HLP-GLA where only significant when comparing (0.4% MKC)-HLP-GLA$_{20}$ to other HLP-GLAs containing higher MKC content (p=0.004, **).

Figure 4B:
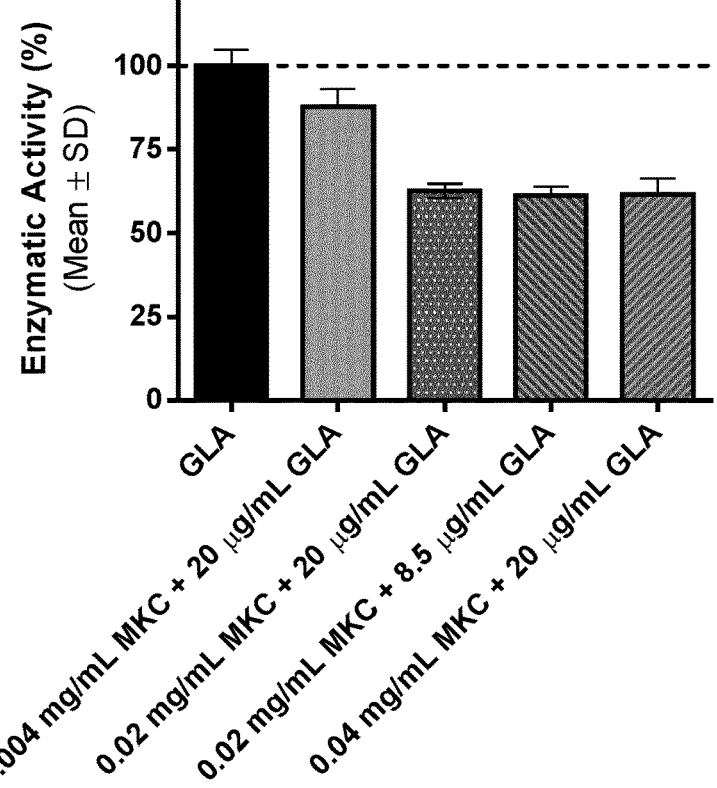

Enzymatic activity of GLA, measured in presence of pure MKC at equivalent surfactant concentrations to those in HLP-GLA formulations, was lower than the one measured for the corresponding formulations (See FIG. 4B) This result pointed out that the enzymatic activity enhancement was related to the entrapment of GLA in HLP-GLA liposomes, containing l-MKC in their membrane, and not only due to the presence of this surfactant in the formulation.

The hybrid-liposomal systems produced surprising results in terms of improved GLA loading, physicochemical stability, as well as higher enzymatic activity of conjugated GLA in comparison with the other nanovesicle systems used.

Figure 4C:
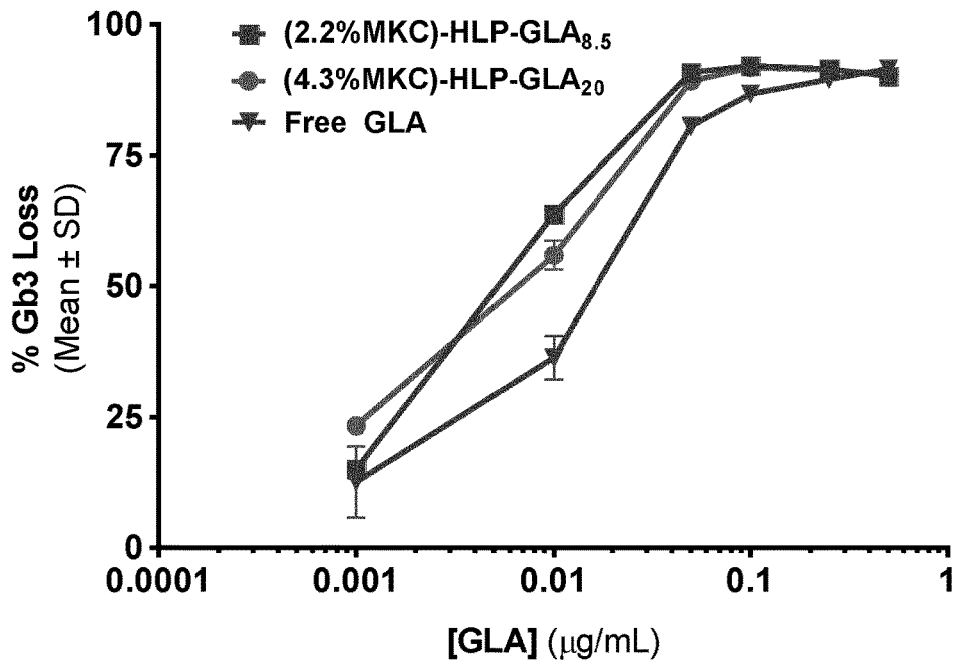

1.4. The Liposomes of the Invention Increased the In Vitro Efficacy of the GLA Enzyme while Keeping a Safe In Vivo Toxicological Profile The capacity of HLP-GLA to enter cells and reduce the Gb3 deposits within the lysosomes was measured by adding a fluorescent-labelled Gb3 (NBD-Gb3) (Cabrera, I., et al. 2016). In this assay, mouse aortic endothelial cells (MAEC) from Fabry KO mice, with no endogenous GLA activity, were challenged with different concentrations of HLP-GLA. Consequently, total Gb3 loss was solely attributed to the action of the enzyme carried by the nanovesicles after cell internalization and lysosomal localization, where the low pH allowed enzyme activity. Results showed better efficacy of nanoformulated enzymes compared to experiments with free GLA, in accordance with the previously described increase in the intrinsic enzymatic activity (FIG. 4C), as well as in agreement with the previous published GLA loaded liposomal system Cabrera, I., et al. 2016. However, unlike the previous system, these new HLP-GLA systems presented enhanced colloidal stability and higher GLA entrapment efficiency (EE>90%) and, thus, they were of better quality, overall fulfilling the physicochemical and biological requirements to warrant their progress to an advanced stage of preclinical development.

In order to characterize the safety and toxicological profile of the HLP-GLA systems, several in vitro assays were performed. Firstly, HeLa cells were exposed to different concentrations of HLP-GLA and cell viability was measured after 72 h incubation by the MTT assay. Cell viabilities were kept above 75% in all cases, indicating that integration of MKC into the hybrid-liposomes was not inducing any dose-dependent cytotoxicity.

Further, it was also tested whether the HLP-GLA could be safely administered intravenously, using well-established hemocompatibility studies. First, the impact of different nanoformulations in red blood cell fragility was studied by using hemolysis tests in murine blood samples. It was found that none of the tested HLP-GLA systems induced significant hemolysis and the values measured never surpassed 5% of total hemolysis.

Similarly, no significant variations in plasma coagulation times were detected after incubating human plasma with 0.154 mg mL-1 of (2.2% MKC)-HLP-GLA20, and the results were within the normal expected range (see table 6)

TABLE 6

Plasma coagulation times measured as prothrombin time (PT), activated partial prothrombin time (APTT) and thrombin time (TT) after incubation with (2.2% MKC)-HLP-GLA20 liposomes. Values into brackets correspond to diafiltrated nanoformulations. Non-treated plasma (control plasma) and the nanoformulation without liposomes (vehicle) were used as controls. Values in the table correspond to the mean +/- SD of 2 independent measurements.

| Sample | PT [s] | APTT [s] | TT [S] |
|---|---|---|---|
| Normal coagulation time range | ≤13.4 | ≤34.1 | ≤21 |
| Control plasma | 12.3 ± 0.1 | 33.6 ± 0.1 | 16.4 ± 0.7 |
| Vehicle | 12.4 ± 0.0 | 34.4 ± 0.4 | 16.2 ± 0.2 |
| | (12.3 ± 0.1) | (34.3 ± 0.3) | (16.6 ± 0.1) |
| (2.2% MKC)-HLP-GLA$_{20}$ | 12.6 ± 0.1 | 33.9 ± 0.1 | 16.0 ± 0.0 |
| | (12.3 ± 0.0) | (33.9 ± 0.0) | (16.2 ± 0.4) |

Once the HLP-GLA demonstrated to be safe in vitro, an in vivo repeated dose toxicity assay was performed with just the vehicle (without GLA). The rationale behind this preliminary in vivo study was to evaluate the plausibility of using MKC containing liposomes and, thus, identify potential toxicities caused by the vehicle in vivo. Accordingly, C57BL6 wild type mice were treated twice a week during 4 weeks with three different doses (0.37, 1.22 and 3.67 mg of lipid per injection, which corresponded approximately to 12, 41 and 105 mg kg-1 of lipid) of non-GLA (2.2% MKC)-HLP hybrid-liposomes. Prior to administration, concentration of the liposomal system was needed to reach the desired doses, mimicking the concentration factor that was required to reach sufficient GLA concentration in the nanoformulation for achieving in vivo a therapeutic dose. This step did not induce any significant change in physicochemical properties of the system and 12-fold concentrated samples were obtained (concentrated as indicated in the material and method section). Additionally, stability of this system in human serum (37° C.) was assessed by turbidity measurements (as indicated in the material and method section). No significant changes in turbidity were observed, and vesicle integrity was also confirmed by cryoTEM.

The treatment schedule was aimed at mimicking that of efficacy assays with GLA in Fabry mice, where repeated administrations of the enzyme were required to ensure a sustained effect (with Replagal® or Fabrazyme®). Overall welfare of the animals (general appearance, drinking/eating behavior and response to stimuli) as well as weight were monitored during the 5 weeks (4 weeks of treatment plus an additional week of surveillance), with no significant alterations of any of the monitored parameters demonstrating a good tolerability of the HLP system upon repeated administrations.

Conclusion:

It was explored the use of two different RGD-targeted lipid-based nanovesicles for GLA enzyme entrapment, with distinct MKC content, e.g. non-liposomal nanovesicles, known as quatsomes, which contained high MKC concentrations (>50 mol % of the total membrane components), and hybrid-liposomes that contained low MKC concentrations (<5 mol % of the total membrane components). Both systems were successfully prepared using the DELOS-SUSP procedure, confirming the suitability of this technique for the preparation of multifunctional nanovesicles with a high level of homogeneity. Membrane composition of these vesicles strongly impacted both the physicochemical and biological characteristics of the nanoformulations. The addition of positive charges to the membrane by incorporating MKC improved the colloidal stability of the nanoformulation.

Moreover, the amount of positive charge added to the system had a direct impact on the ability to entrap the enzyme. Consequently, quatsomes showed high entrapment efficiencies, but, surprisingly, hybrid-liposomes, with lower levels of MKC, achieved enzyme entrapment efficiencies similar to quatsomes. However, despite high entrapment efficiency and good colloidal stability, quatsomes completely abolished the activity of the GLA enzyme. In vitro, I-MKC hybrid-liposomes (0.4-4.3 mol % of the total membrane components) showed to be non-cytotoxic and non-hemolytic. Moreover, the entrapment of GLA into these hybrid-liposomes enhanced the efficacy of the enzyme and showed greater reduction of lysosomal Gb3 than the free administered GLA. Good tolerability and no adverse side effects were observed in mice after repeated administrations of MKC-containing liposomes. Overall, the improvements in the colloidal stability, entrapment efficiency, and biological activity of GLA described herein allowed a reduction in dose and volume of GLA-conjugated liposomes to be administered in vivo, a necessary step to demonstrate the significant benefit of these systems versus the current enzymatic replacement therapy in Fabry patients. This results allow to use the, I-MKC hybrid-liposomes for Fabry disease treatment.

Example 2. Impact of the Ratio of GLA to Membrane Excipients

The relation between the GLA concentration and the concentrations of the membrane excipients forming the nanoliposomal system (i.e. DPPC, Cholesterol, and Cholesterol-PEG400-RGD and the non-lipid cationic surfactant) was analyzed.

Previous published studies on nanoGLA formulations using GLA-HIS (obtained in HEK cells), without MKC surfactant, and Chol-PEG200-RGD, showed that ratios of more than 14 µg GLA/mg membrane excipients resulted in non-stable intermediate formulations, presenting high polydispersity values and poor stability over time, as described in Cabrera et al. 2016. Furthermore, those previous formulations had low encapsulation efficiencies. On the other side, a lower GLA to membrane ratio of 6.1 enabled a stable formulation, but the GLA concentration achieved was only of 8.5 µg/mL (Cabrera et al. 2016).

Once the addition of MKC revealed an improvement on physicochemical and encapsulation properties of the nanoliposomes, as indicated in example 1, range-finding tests were carried out to evaluate if optimized formulations with previously discarded ratios around 30 µg GLA/mg membrane excipients (as disclosed in (Cabrera et al. 2016) could be obtained in a stable manner.

Materials and Methods

All the materials and methods used in this example were the same as indicated in example 1, unless otherwise indicated.

GLA-loaded nanoliposomes (nanoGLA) formulation consisted of the entrapment of GLA protein (in this case a tag-free alpha galactosidase (named as "recombinant human GLA", "rh-GLA"), explained below) in an aqueous liposomal system containing DPPC, Cholesterol and Cholesterol-PEG400-RGD with a small amount of surfactant myristalkonium chloride (MKC) (5% mol in respect to the other membrane excipients). The nanoGLA was produced in two steps 1) by DELOS-susp obtaining an intermediate dispersion and 2) this intermediate was concentrated and diafiltrated by Tangential Flow Filtration (TFF).

For the in vitro experiments "hybrid-liposomes" (HLP) comprising low MKC (5 mol % of the total membrane components) similar to the HLP of example 1 were obtained (as described in material and methods of example 1) but in this case the PEG was PEG400, named herein as "Liposome DPPC:Chol:(Chol-PEG400-RGD):MKC" or "HLP DPPC: Chol:(Chol-PEG400-RGD):MKC" or "nano-GLA". Therefore, this liposome contained the indicated MKC content and also the phospholipid DPPC, cholesterol, and the RGD unit (tripeptide Arg-Gly-Asp) linked to the cholesterol moiety (chol-PEG400-RGD) as described in Cabrera, I., et al. 2016, wherein the $PEG_{400}$ (subscript corresponded to the PEG molecular weight) was covalently attached to the cholesterol by one end via a bond of the type alkyl ether and was covalently attached to the peptide comprising the RGD sequence by the other end via a carbamate bond; wherein the RGD peptide was the head-to-tail cyclic cRGDfk (SEQ ID NO: 2). This liposome was obtained using the DELOS-SUSP method as indicated in example 1 with slight differences in the diafiltration and concentration step. The liposomes produced by DELOS-SUSP were concentrated 7.0 to 7.5-fold and diafiltrated in water or water with glucose 5% w/v applying 4 to 5 diafiltration cycles.

The mol ratio of the DPPC:cholesterol:chol-PEG400-RGD was 10:6.5:0.5. Thus, the chol-PEG400-RGD represented the 3% mol in respect of the components.

The Liposomes DPPC:Chol:(Chol-PEG400-RGD):MKC comprised also the tag-free alpha galactosidase ("rh-GLA") wherein the monomer had the sequence SEQ ID NO: 1 (approximately 100 KDa tag free protein with a non-modified sequence, the same sequence as the human GLA but without the signal peptide included in the UniProt number P06280 at date of Jan. 1, 2021) (Gene ID: 2717) and which was obtained recombinantly using the GLA gene using Chinese Hamster Ovary (CHO) cell culture (CHO K1 cells) following standard cell culture techniques (stable expression-based production method) (Sambrook J. et al. Molecular Cloning a Laboratory Manual, Third Edition. Cold Spring Harbor Laboratory Press. Chapter 16, 16.1-16-54).

The rh-GLA was loaded as indicated in example 1 and it was entrapped into the nanoliposomes (liposomes DPPC: Chol:(Chol-PEG400-RGD):MKC) through a noncovalent binding; for example, for the weight ratio of 30, 0.27 mg/ml GLA was loaded, representing a ratio GLA/membrane components of about 30 µg GLA/mg membrane excipients (in respect to DPPC, Chol, Chol-PEG400-RGD and MKC).

For the example related to the impact on physicochemical properties and stability of nanoGLA formulations Ratio GLA/membrane components, the nano-GLA samples were prepared with the tag-free GLA version ("rh-GLA"), containing a 5 mol % of MKC and 3 mol % of Cholesterol-PEG400-RGD. The samples were obtained formulating GLA at 0, 30 and 45 µg/mL with 1.2 mg/mL of membrane excipients during the first DELOS step. Then, during the second production step (TFF), samples were concentrated 7.0 to 7.5-fold, obtaining different formulations of the nanoGLA containing up to 343 µg/mL of GLA and 8.4 or 9.0 mg/mL of lipidic membrane components, with GLA to membrane ratios from 0 to 41 µg/mg.

For the in vitro enzymatic efficacy in cell cultures of nanoGLA formulations, in this experiment the capacity of HLP-GLA to enter cells and reduce (hydrolyse) the Gb3 deposits within the lysosomes was measured by adding a fluorescent-labelled Gb3 (Nitrobenzoxadiazole-Gb3, NBD-Gb3) substrate in Mouse Aortic Endothelial Cells (MAEC) derived from Fabry KO mice (as disclosed in example 1 and in Cabrera, I., et al. 2016), In this assay, mouse aortic endothelial cells (MAEC) from Fabry KO mice, with no endogenous GLA activity, were challenged with different concentrations of HLP-GLA. Consequently, total Gb3 loss was solely attributed to the action of the enzyme carried by the nanovesicles after cell internalization and lysosomal localization, where the low pH allowed enzyme activity.

Results:

2.1. Impact on Physicochemical Properties and Stability of nanoGLA Formulations or the Ratio GLA/Membrane Components The results showed that the weight ratio GLA/membrane components had a critical impact on the physicochemical stability of nanoGLA regarding its macro and microscopic appearance, mean particle size and polydispersity. Besides the presence of non-lipid cationic surfactant (e.g., MKC) at low concentration (below 30% molar in respect to the phospholipid, chol, the conjugate and the surfactant), another parameter was also critical, that is, the relation between the GLA weight and the weight of the membrane excipients forming the nanoliposomal system (i.e., DPPC, Cholesterol, Cholesterol-PEG400-RGD, and MKC).

TABLE 7

| Summary of main physicochemical properties and stability of nanoGLA samples prepared at different GLA/membrane excipients ratio, using the tag-free GLA from CHO, and containing MKC and Chol-PEG400-RGD (DPPC:Chol:Chol-PEG400-RGD = 10:6.5:0.5). The values of the intermediate formulations obtained after DELOS production step, before concentration by TFF, are presented between brackets (intermediate formulation). | | | | | | | |
|---|---|---|---|---|---|---|---|
| GLA to membrane excipients ratio (μg GLA/mg membrane excipients) | [GLA] (μg/mL) | [membrane excipients]* (mg/mL) | Macroscopic appearance | Mean size (nm) | PdI | ζ-potential (mV) | Physico-chemical Stability |
| 0 (0) | 0 (0) | 9.0 (1.2) | Homogeneous whitish aqueous and opalescence dispersion without sediment | 113 ± 1 (106 ± 1) | 0.13 ± 0.01 (0.16 ± 0.01) | 50 ± 2 (57 ± 2) | >60 days (>30 days) |
| 20 (21) | 168 (25) | 8.4 (1.2) | Homogeneous whitish aqueous and opalescence dispersion without sediment | 125 ± 2 (151 ± 1) | 0.15 ± 0.02 (0.16 ± 0.01) | 49 ± 1 (41 ± 1) | >60 days (>30 days) |
| 30 (30) | 271 (30) | 9.0 (1.2) | Homogeneous whitish aqueous and opalescence dispersion without sediment | 153 ± 1 (143 ± 4) | 0.09 ± 0.02 (0.17 ± 0.02) | 40 ± 1 (40 ± 2) | >60 days (>30 days) |
| 36 (38) | 326 (45) | 9.0 (1.2) | Milky aqueous dispersion with some sediment | 134 ± 1 (202 ± 7) | 0.26 ± 0.01 (0.40 ± 0.03) | 39 ± 1 (39 ± 1) | <7 days (<3) |
| 41 (38) | 343 (45) | 8.4 (1.2) | Milky aqueous dispersion with some sediment | 134 ± 1 (224 ± 3) | 0.26 ± 0.01 (0.76 ± 0.03) | 39 ± 1 (37 ± 1) | <7 days (<3) |

*DPPC, Cholesterol, Cholesterol-PEG400-RGD, and MKC

As can be seen in Table 7, on the one hand 0, 20 and 30 μg/mL GLA to membrane ratios presented an homogeneous opalescence and stable appearance with time, a mean particle size around 120-150 nm and polydispersity indexes (PdI) below 0.20 in all cases. The concentrated nanoGLA versions, containing up to 271 μg/ml of GLA, were stable for more than two months, and the intermediate formulations for more than one.

On the other hand, batches prepared with higher GLA to membrane ratio of 36 and 41 μg/mg were more milky after preparation, and some sediment appeared in intermediate formulation just few hours after their preparation, leading to sizes around 200 nm and PdI above 0.40. No significant size differences were observed in the final nanoGLA concentrated versions prepared at these high ratios, but PdI were above 0.25 in all cases. Its stability had also been compromised, presenting sedimentation in less than 7 days after their production caused by the formation of aggregates.

Figure 5A:
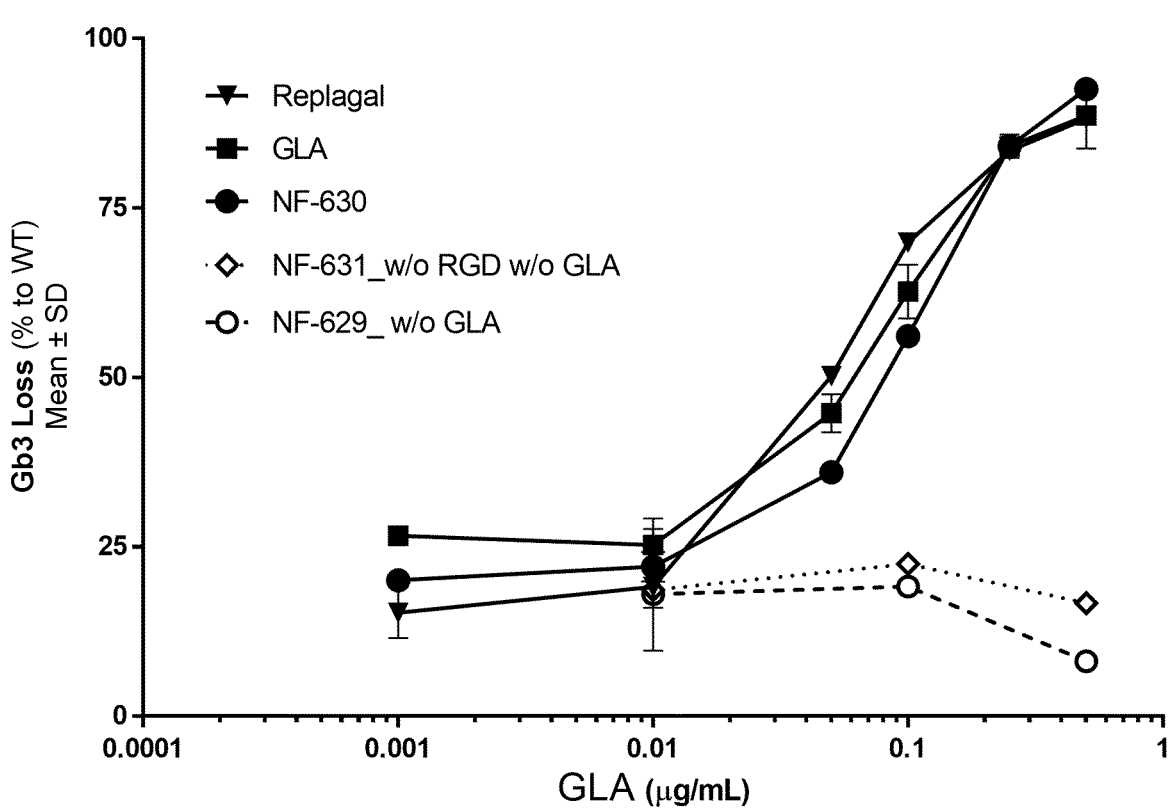
FIG. 5: A, in vitro efficacy assay in MAEC of nanoGLA "NF-630" (liposomes DPPC:Chol:(Chol-PEG400-RGD):MKC) comprising the rh-GLA in a ratio of about 36 compared to the free proteins (GLA final version from LeanBio (rh-GLA) and Replagal®); "NF-631_w/o RGD_w/o GLA" and NF-629_w/o GLA" were used as controls (having the same structure as "NF-630" (with DPPC, chol and MKC) but in "NF-631" without chol-PEG400-RGD and without GLA, and in "NF-629" with chol-PEG400-RGD but without GLA); B, Gb3 reduction in cell culture of the liposomes DPPC:Chol:(Chol-PEG400-RGD):MKC with the rh-GLA in a ratio of 30 (GLA was present in a ratio 30 in GLA in respect to the total milligrams of the components of the liposome a), b), c) and d) (GLA at 271 ug/ml).) ("nanoGLA") in comparison with free rh-GLA, and free Replagal®. "NF-empty" is the nanoformulation constituted by the liposomes DPPC:Chol:(Chol-PEG400-RGD):MKC without GLA).
Figure 5B:
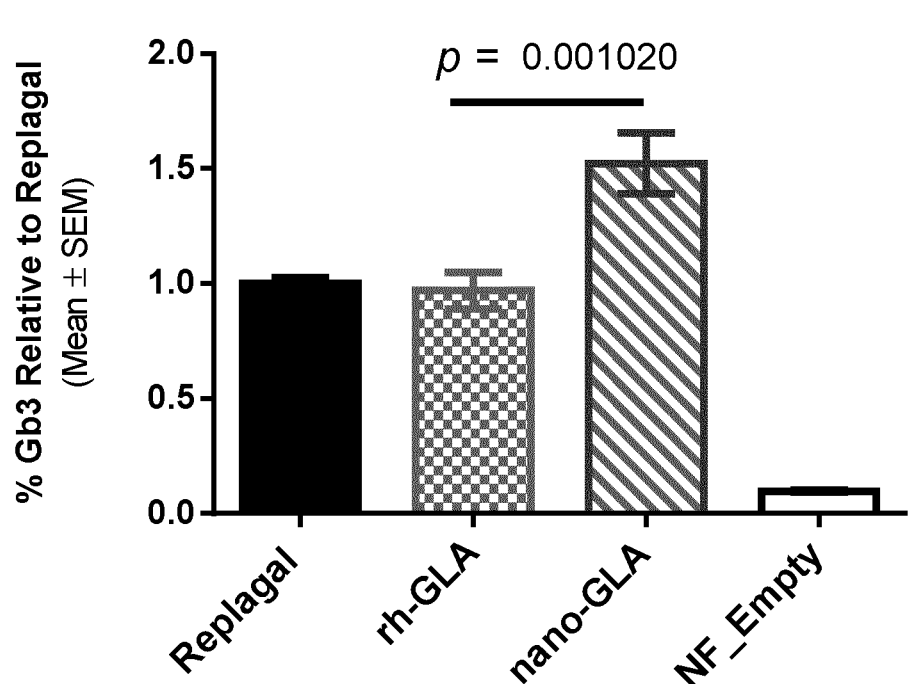

2.2. Impact on In Vitro Enzymatic Efficacy in Cell Cultures of nanoGLA Formulations Ratio GLA/Membrane Components Using the Liposomes of the Invention Wherein the Ratio GLA: Membrane Components was about 30 Micrograms GLA/Mg Membrane Components:

The impact of these higher GLA to membrane ratios on the in vitro efficacy in mouse aortic endothelial cells (MAEC) was also found, leading at the high ratios nanoformulations disclosed in example 2.1 (ratio at least 36) less effective reducing the Gb3 levels (see FIG. 5A, in which the liposomes DPPC:Chol:(Chol-PEG400-RGD):MKC comprising the rh-GLA in a ratio of about 36 (called "NF-630") did not show superior efficacy than the free proteins (Replagal® and rh-GLA)). On the other hand, the liposomes DPPC:Chol:(Chol-PEG400-RGD):MKC comprising the rh-GLA in a ratio of about 30 (μg GLA/mg lipidic membrane components) (named as "nanoGLA" in FIG. 5B) showed better efficacy of nanoformulated enzyme compared to experiments with free GLA, and it had 150% of Replagal®'s activity (see FIG. 5B). As can be seen in FIG. 5B the DPPC:Chol:(Chol-PEG400-RGD):MKC without rh-GLA did not presented activity (named as "NF-empty" in said figure). The liposome DPPC:Chol:(Chol-PEG400-RGD): MKC comprising the rh-GLA effect was not due to a summatory of the effects of the separate items (the empty liposome plus the rh-GLA), but to a surprising synergistic effect, as can be seen in FIG. 5B.

Conclusions:

Therefore, the weight ratio between GLA and membrane excipients had a critical impact on physicochemical properties and stability of nanoGLA formulations prepared with free-tag GLA, 5 mol % of MKC and 3 mol % of Cholesterol-PEG400-RGD. As seen experimentally, a ratio of 36 μg GLA/mg membrane excipients leaded to the formation of aggregates which caused sedimentation of the liposomal dispersion and the obtainment of higher polydispersity values in particle size distribution. This impairment in the physicochemical properties of the nanoformulation had a direct impact on the nanoformulation's efficacy. On the other hand, ratios around 30 μg GLA/mg membrane excipients generated nanoGLA formulations of high quality in terms of physicochemical properties, stability, and consequently, efficacy. Thus, the maximum ratio between GLA and membrane excipients needed to be of less than 36 µg GLA/mg membrane excipients) for a stable nanoGLA formulation.

Example 3. In Vivo Treatment of Fabry Disease Using the Liposome or the Invention

Materials and Methods

All the materials and methods used in this example were the same as indicated in example 1 and example 2 (for the results obtained in 2.2), unless otherwise indicated.

For the in vivo experiments "hybrid-liposomes" (HLP) comprising low MKC (5 mol % of the total membrane components (DPPC, chol, conjugate and non-lipid cationic surfactant)) similar to the HLP of examples 1 and 2 were obtained (as described in material and methods of example 1) but in this case the PEG was PEG400, named herein as "Liposome DPPC:Chol:(Chol-PEG400-RGD):MKC" or "HLP DPPC:Chol:(Chol-PEG400-RGD):MKC" ("nano-GLA"). Therefore, this liposome contained the indicated MKC content and also the phospholipid DPPC, cholesterol, and the RGD unit (tripeptide Arg-Gly-Asp) linked to the cholesterol moiety (chol-PEG400-RGD), wherein the $PEG_{400}$ was covalently attached to the cholesterol by one end via a bond of the type alkyl ether and was covalently attached to the peptide comprising the RGD sequence by the other end via a carbamate bond; wherein the RGD peptide was cyclic cRGDfk (SEQ ID NO: 2) (as described in examples 1 and 2). This liposome was obtained using the DELOS-SUSP method as indicated in examples 1 and 2.

The mol ratio of the DPPC:cholesterol:chol-PEG400-RGD was 10:6.5:0.5. Thus, the chol-PEG400-RGD represented the 3% mol in respect of the components.

For the in vivo experiments, the Liposome DPPC:Chol:(Chol-PEG400-RGD):MKC comprised also a tag-free alpha galactosidase (GLA) or rh-GLA, as indicated in example 2. As being produced in CHO cells, the glycosylation profile of the rh-GLA was comparable to Fabrazyme®. Other possible GLA enzymes that could have been used in this experiment were Fabrazyme® from Sanofi Genzyme, or other sources such as Biosimilars from Fabrazyme®. For the in vivo experiments, the rh-GLA was loaded as indicated in examples 1 and 2 and it was entrapped into the nanoliposomes (liposomes DPPC:Chol:(Chol-PEG400-RGD):MKC) through a noncovalent binding (0.27 mg/mL GLA, ratio 30). Without being bound to any theory, the inventors considered that possibly the rh-GLA enzyme was incorporated in the membrane as a peripheral protein with the active site exposed toward the aqueous phase (opposite to the bilayer), being part of the integrated rh-GLA adsorbed on the surface of the bilayer and another fraction encapsulated inside the nanoliposomes. In the liposome of the invention the ratio of micrograms of GLA in respect to the total milligrams of the components of the liposome was 30 (as described in example 2.2).

Buffer formulation of the pharmaceutical composition for parenteral administration: several media were used in the diafiltration as indicated in table 8 (see below in the result section) in order to select the appropriate buffer for parenteral administration of the liposome of the invention. Materials buffers: MilliQ water as described in Example 1; Sucrose: D-(+)-Sucrose, Fluka Biochemika, CAS 57-50-1; Glucose: D-(+)-Glucose, dextrose, Sigma-Aldrich; Trehalose: D(+)-Trehalose 2-hydrate, PanReac AppliChem, CAS 6138-23-4; Histidine: L-Histidine pure, Panreac AppliChem; Glycine: Glycine BioUltra, Sigma-Aldrich, CAS 56-40-6; NaCl: Sodium Chloride for analysis, PanReac AppliChem, ITW Reagents; sodium phosphate dibasic: Sigma Aldrich, CAS 7558-79-4; Sodium phosphate monobasic dihydrate: Fluka Biochemika, CAS 13472-35-0. PBS 100 mM prepared with: sodium chloride (5.494 mg/mL), sodium phosphate dibasic (0.44 mg/mL), and sodium phosphate monobasic dihydrate (0.14 mg/mL). For the experiments regarding the buffer formulation (related to the result section 3.1 below), the GLA used as a model was the GLAcmycHis described in Corchero J L. et al. 2011.

In vivo enzymatic activity (EA): GLA Plasma content of GLA was determined analysing the EA in plasma after the administration of Liposome DPPC:Chol:(Chol-PEG400-RGD):MKC (diafiltered and concentrated as explained in example 1 and 2), Replagal® or the rh-GLA without the liposome to a Fabry mouse model (Ohshima et al., 1997). Fabry KO mice were administered with 1 mg/kg of GLA in each group and euthanized 1 or 30 min later (4 animals per group and time point).

Single dose efficacy assay: a single intravenous (i.v.) administration of the liposome DPPC:Chol:(Chol-PEG400-RGD):MKC, free rh-GLA or free Replagal® at the dose of 1 mg/kg (dose of the enzyme) was performed to Fabry KO mice (8 animals per group). One week after, mice were euthanized to collect the organ samples (liver, spleen, kidney and heart). Organs were homogenized and Gb3 levels were determined by Liquid chromatography-high resolution mass spectrometry (LC-HRMS). Free rh-GLA and Replagal® were administered at the same dose of 1 mg/kg of GLA (the same amount of protein), to better see if the nanoencapsulation of the enzyme (liposome DPPC:Chol:(Chol-PEG400-RGD):MKC) rendered any advantage over the administration of free GLA (rh-GLA and Replagal®). The methodology and the experimental design used in this assay followed procedures previously used for testing the efficacy of proteins currently in clinical practice or in preclinical development (Ioannou et al., 2001, Shen et al., 2016). For calculation of the relative Gb3 loss, it was assumed that the difference in Gb3 levels between non-treated KO mice and WT counterparts corresponded to a 100% of Gb3 loss in WT. Then, the Gb3 levels in different treatment groups were referred to this total Gb3 loss in WT, meaning that those treatments with a higher percentage of Gb3 loss were the ones with a higher efficacy. "ANOVA test with multiple comparisons and t-test were performed in order to compare results."

Gb3 determinations: Gb3 levels were determined with Liquid chromatography-high resolution mass spectrometry (LC-HRMS) at the Institute of Advanced Chemistry of Catalonia (IQAC-CSIC). In detail, 750 µL of a methanol-chloroform (2:1, vol/vol) solution containing internal standards (N-dodecanoylsphingosine, N-dodecanoylglucosyl-sphingosine, N-dodecanoylsphingosylphosphorylcholine, and N-heptadecanoylceramide trihexoside, 0.2 nmol each) were added to plasma (0.1 mL) or kidney homogenates (0.1 mL, around 0.3 mg/mL protein). Samples were extracted at 48° C. overnight and cooled, 75 µl of 1M KOH in methanol was added, and the mixture was incubated for 2 h at 37° C. Following addition of 75 µL of 1M acetic acid, samples were evaporated to dryness and stored at −20° C. until the analysis of sphingolipids. Before the analysis 150 µL of methanol were add to the samples, centrifuged at 13000 g for 5 min and 130 µL of the supernatant were transferred to a new vial and injected. Sphingolipids were measured with an Acquity ultraperformance liquid chromatography (UPLC) system connected to a time-of-flight (LCT Premier XE) detector controlled with Waters/Micromass MassLynx software. Sample was injected onto an UPLC BEH C8 column (particle size, 1.7 µm; 100 mm by 2.1 mm); flow rate of 0.3 ml/min and column temperature of 30° C. were used. The mobile phase was methanol with 1 mM ammonium formate and 0.2% formic acid (solution A)-water with 2 mM ammonium formate and 0.2% formic acid (solution B). Gradient elution started at 80% solution A, was increased to 90% solution A over 3 min, held for 3 min, increased to 99% solution A over 9 min, and after held for 3 min. Initial conditions were attained for 2 min, and the system was stabilized for 3 min. The acquisition range of the TOF detector was m/z 50 to 1500, the capillary voltage was set to 3.0 kV, the desolvation temperature was 350° C., and the desolvation gas flow rate was 600 liters/h. Quantification was carried out using the ion chromatogram obtained for each compound using 50 mDa windows. The linear dynamic range was determined by injection of standard mixtures. Positive identification of compounds was based on accurate mass measurements with an error<5 ppm and LC retention time, compared to that of a standard (<2%). Quantification of was carried out against internal standard (N-heptade-canoylceramide trihexoside).

Repeated dose efficacy assays: repeated dose efficacy assays were conducted comparing the DPPC:Chol:(Chol-PEG400-RGD):MKC with the rh-GLA (named as "nano-GLA") with component ratio 10:6.5:0.5 (DPPC:Cholesterol: Chol-PEG400-RGD) and contained 5.3% mol MKC, with the free enzymes rh-GLA (named herein as "GLAvf)") and Replagal®. The animals (the same type of animals as used in the single dose experiment explained above, Fabry KO mice, C57BL6 WT mice and non-treated Fabry KO mice as control) were administered with each of the comparing formulations, at 1 mg/kg of each compound (n=6 for each group) up to 8 doses (one at day 1, at day 3, at day 5, at day 8, at day 10, at day 12, at day 15 and at day 17 from the administered dose). WT mice were used as a control and nothing was given to them, they served as a control to know the levels of Gb3 that a WT had (the difference between the levels of Gb3 that an untreated KO had minus those that had a healthy WT were the level of Gb3 that would have to reduce a 100% effective treatment, thus, the 100% Gb3 loss of the graphics included in FIGS. 8 and 9). The mice were then euthanized and the samples (blood, kidneys, liver, spleen, lung, skin, heart and brain) were collected 24 h after the last administration. The Gb3 was analyzed by LC-MS/MS as explained previously. ANOVA test with multiple comparisons and t-test were performed in order to compare results. Differences were considered statistically significant when p<0.05.

sugars (trehalose, glucose, sucrose), amino acids (histidine and glycine), phosphates and other compounds and a standard NaCl solution were assessed.

To begin with, a first trial using PBS 100 mM was assessed. Liposomes comprising in the present case GLA-cmycHis as GLA protein model were prepared by DELOS-SUSP as indicated previously in example 1, depressurizing as usually in water. Then, in the diafiltration step, sample was submitted to 5 cycles of diafiltration using PBS 100 mM instead of water.

Differences after the diafiltration were observed for the sample. First, the macroscopic appearance was slightly whiter just after the diafiltration and some sedimentation was observed after two days. An increase of the PDI was also observed (0.31). Moreover, GLA quantification showed that GLA was lost during the diafiltration. Indicating that the medium used not only could have an impact on the physicochemical properties of the liposomes (size, PDI, morphology) but also could have an impact on the interaction of the GLA with the liposome, and may provoke the detachment of the enzyme from the liposome.

In conclusion, production in water and later diafiltration in PBS liposomes maintained similar physicochemical characteristics. However, GLA can be lost during the diafiltration buffer exchange.

Taking into account these results, buffer exchange by diafiltration seemed to be a good strategy to incorporate the osmolality adjusting agents.

In a second study, a screening of different osmolality adjusting agents was considered, studying the impact that could have on the liposomal characteristics as well as in the entrapment efficiency of the GLA.

First, the concentration of the different compounds was adjusted to be isosmotic to blood (around 270-300 mOsm/Kg), as indicated in table 8 below. Then, the diafiltration in these media was performed in the media shown in table 8, in two different experiments (screening 1 and 2).

TABLE 8

Composition of the media selected for osmolality adjustment with the corresponding concentration to be isosmotic to blood (270-300 mOsm/Kg).

| Buffer/Media | Components | Concentration | | mOsm/Kg | pH | Used in screening . . . |
|---|---|---|---|---|---|---|
| Water | MilliQ water | — | | — | ≈6-7 | 1 & 2 |
| Sucrose 10% | Sucrose | 10% | w/v | 295 | ≈6-7 | 1 & 2 |
| Glucose 5% | Glucose | 5% | w/v | 302 | ≈6-7 | 1 & 2 |
| Trehalose 10% | Trehalose | 10% | w/v | 305 | ≈6-7 | 1 & 2 |
| Hist. 10 mM | Histidine (pH 7 adjust HCl) | 10 | mM | 24 | ≈7 | 1 |
| Hist. 10 mM + 10% sucrose | Histidine Sucrose | 10 10% | mM w/v | 288 | ≈7 | 1 |
| Glycine 2.5% | Glycine | 2.5% | w/v | 299 | nd | 2 |
| Sucr. 8.5% + glycine 0.4% | Sucrose Glycine | 8.5% 0.4% | w/v w/v | 286 | nd | 2 |
| Buffer L. | Mannitol | 30.0 | mg/mL | 277 | 7 | 2 |
| | Sodium phosphate monobasic monohydratate | 2.75 | mg/mL | | | |
| | Sodium phosphate dibasic heptahydrate | 8.0 | mg/mL | | | |
| NaCl 0.9% | NaCl | 0.9% | w/v | 300 | nd | 2 |

Results:
3.1. Parenteral Formulation Comprising the Liposome DPPC:Choi:(Chol-PEG-RGD):MKC and Rh-GLA As parenteral formulations needed to be isosmotic with blood (osmolality around 275-300 mOsm/Kg) to prevent rupture or contraction of the liposomal structure as well as avoid damage to the tissues, different media containing In a first attempt, one batch of GLA-loaded liposomes (DPPC:Chol:chol-PEG400-RGD in a mol ratio of 10:6.5:0.5 with MKC=0.04 mg/mL and GLA 35 µg/mL, prototype named as "NF-411") was produced by DELOS-susp with a theoretical concentration of 35 µg/mL of GLA. The total sample was then diafiltrated against different buffers/media instead of MiliQ water (summarized in table 10/screening 1, obtaining the NF-412 to NF-417, which had the same liposome composition as NF-411 but different media as explained in table 9.

Samples were analysed by DLS (size, PDI and ζ-potential) and GLA concentration was assessed by TGX. Entrapment efficiency was calculated as mass GLA in the Loaded sample per mass of GLA in the Total sample, to see if diafiltration caused the loss of GLA as seen for the PBS previously. Results are summarized in table 9.

taining histidine 10 mM, since sedimentation and milky appearance was observed, in correlation with a higher PDI (NF-416 and NF-417).

In conclusion, after this first screening three possible media provided to the liposomes correct osmolality and physicochemical properties: sucrose 10%, glucose 5%, and trehalose 10%.

In a second attempt, another batch of GLA-loaded liposomes (DPPC:Chol:chol-PEG400-RGD in a mol ratio of

TABLE 9

Physicochemical characterization by DLS (size, PDI and ζ-potential), GLA concentration (by TGX), entrapment efficiency (EE %) and osmolality value. DLS measurements were performed 1-2 days after production. The values in brackets correspond to DLS after 16 days.

| Sample | Medium | Size [nm] | PDI | ζ- pot [mV] | GLA [µg/mL] | EE [%] | mOs m/Kg |
|---|---|---|---|---|---|---|---|
| NF-411 (Original) | EtOH 5%, DMSO 1% | 123.0 ± 0.6 (129.3 ± 3)$^a$ | 0.24 ± 0.01 (0.26 ± 0.01) | 61 ± 4 (56 ± 4) | 23 ± 2 | — | 1039 |
| NF-412 | Diaf. in water | 141.2 ± 0.5 (141 ± 1) | 0.27 ± 0.01 (0.25 ± 0.01) | 48.1 ± 0.6 (39 ± 1) | 20.5 ± 0.1 | 89 ± 8 | −2 |
| NF-413 | Diaf. in sucrose 10% | 123.7 ± 0.8 (134.3 ± 0.8) | 0.23 ± 0.01 (0.23 ± 0.01) | 30.6 ± 0.6 (21.8 ± 0.9) | 20 ± 2 | 90 ± 20 | 280 |
| NF-414 | Diaf. in glucose 5% | 116.0 ± 0.6 (113.5 ± 0.7) | 0.21 ± 0.01 (0.19 ± 0.01) | 46 ± 2 (45.2 ± 0.9) | 22 ± 1 | 100 ± 10 | 299 |
| NF-415 | Diaf. in trehalose 10% | 121 ± 2 (121.8 ± 0.5) | 0.24 ± 0.01 (0.22 ± 0.01) | 36.6 ± 0.7 (30 ± 0.4) | 16.9 ± 0.1 | 73 ± 7 | 301 |
| NF-416 | Diaf. in hist. 10 mM | 210 ± 10$^b$ (214 ± 4)$^c$ | 0.46 ± 0.04$^b$ (0.48 ± 0.03)$^c$ | 39 ± 2 (36.4 ± 0.5) | 21 ± 2 | 90 ± 20 | 29 |
| NF-417 | Diaf. in hist. 10 mM + 10% sucrose | 232 ± 2$^b$ (300 ± 15)$^c$ | 0.43 ± 0.06$^b$ (0.49 ± 0.06)$^c$ | 14.7 ± 0.7 (14.1 ± 0.3) | 23.1 ± 0.2 | 100 ± 10 | 291 |

$^a$Some sediment, but ressuspended well;
$^b$Milky appereance;
$^c$Milky appereance and some sedimentation.

For the diafiltrated ("diaf.") samples in the selected media, all the sugars at the tested concentration (sucrose 10%, glucose 5% and trehalose 10% w/v) let to isosmotic samples, with an osmolality value between 280 and 300 mOsm/Kg. These formulations also maintained good physicochemical characteristics, with a PDI<0.25 and similar size (around 110-130 nm) to the original sample. The encapsulation efficiency was high (>70%) for the three systems, with a slightly lower Entrapment Efficiency (EE) % for the trehalose (73% against 90% and 100%), but this difference was not relevant.

The macroscopic appearance of all the samples was good, with the exception of those diafiltrated in a medium con- 10:6.5:0.5 with MKC=0.04 mg/mL and GLA=25 µg/mL, prototype named as NF-431 (or named as "NF-431 (original)") was produced by DELOS-susp. The total sample was then diafiltrated against different buffers/media instead of MiliQ water, as done in the previous example, obtaining the NF-431 to NF-441 (also with the same liposome composition as NF-431 but in different media as explained in table 10).

Samples were analysed by DLS (size, PDI and ζ-potential) and GLA concentration and the entrapment efficiency were also calculated (see table 10).

TABLE 10

Physicochemical characterization by DLS (size, PDI and ζ-potential), GLA concentration assessed by TGX , entrapment efficiency (EE %) and osmolality value. DLS measurements were performed 1-2 days after production. The values in brackets correspond to DLS after 8-10 days.

| Sample | Medium | Size [nm] | PDI | ζ- pot [mV] | GLA [µg/mL] | EE [%] | mOs m/Kg |
|---|---|---|---|---|---|---|---|
| NF-431 (Original) | EtOH 5%, DMSO 1% | 119 ± 3 (119.8 ± 0.7) | 0.28 ± 0.03 (0.27 ± 0.01) | 61 ± 2 (55 ± 2) | 19.6 ± 0.4 | — | 1059 |
| NF-436 | Diaf. in water | 135 ± 2 (127.3 ± 0.9) | 0.30 ± 0.05 (0.26 ± 0.01) | 33 ± 2 31 ± 2 | 18.7 ± 0.6 | 95 ± 5 | 2 |
| NF-433 | Diaf. in glucose 5% | 109.0 ± 0.4 (106.8 ± 0.8) | 0.21 ± 0.01 (0.20 ± 0.01) | 48 ± 1 (52 ± 3) | 19 ± 1 | 97 ± 7 | 289 |
| NF-434 | Diaf. in LB buffer | 125.0 ± 0.5 (123.4 ± 0.9) | 0.19 ± 0.01 (0.20 ± 0.01) | 13.2 ± 0.6 (13.8 ± 0.6) | 0* | 0 | 275 |
| NF-435 | Diaf. in sucrose 10% | 141 ± 1 (162 ± 2)$^a$ | 0.23 ± 0.01 (0.26 ± 0.01) | 27 ± 2 (22 ± 8) | 18 ± 1 | 90 ± 8 | 287 |
| NF-437 | Diaf. in trehalose 10% | 118.7 ± 0.9 (122 ± 3) | 0.25 ± 0.01 (0.23 ± 0.01) | 39.5 ± 0.6 (40 ± 1) | 18.6 ± 0.2 | 95 ± 3 | 347 |

TABLE 10-continued

Physicochemical characterization by DLS (size, PDI and ζ-potential), GLA concentration assessed
by TGX , entrapment efficiency (EE %) and osmolality value. DLS measurements were performed
1-2 days after production. The values in brackets correspond to DLS after 8-10 days.

| Sample | Medium | Size [nm] | PDI | ζ- pot [mV] | GLA [μg/mL] | EE [%] | mOs m/Kg |
|---|---|---|---|---|---|---|---|
| NF-438 | Diaf. in glycine 2.5% | 127.5 ± 0.6 (124 ± 1) | 0.26 ± 0.01 (0.23 ± 0.01) | 34.5 ± 0.6 (35 ± 2) | 21.6 ± 0.6 | 110 ± 6 | 297 |
| NF-440 | Diaf. in sucrose 8.5% + glycine 0.4% | 143 ± 3 (174.4 ± 0.8)$^a$ | 0.24 ± 0.01 (0.25 ± 0.02) | 26 ± 3 (30 ± 2) | 17.1 ± 0.1 | 87 ± 2 | 282 |
| NF-441 | NaCl 0.9% | 125 ± 1 (134.1 ± 0.8)$^b$ | 0.25 ± 0.01 (0.41 ± 0.03) | 6.2 ± 0.6 (6.5 ± 0.5) | 0* (8) | 0 | 256 |

In this set of diafiltrated samples, additional media were also tested: the buffer from LeanBio (similar to the composition of Fabrazyme®, containing mannitol and sodium phosphates), glycine 2.5%, a mixture sucrose 8.5% and glycine 0.4%, and finally sodium chloride 0.9%.

It was seen that all the media at the tested concentration let to isotonic samples, with an osmolality value between 250 and 300 mOsm/Kg. To point out, the sample containing trehalose (NF-437) showed a higher osmolarity than it was expected (347 mOsm/Kg, against 301 mOsm/Kg obtained in the first assay (NF-415) and 295 mOsm/Kg for trehalose 10% stock).

These formulations also maintained good physicochemical characteristics, with a PDI<0.30 and similar size (around 110-170 nm) compared to the original one. In the case of samples containing sucrose, they turned a little milky after one week, with a slightly increase in size specially for the sample that also contained glycine (NF-440), but PDI was not affected.

Figure 6A:
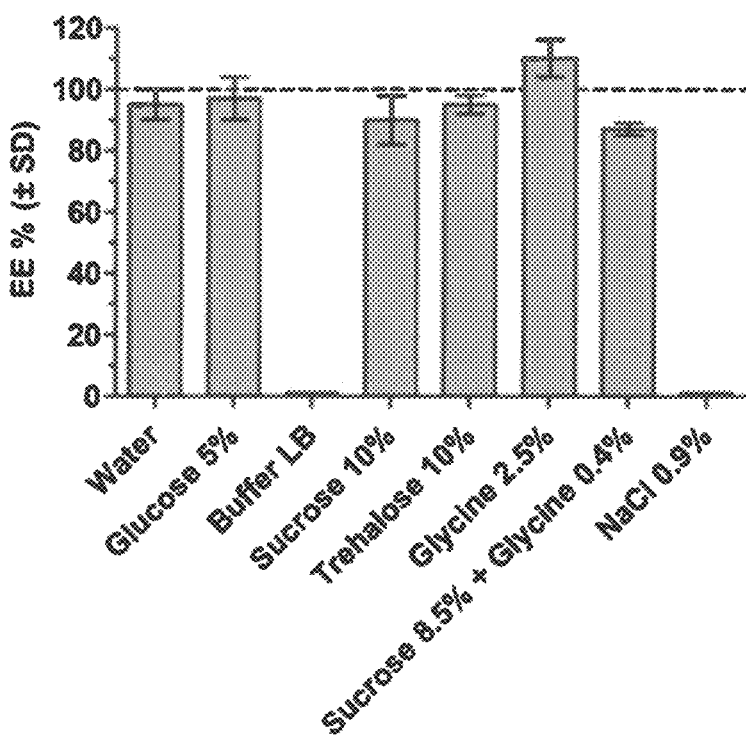
FIG. 6. A, Entrapment efficiencies for nano-GLA diafiltrated in different media. B, Specific enzymatic activity (EA) of nano-GLA samples, in relation to the control (Replagal® enzymatic activity was normalized to 1). C, In vitro efficacy assay in MAEC of nano-GLA samples diafiltrated in an aqueous solution of glucose 5% and sucrose 10%, and nano-GLA samples 7-fold concentrated and diafiltrated in an aqueous solution of glucose 5% and sucrose 10%.

Regarding the entrapment efficiency, two trends were observed (see FIG. 6A): on the one hand, GLA was well incorporated when sugars or amino acids were used as osmotic agents, since it was kept after the diafiltration. In this case, high entrapment efficiencies were obtained (<85%), as seen in samples diafiltrated in glucose, sucrose, trehalose, glycine and sucrose/glycine. On the other hand, when salts were used (e.g., sodium chloride, or phosphates) they provoked a separation of the GLA from the liposomes, leading to its loss during the diafiltration. This effect was seen in samples diafiltrated in the buffer containing sodium and phosphates, NaCl, and in the first experiment done with PBS.

Figure 6B:
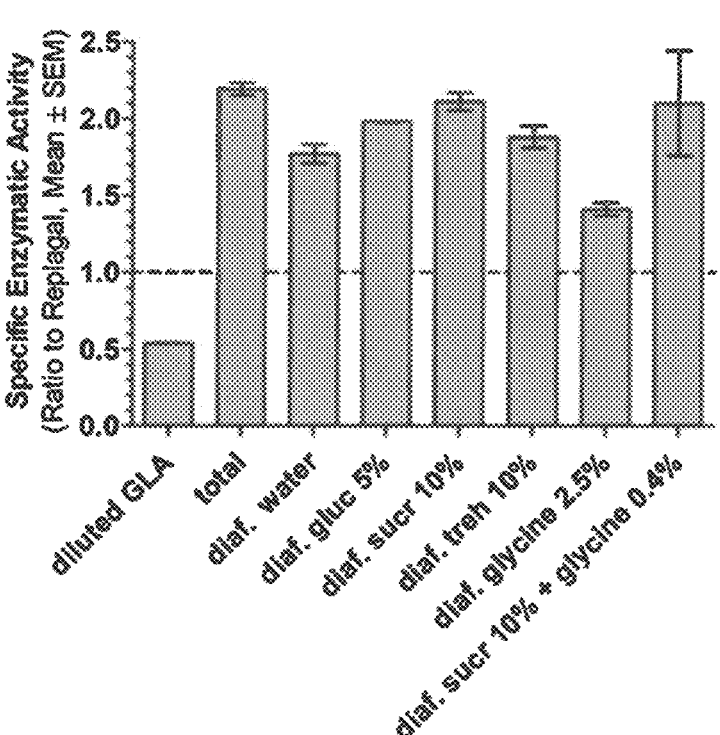

Next, GLA enzymatic activity was also evaluated for this second screening of media (FIG. 6B). Diluted GLA in water ity (that was higher than Replagal®) in all the tested media, despite the fact that the GLA in glycine seemed to show a slightly less EA than in the rest of samples.

In conclusion, glucose 5%, sucrose 10%, and trehalose 10% showed the best results to obtain an isosmotic nano-formulation, able to keep good physicochemical characteristics, GLA concentration and enzymatic activity.

Figure 6C:
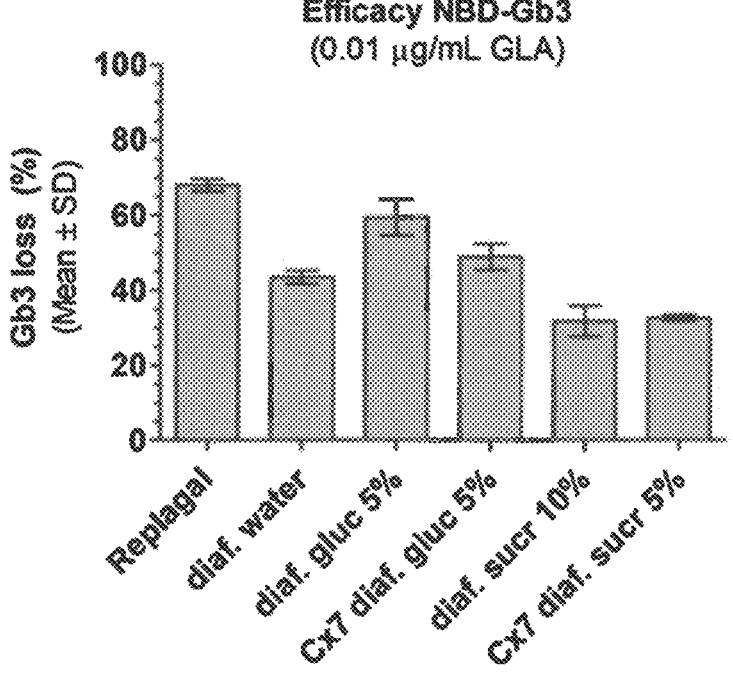

In a last experiment related to in vitro efficacy (Gb3 reduction), a comparison between the liposomes (DPPC: Chol:chol-PEG400-RGD in a mol ratio of 10:6.5:0.5 with MKC=0.04 mg/mL (5% mol MKC) and GLA=25 g/mL) in glucose 5%: and sucrose 10% as the isosmotic media was performed (diafiltrated in glucose 5% or in sucrose 10%, or concentrated ×7 and diafiltered in glucose 5% or sucrose 10%), studying the ability of GLA-loaded liposomes to reach the lysosomes and hydrolyse Gb3. This was tested in primary cultures of mouse aortic endothelial cells (MAEC) from GLA deficient mice (same material and methods explained in Example 1). Results showed that liposomes formulated with glucose 5% presented higher in vitro efficacy (Gb3 reduction) than liposomes formulated with sucrose 10% (FIG. 6C).

Therefore, the final pharmaceutical form determined for use in the in vivo experiments ("nano-GLA") was an aqueous nanoliposomal dispersion. The components and the role of each of the components in the nano-GLA are described in the following Table 11 (wherein the MKC was at 5% mol, the weight ratio of GLA/liposome membrane excipients as explained before was 30 and the glucose was at 5% w/v). The nano-GLA composition disclosed in table 11 comprised the tag-free "rh-GLA" explained in previous example, instead of the GLAcmycHis in the experiment for the selection of the isosmotic media.

TABLE 11

Nano-GLA and roles of the components in nano-GLA.

| Components | Amount per mL | Role |
|---|---|---|
| rh-GLA | 0.27 mg | Active Pharmaceutical Ingredient |
| Cholesterol | 2.1 mg | Membrane component |
| Cholesterol-PEG$_{400}$-RGD | 0.59 mg | Membrane component with the targeting moiety |
| DPPC | 6.2 mg | Membrane component |
| MKC | 0.30 mg | Stabiliser |
| Dimethylsulfoxide (DMSO) | Traces | Solubiliser of membrane components |
| Ethanol | Traces | Solubiliser of membrane components |
| Glucose | 50 mg | Isosmotic agent |
| Water for injection | q.s. 1 mL | Dispersant medium |

(just before the depressurization by DELOS-SUSP) showed a sharp decline of enzymatic activity, around the half the Replagal® (normalized to 1). Whereas, the GLA entrapped into the nanoliposomes maintained its good enzymatic activ-

3.2. In Vivo Enzymatic Activity (EA)

Figure 7:
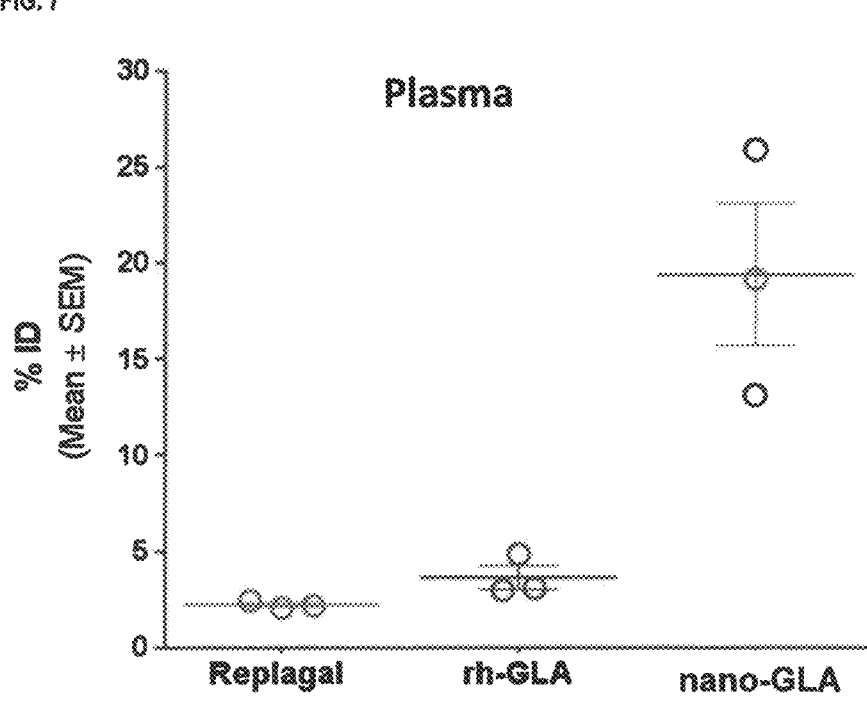
FIG. 7: Plasma activity of the liposomes DPPC:Chol:(Chol-PEG400-RGD):MKC with the rh-GLA, free rh-GLA, and free Replagal®. In plasma, the enzymatic activity (EA) at 30 min post-administration was referred to activity at 1-min in order to calculate the percentage of injected dose (ID).

The liposome DPPC:Chol:(Chol-PEG400-RGD):MKC with rh-GLA (in the formulation disclosed in table 11) increased the EA levels in plasma over the free enzymes (Replagal® or rh-GLA) (FIG. 7). Thirty minutes after administration, plasma retained 18.9±0.7% of the Injected Dose (ID) (as referred to 1 min) when GLA was nanoformulated in the liposome of the invention as described in previous section 3.1, and only 2.9±0.2% ID in the case of free enzymes (p=0.024). Therefore, the liposome DPPC:Chol:(Chol-PEG400-RGD):MKC (wherein the MKC was at 5% mol, the weight ratio of GLA/liposome membrane excipients as explained before was 30) extended the in vivo circulation life of the active principle (GLA).

3.3. In Vivo Single Dose Efficacy Assay

The in vivo efficacy of the nano-GLA was tested in the Fabry KO mice by comparing the Gb3 levels in animals treated with a single dose of liposome DPPC:Chol:(Chol-PEG400-RGD):MKC with rh-GLA (in the formulation disclosed in table 11) (components of the liposome as described in previous sections 3.1 and 3.2), free (non-entrapped) rh-GLA or the clinically available Replagal® (free enzyme as well). Being the Fabry KO mice model (GlatmKul in C57BL6 background) the most widespread animal model for FD and which had a complete absence of the GLA gene (Ohshima et al., 1997). These mice exhibited typical lipid inclusions with lamellar structures in the lysosomes and progressive accumulation of Gb3 in target tissues, including heart and kidneys, following the same pattern as in the human Fabry patients. C57BL6 WT mice and non-treated Fabry KO mice were also included as controls.

Figure 8A:
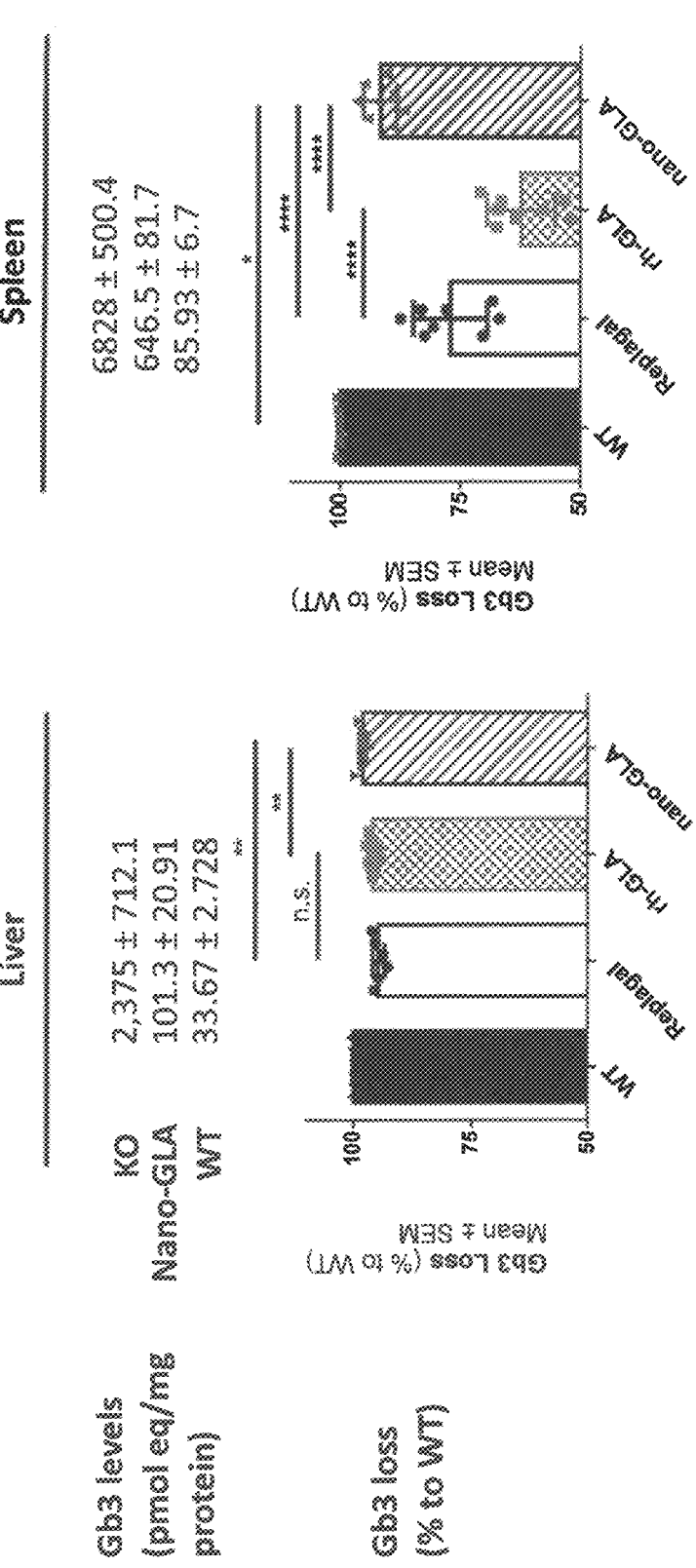
FIG. 8 In vivo efficacy of single dose of the liposomes DPPC:Chol:(Chol-PEG400-RGD):MKC with the rh-GLA in comparison with free rh-GLA, and free Replagal® in (A) liver and spleen, and (B) kidney and heart of a Fabry KO mice model.
Figure 8B:
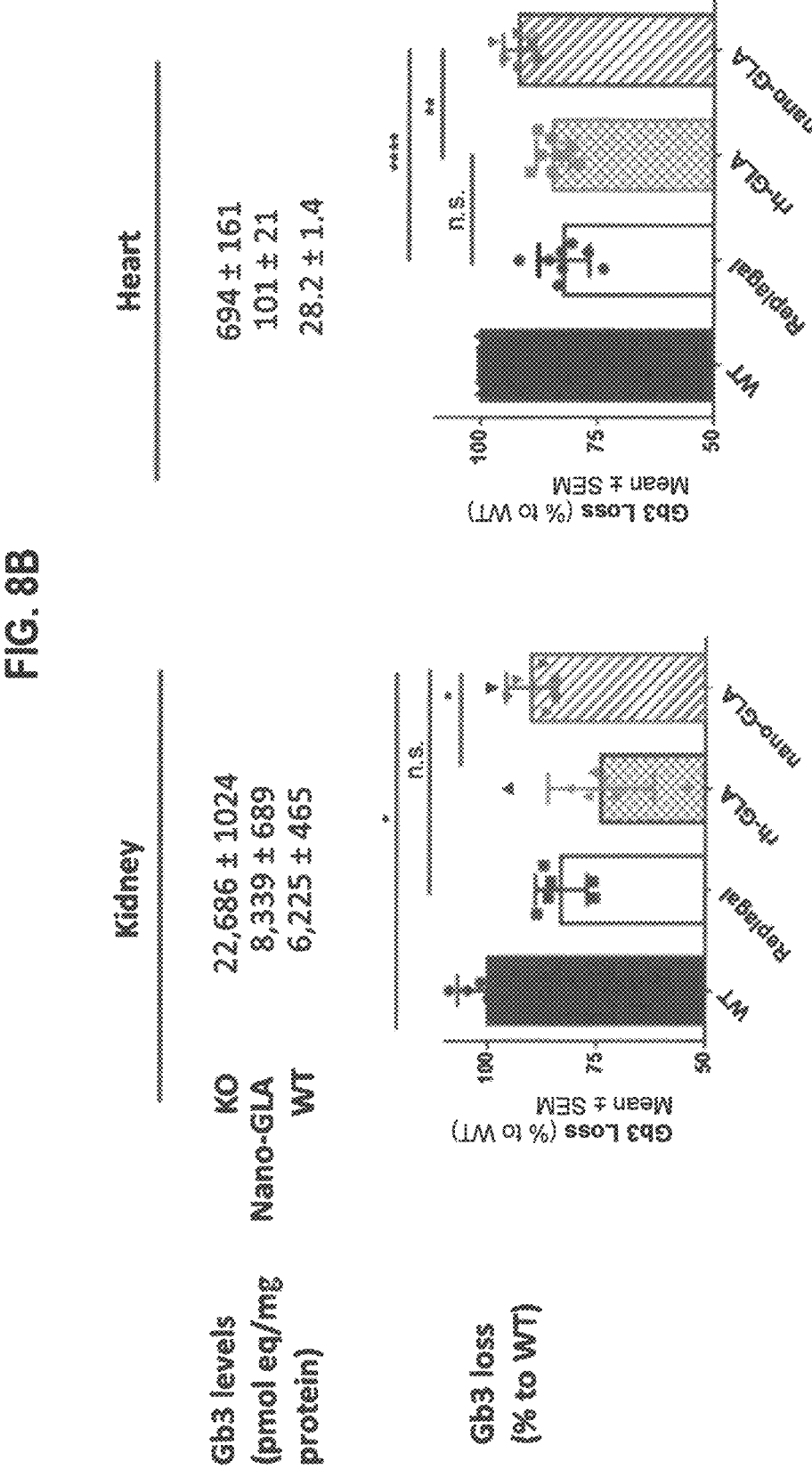
Figure 10:
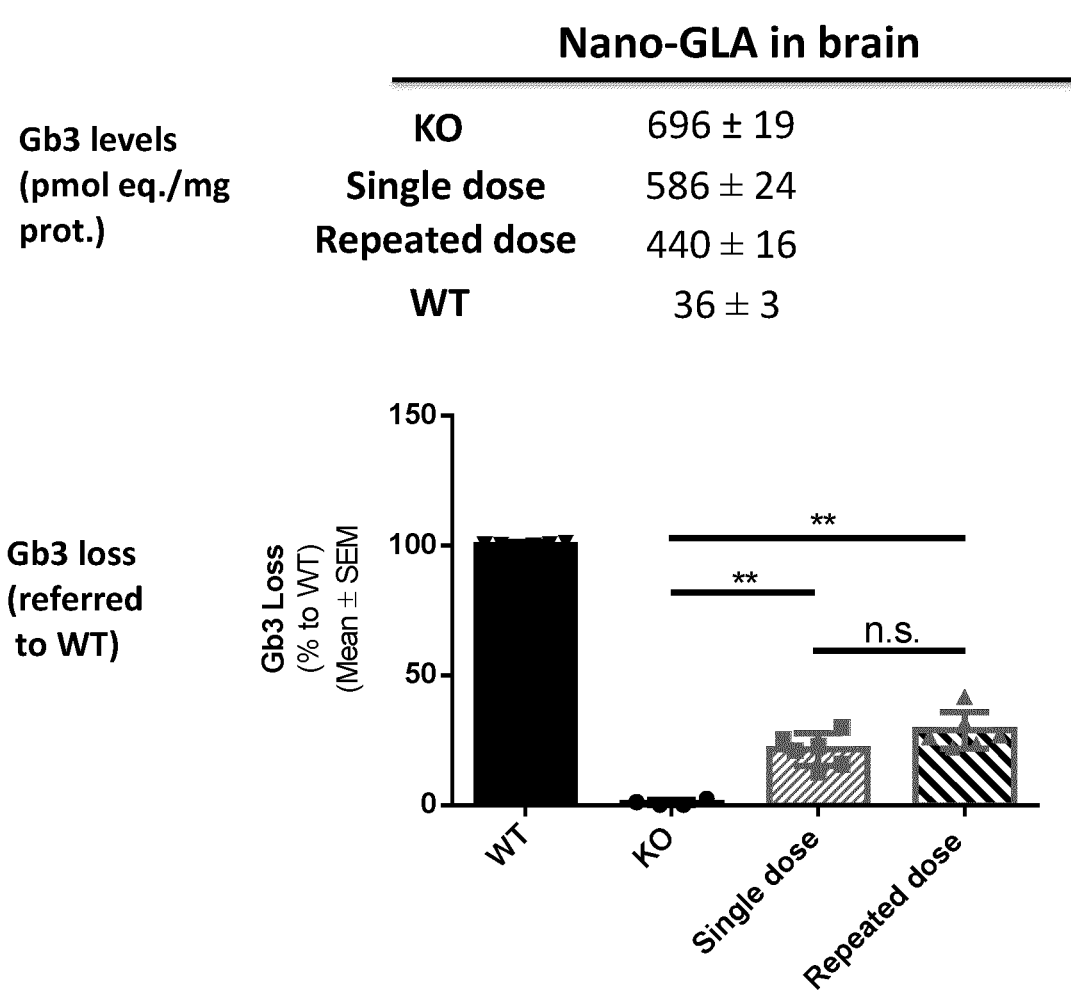
FIG. 10 In vivo efficacy of liposomes DPPC:Chol:(Chol-PEG400-RGD):MKC with the rh-GLA in comparison with free rh-GLA, and free Replagal® in brain of a Fabry KO mice model after a single and repeated intravenous administrations.

For the sake of clarity, in FIG. 8, both, the absolute Gb3 levels (in pmol eq/mg of protein) and the relative Gb3 loss (%) were represented. Gb3 levels varied significantly among tissues of GLA KO mice, being the kidneys, spleen, heart and the brain, the tissues mostly affected by the Gb3 accumulation (as can be seen in FIG. 8). Comparatively, spleen showed lower levels of Gb3. Gb3 levels in non-treated KO mice (KO in FIG. 8) were high in kidney (22,686±1024 μmol/mg) and spleen (6,828±500.4 μmol/mg), followed by heart (694±161 μmol/mg) and liver (2,375±712.1 μmol/mg). In addition, reduction of approximately 21% of Gb3 levels was also observed in brain when mice were treated with a single dose of nano-GLA (FIG. 10).

For calculation of the relative Gb3 loss, it was assumed that the difference in Gb3 levels between non-treated KO mice and WT counterparts corresponded to a 100% of Gb3 loss in WT. Then, the Gb3 levels in different treatment groups were referred to this total Gb3 loss in WT, meaning that those treatments with a higher percentage of Gb3 loss were the ones with a higher efficacy. In spleen, liver and heart the levels of Gb3 were significantly better reduced by liposome DPPC:Chol:(Chol-PEG400-RGD):MKC (nano-GLA) than by Replagal® treatment, meaning that the encapsulation of the protein in the liposome of the invention improved its efficacy.

3.4. In Vivo Repeated-Dose Efficacy Assay

Figure 9A:
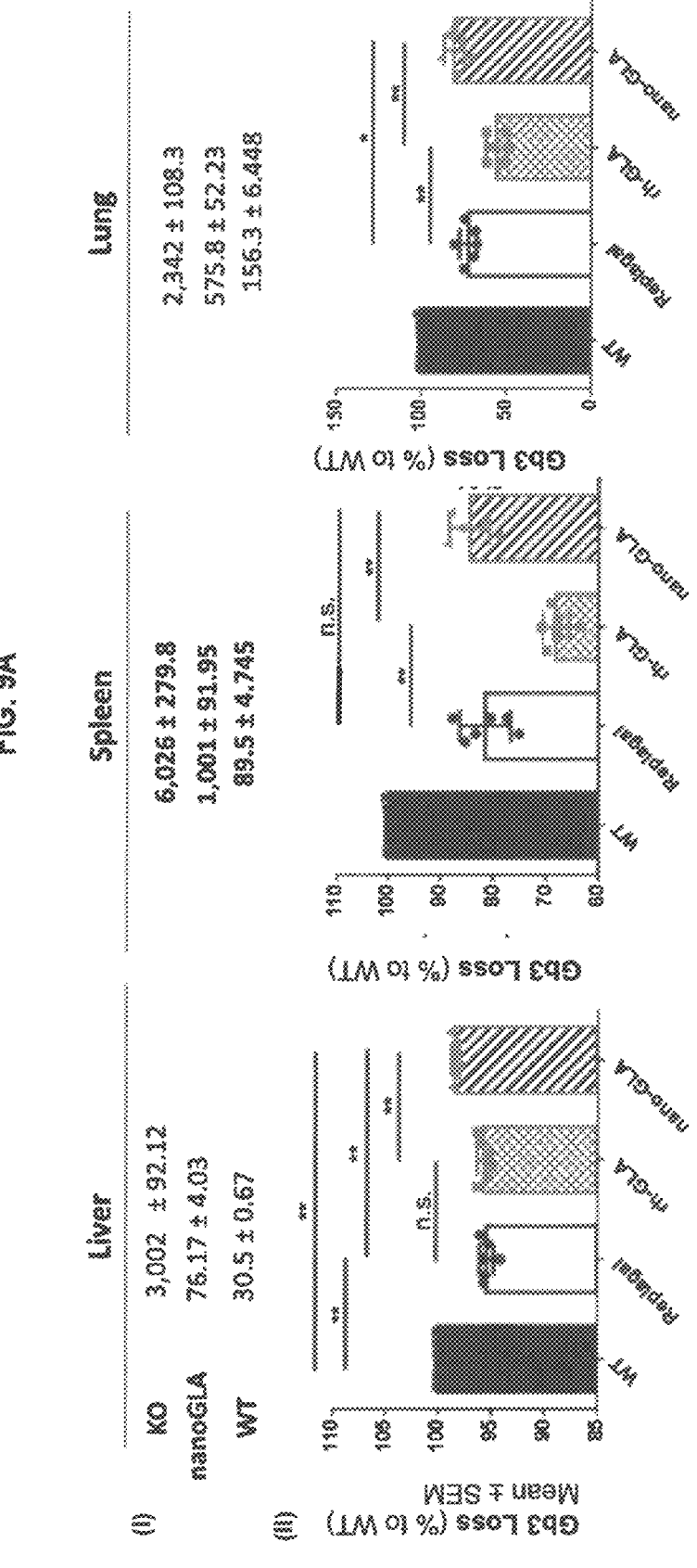
FIG. 9 In vivo efficacy of repeated-dose of the liposomes DPPC:Chol:(Chol-PEG400-RGD):MKC with the rh-GLA in comparison with free rh-GLA, and free Replagal® in (A) liver, spleen and lung, (B) plasma, kidney, and heart, and (C) skin of a Fabry KO mice model. "(I)", Gb3 levels pmol eq/mg prot; and "(II)", Gb3 loss (referred to WT).
Figure 9B:
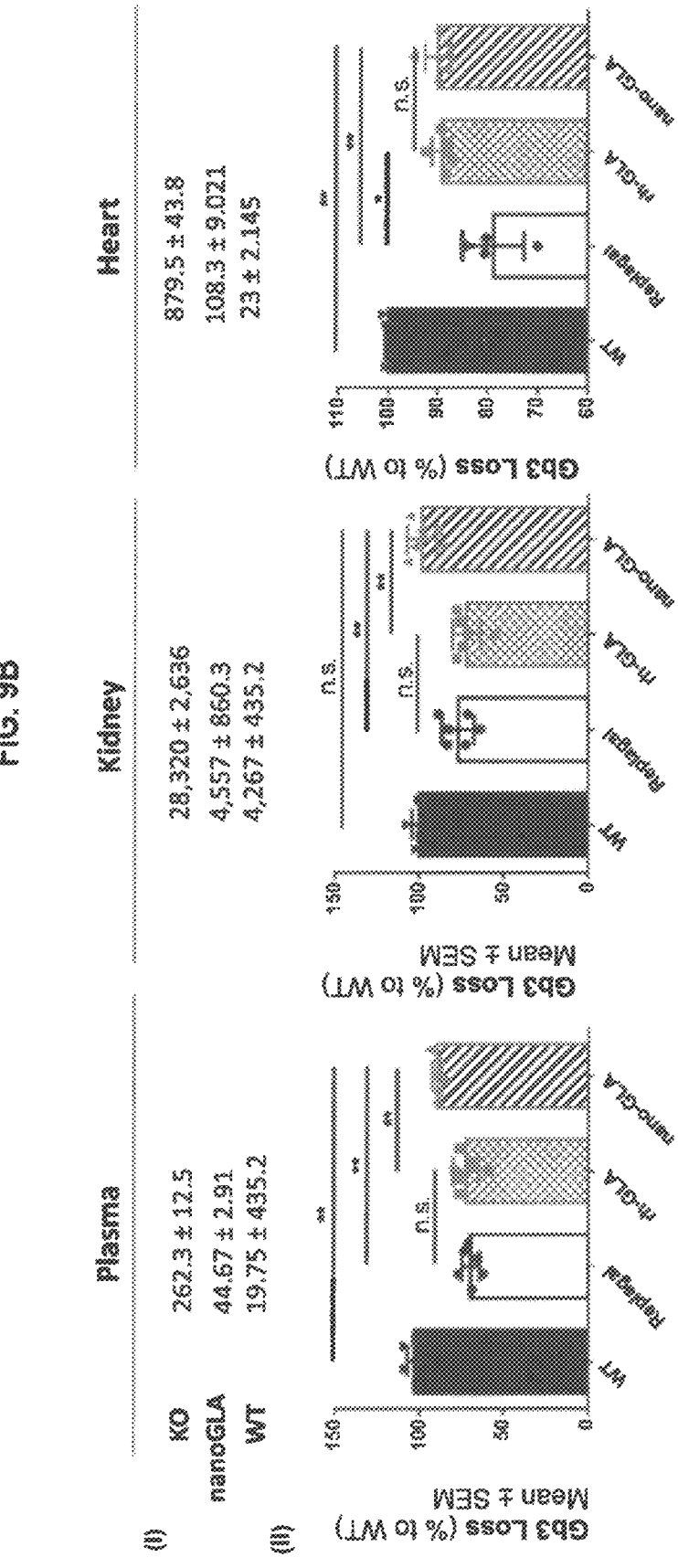
Figure 9C:
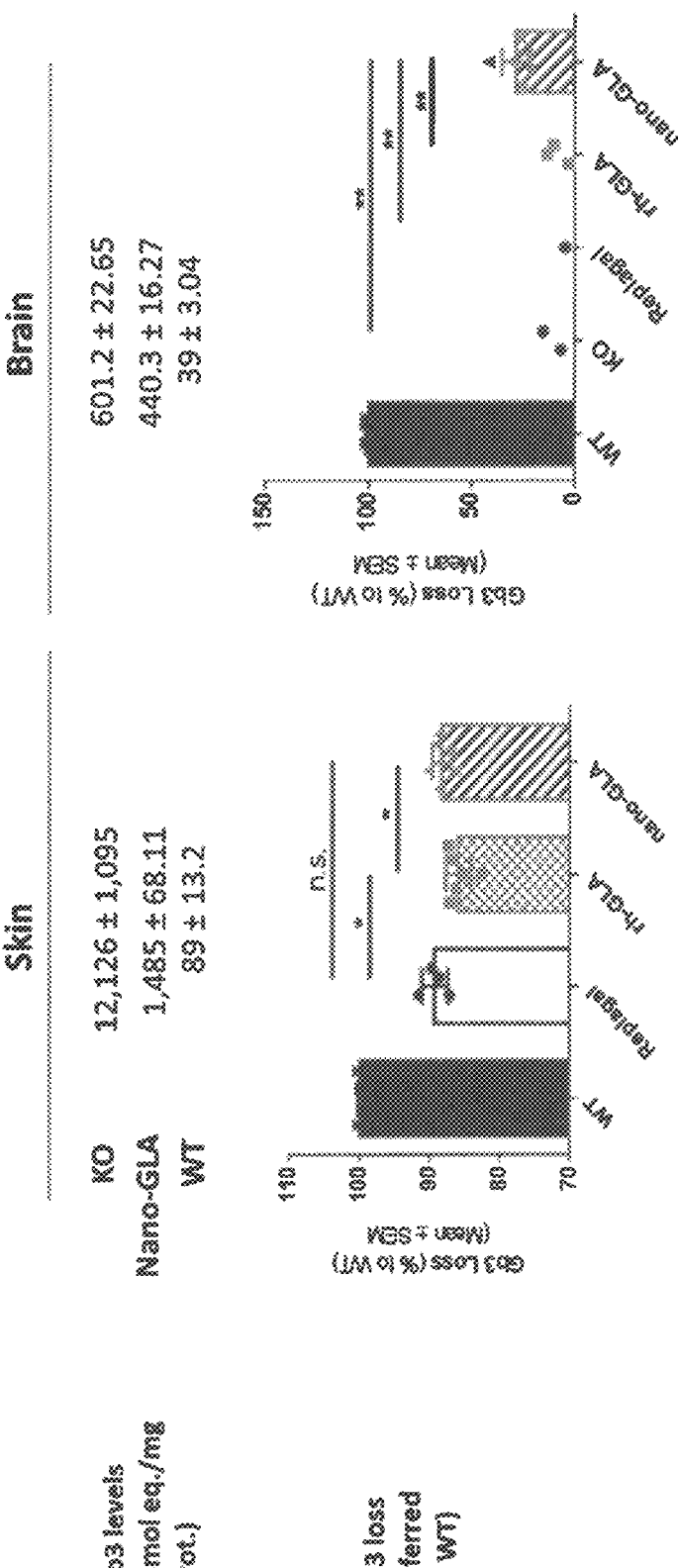

The obtained results showed that, after 8 intravenous administration of 1 mg/kg equivalents to Fabry KO mice and their WT littermates the nanoformulated rh-GLA in the liposome DPPC:Chol:(Chol-PEG400-RGD):MKC (nano-GLA) (in the formulation disclosed in table 11) induced a Gb3 loss in all tested tissues (see FIG. 9). It was also found that the nano-GLA outperformed the free rh-GLA (GLAvf) in plasma, liver, spleen, lung, kidney and skin in the Gb3 loss attained. It was also found that nano-GLA in repeated-dose was able to reduce in approximately 29% the Gb3 deposits in brain. This efficacy in brain was higher than the observed in a single administration of nano-GLA although these differences were not significant (see FIG. 10).

CITATION LIST

Patent Literature

WO2014001509
WO2006/079889

Non Patent Literature

Najafian B. et al., Kidney Int. 79:663-670 (2011).
Schiffmann R. et al., Kidney Int. 91(2):284-293 (2017).
Hsu M J et al., J. Control Release 149(3):323-331 (2011).
Lee K., et al., Glycobiology 13(4):305-313 (2003)
Fervenza, F. C., et al., Biologics: Targets and Therapy vol. 2 823-843 (2008).
Cabrera, I., et al., Adv. Healthc. Mater. 5, 829-840 (2016).
Cabrera, I., et al., Nano Lett. 13, 3766-3774 (2013).
Corchero J. L., et al. Biotechnol. Prog., 2011, Vol. 27, No. 5 p. 1206-1217.
Altschul et al., "Basic local alignment search tool", J. Mol. Biol, v. 215, pages 403-410 (1990).
Higgins et al., CABIOS, 8(2), pages 189-191 (1992).
Sambrook J. et al. Molecular Cloning a Laboratory Manual, Third Edition. Cold Spring Harbor Laboratory Press. Chapter 16, 16.1-16-54.
Ferrer-Tasies, L., et al., Langmuir 29, 6519-6528 (2013).
Cristobal-Lecina, E. et al., ACS Omega 5, 5508-5519 (2020).
Danino, D. Cryo-TEM of Soft Molecular Assemblies. Curr. Opin. Colloid Interface Sci. 17, 316-329 (2012).
Pedersen, J. S. J. Appl. Crystallogr. 37, 369-380 (2004).
Schwamberger, A., et al., Atoms 343, 116-122 (2015).
Li, Y., et al., J. Appl. Crystallogr. 41, 1134-1139 (2008).
Desnick R. J. J. Lab. Clin. Med. 81, 157-171 (1973).
Mayes, J. S., et al., Clin. Chim. Acta 112, 247-251 (1981).
Ohshima, T., et al., Proc. Natl. Acad. Sci. U.S.A 94, 2540-4 (1997).
Botella P et al. J. Control. Release 156, 246-257 (2011).
Giannotti, M. I., et al., ACS Appl. Mater. Interfaces 8, 25741-25752 (2016).
Steiner, E. M., et al., Proteins Struct. Funct. Bioinforma. 86, 912-923 (2018).
Hosemann, R. & Bagchi, S. N. Direct Analysis of Diffraction by Matter. Science 141, (1963).
Pabst, G., et al. Phys. Rev. E—Stat. Physics, Plasmas, Fluids, Relat. Interdiscip. Top. 62, 4000-4009 (2000).
Pabst, G., et al., J. Appl. Crystallogr. 36, 1378-1388 (2003).
T. Miyoshi, et al., Biochim. Acta Biophys—Biomembr. 1838, 3069-3077 (2014).
Ioannou et al. Am. J. Hum. Genet. 68:14-25, 2001.
Shen, J. S., et al. Journal of Inherited Metabolic Disease, 39(2), 293-303 (2016).

The invention claimed is:

1. A liposome comprising
   a) a phospholipid which is dipalmitoylphosphatidylcholine (DPPC);
   b) cholesterol (chol);
   c) a conjugate comprising a cholesterol moiety, a polyethylene glycol (PEG) moiety and a peptide moiety comprising a RGD sequence, wherein the PEG moiety is covalently attached to the cholesterol moiety by one end via a bond of the type alkyl ether and is covalently attached to the peptide moiety comprising the RGD sequence by the other end:
   d) myristalkonium chloride (MKC) present in a percentage of between 0.4 and 4.3% mol with respect to the total mol of the components of the liposome a), b), c) and d); and
   e) alpha-galactosidase enzyme (GLA) present in a ratio of micrograms of GLA in respect to the total milligrams of the components of the liposome a), b), c) and d) of between and including 2 μg/mg to 35 μg/mg.

2. The liposome according to claim 1 wherein, in the alpha-galactosidase enzyme, each of its monomers is either of sequence SEQ ID NO: 1, or of sequence with at least 85% of sequence identity with SEQ ID NO: 1.

3. The liposome according to claim 1, wherein the alpha-galactosidase enzyme is obtained from a Chinese Hamster Ovary (CHO) cell culture.

4. The liposome according to claim 1, wherein the PEG moiety has a molecular weight from 50 to 600 Daltons.

5. The liposome according to claim 1, wherein the PEG, moiety has a molecular weight of 400 Daltons, the RGD sequence is SEQ ID NO: 2, the ratio of micrograms of GLA to milligrams of the components of liposome a), b), c), and d) is between 20-30 μg/mg, wherein, in the GLA, each of its monomers is either of sequence SEQ ID NO: 1, or of sequence with at least 85% of sequence identity with SEQ ID NO: 1, and the mol ratio DPPC:chol:chol-PEG-RGD is 10:6.5:0.5.

6. The liposome according to claim 4, wherein the PEG moiety has a molecular weight from 200 to 400 Daltons.

7. A pharmaceutical composition comprising a therapeutically effective amount of liposomes as defined in claim 1, together with pharmaceutically acceptable excipient(s), carriers, or vehicles.

8. The pharmaceutical composition according to claim 7 further comprising glucose, sucrose or trehalose in an amount from 2 to 10% in weight with respect to the total volume of the composition.

9. The pharmaceutical composition according to claim 7, wherein GLA is present in an amount of at least 0.2 mg per mL of the pharmaceutical composition.

10. A process for the production of a liposome according to claim 1 comprising the following steps:
    a) preparing an aqueous solution which comprises the GLA enzyme;
    b) preparing a solution comprising the conjugate, cholesterol and a phospholipid dissolved in an organic solvent;
    c) adding MKC, either to the solution of the step a), or to the solution of the step b);
    d) expanding the solution of step b) with a compressed fluid, wherein, when the MKC is added to the solution of step b), the expanding step occurs after the MKC has been added;
    e) depressurizing the expanded solution resulting from the step d) over the resulting solution of the step a); and
    f) diafiltrating and concentrating, in any order, the resulting solution obtained in step e).

11. A method for the treatment of Fabry disease, which comprises administering the liposome according to claim 1 to a subject in need thereof.

12. The method according to claim 11, wherein the liposome is administered to a subject suffering Fabry disease as a single dose; or, alternatively, repeatedly at least once every two weeks.

13. A method for the treatment of Fabry disease, which comprises administering the pharmaceutical composition according to claim 7 to a subject in need thereof.

14. The method according to claim 13, wherein the pharmaceutical composition is administered to a subject suffering Fabry disease as a single dose; or, alternatively, repeatedly at least once every two weeks.

* * * * *

SEQUENCE LISTING

```
<160> NUMBER OF SEQ ID NOS: 2

<210> SEQ ID NO 1
<211> LENGTH: 398
<212> TYPE: PRT
<213> ORGANISM: Homo sapiens

<400> SEQUENCE: 1
```

-continued

```
Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
        130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
            165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
    210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
            245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
            325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
    370                 375                 380

Gln Leu Glu Asn Thr Met Gln Met Ser Leu Lys Asp Leu Leu
385                 390                 395
```

<210> SEQ ID NO 2
<211> LENGTH: 5

-continued

```
<212> TYPE: PRT
<213> ORGANISM: Artificial Sequence
<220> FEATURE:
<223> OTHER INFORMATION: peptide, wherein the R, G, D, and K are
      L-aminoacids and F is D-aminoacid

<400> SEQUENCE: 2

Arg Gly Asp Phe Lys
1               5
```